(12) United States Patent
Arnold et al.

(10) Patent No.: US 8,802,401 B2
(45) Date of Patent: Aug. 12, 2014

(54) METHODS AND COMPOSITIONS FOR PREPARATION OF SELECTIVELY PROTECTED CARBOHYDRATES

(75) Inventors: Frances H. Arnold, La Canada, CA (US); Chi-Huey Wong, Rancho Santa Fe, CA (US); Yuuichi Mitsuda, Ikeda (JP); Michael M. Chen, Pasadena, CA (US); Clay Bennett, Medford, MA (US); William Greenberg, San Diego, CA (US); Jared Crawford Lewis, Pasadena, CA (US); Sabine Bastian, Saarbruecken (DE)

(73) Assignees: The California Institute of Technology, Pasadena, CA (US); The Scripps Research Institute, La Jolla, CA (US)

( * ) Notice: Subject to any disclaimer, the term of this patent is extended or adjusted under 35 U.S.C. 154(b) by 850 days.

(21) Appl. No.: 12/141,348

(22) Filed: Jun. 18, 2008

(65) Prior Publication Data

US 2009/0124515 A1    May 14, 2009

Related U.S. Application Data

(60) Provisional application No. 60/936,044, filed on Jun. 18, 2007, provisional application No. 60/936,774, filed on Jun. 22, 2007.

(51) Int. Cl.
| | |
|---|---|
| *C12P 7/00* | (2006.01) |
| *C12P 21/06* | (2006.01) |
| *C12P 21/04* | (2006.01) |
| *C12N 9/02* | (2006.01) |
| *C12N 15/00* | (2006.01) |
| *C07H 21/04* | (2006.01) |

(52) U.S. Cl.
USPC .......... 435/132; 435/189; 435/440; 435/69.1; 435/71.1; 536/23.2

(58) Field of Classification Search
None
See application file for complete search history.

(56) References Cited

U.S. PATENT DOCUMENTS

| | | | |
|---|---|---|---|
| 4,599,342 A | 7/1986 | LaHann | |
| 5,198,346 A | 3/1993 | Ladner et al. | |
| 5,223,409 A | 6/1993 | Ladner et al. | |
| 5,429,939 A | 7/1995 | Misawa et al. | |
| 5,602,169 A | 2/1997 | Hewawasam et al. | |
| 5,741,691 A | 4/1998 | Arnold et al. | |
| 5,785,989 A | 7/1998 | Stanley et al. | |
| 5,789,166 A | 8/1998 | Bauer et al. | |
| 5,837,458 A | 11/1998 | Minshull et al. | |
| 5,945,325 A | 8/1999 | Arnold | |
| 5,965,408 A | 10/1999 | Short | |
| 6,090,604 A | 7/2000 | Golightly et al. | |
| 6,107,073 A | 8/2000 | Chen | |
| 6,316,216 B1 | 11/2001 | Ohto et al. | |
| 6,361,988 B1 | 3/2002 | Arnold | |
| 6,498,026 B2 | 12/2002 | Delagrave et al. | |
| 6,524,837 B1 | 2/2003 | Arnold | |
| 6,537,746 B2 | 3/2003 | Arnold et al. | |
| 6,643,591 B1 | 11/2003 | Korzekwa et al. | |
| 6,906,930 B2 | 5/2004 | Arnold et al. | |
| 6,794,168 B1 | 9/2004 | Wong et al. | |
| 6,902,918 B1 | 6/2005 | Arnold et al. | |
| 7,098,010 B1 | 8/2006 | Arnold et al. | |
| 7,115,403 B1 | 10/2006 | Arnold et al. | |
| 7,226,768 B2 * | 6/2007 | Farinas et al. ................ | 435/189 |
| 7,435,570 B2 | 10/2008 | Arnold et al. | |
| 7,465,567 B2 | 12/2008 | Cirino et al. | |
| 7,524,664 B2 | 4/2009 | Arnold et al. | |
| 7,691,616 B2 | 4/2010 | Farinas et al. | |
| 2001/0051855 A1 | 12/2001 | Wang et al. | |
| 2002/0045175 A1 | 4/2002 | Wang et al. | |
| 2002/0168740 A1 | 11/2002 | Chen | |
| 2003/0077795 A1 | 4/2003 | Wilson | |
| 2003/0077796 A1 | 4/2003 | Crotean | |
| 2003/0100744 A1 * | 5/2003 | Farinas et al. ................ | 536/23.2 |
| 2003/0215859 A1 * | 11/2003 | Affholter et al. ................ | 435/6 |
| 2005/0003389 A1 | 1/2005 | Wang et al. | |
| 2005/0037411 A1 | 2/2005 | Arnold et al. | |
| 2005/0059045 A1 | 3/2005 | Arnold et al. | |
| 2005/0059128 A1 | 3/2005 | Arnold et al. | |
| 2005/0202419 A1 | 9/2005 | Cirino et al. | |
| 2008/0057577 A1 | 3/2008 | Arnold et al. | |
| 2008/0248545 A1 | 10/2008 | Arnold et al. | |
| 2008/0268517 A1 | 10/2008 | Arnold et al. | |
| 2008/0293928 A1 | 11/2008 | Farinas et al. | |
| 2009/0061471 A1 | 3/2009 | Fasan et al. | |

(Continued)

FOREIGN PATENT DOCUMENTS

| | | |
|---|---|---|
| WO | 98/42832 A1 | 10/1998 |
| WO | 99/60096 A2 | 11/1999 |

(Continued)

OTHER PUBLICATIONS

Branden et al. Introduction to Protein Structure, Garland Publishing Inc., New York, p. 247, 1991.*

(Continued)

*Primary Examiner* — Yong Pak
(74) *Attorney, Agent, or Firm* — Joseph R. Baker, Jr.; Gavrilovich, Dodd & Lindsey LLP

(57) ABSTRACT

The disclosure relates to engineered P450 polypeptides and use of such polypeptides in chemoenzymatic methods to construct selectively protected carbohydrates, which are useful as building blocks for preparation of carbohydrate derivatives and oligosaccharides

14 Claims, 21 Drawing Sheets

(56) References Cited

U.S. PATENT DOCUMENTS

| | | | |
|---|---|---|---|
| 2009/0124515 | A1 | 5/2009 | Arnold et al. |
| 2009/0142821 | A1 | 6/2009 | Cirino et al. |
| 2009/0209010 | A1 | 8/2009 | Fasan et al. |
| 2009/0264311 | A1 | 10/2009 | Arnold et al. |
| 2009/0298148 | A1 | 12/2009 | Arnold et al. |

FOREIGN PATENT DOCUMENTS

| | | |
|---|---|---|
| WO | 00/06718 A2 | 2/2000 |
| WO | 00/31273 A2 | 6/2000 |
| WO | 01/61344 A1 | 8/2001 |
| WO | 01/62938 A2 | 8/2001 |
| WO | 02/083868 A2 | 10/2002 |
| WO | 03/008563 A2 | 1/2003 |
| WO | 03/091835 A2 | 11/2003 |
| WO | 03/101184 A2 | 12/2003 |
| WO | 2005/017105 A2 | 2/2005 |
| WO | 2005/017106 A2 | 2/2005 |
| WO | 2006/105082 A2 | 10/2006 |
| WO | 2008/016709 A3 | 2/2008 |
| WO | 2008/085900 A2 | 7/2008 |
| WO | 2008/098198 A2 | 8/2008 |
| WO | 2008/115844 A2 | 9/2008 |
| WO | 2008/118545 A2 | 10/2008 |
| WO | 2008/121435 A2 | 10/2008 |

OTHER PUBLICATIONS

Guo et al. Proc Natl Acad Sci USA. Jun. 22, 2004;101(25):9205-10.*
Abecassis et al., Nucleic Acids Res., 2000, vol. 28, E88.
Abecassis et al., "Design and characterization of a novel family-shuffling technology adapted to membrane enzyme: application to P450s involved in xenobiotic metabolism," adv. Exp. Med. Biol. 500, 2001, pp. 319-322.
Abecassis et al., "Exploration of natural and artificial sequence spaces: Towards a functional remodeling of membrane-bound cytochrome P450," Biocatal. Biotransform, 2003, vol. 21, No. 2, pp. 55-66.
Abkevich et al., "Impact of Local and Non-Local interactions on Thermodynamics and Kinetics of Protein Folding", J. Mol. Biol. 1995, 252, pp. 460-471.
Achutamarthy, Ponnathapu, International Search Report, Date of Mailing of Search: Sep. 25, 2007, International Application No. PCT/US04/18832.
Adam et al., "Microbial Asymmetric CH Oxidations of Simple Hydrocarbons: A Novel Monooxygenase Activity of the Topsoil Microorganism Bacillus megaterium," Eur. J. Org. Chem., 2000, pp. 2923-2926, Wiley-VCH Verlag GmbH, Weinheim, Germany.
Affholter et al., "Engineering a Revolution", Chembytes e-zine, Apr. 1999, [Website] 10 pages, printed Apr. 14, 2004, http://www.chemsoc.org/chembytes/ezine/1999/arnold_apr99.htm.
Aisaka et al., "Production of Galactose Oxidase by Gibberella fujikuroi," Agric. Biol. Chem., 1981, pp. 2311-2316, 45 (10), Amaral et al., "Galactose Oxidase of Polyporus circinatus1-4," Methods in Enzymology, Carbohydrate Metabolism, 1966, pp. 87-92, vol. 9, Academic Press Inc., New York, NY, USA.
Amaral et al., "Galactose Oxidase of Polyporus circinatus1-4," Methods in Enzymology, Carbohydrate Metabolism, 1966, pp. 87-92, vol. 9, Academic Press Inc., New York, NY, USA.
Anfinsen, "Principles that Govern the Folding of Protein Chains," Science, Jul. 20, 1973, pp. 223-230, vol. 181, No. 4096, American Asso for the Advancement of Science, Washington, DC, USA.
Appel et al., "A P450 BM-3 mutant hydroxylates alkanes, cycloalkanes, arenas and heteroarenes," Journal of Biotechnology, 2001, pp. 167-171, Elsevier Science B.V.
Arnold, "Engineering proteins for nonnatural environments," The FASEB Journal, Jun. 1993, pp. 744-749, vol. 7, No. 6, FASEB, Bethesda, MD, USA.
Arnold, Frances H., "Design by Directed Evolution," Accounts of Chemical Research, 1998, vol. 31, pp. 125-131.
Arnold et al., "Directed Evolution of Biocatalysts," Current Opinion in Chem. Biology, Current Biology Ltd, London GB 3(1):54-59, Feb. 1999.
Arnold et al., "Optimizing Industrial Enzymes by Directed Evolution," Advances in Biochemical Engineering/Biotechnology, 1997, pp. 1-14, vol. 58, Springer-Verlag, Berlin, Germany.
Arnold, "Advances in Protein Chemistry", Adv. Protein Chem., 2000, 55: ix-xi.
Arnold, "Combinatorial and Computational Challenges for Biocatalyst design", Nature, 2001, 409(6817), pp. 253-257.
Arnold & Wintrode, Enzymes, Directed Evolution, in Encyclopedia of bioprocess technology: fermentation, biocatalysis, and bioseparation, 1999, 2, 971.
Arts et al., "Hydrogen Peroxide and Oxygen in Catalytic Oxidation of Carbohydrates and Related Compounds," Synthesis Journal of Synthetic Organic Chemistry, Jun. 1997, pp. 597-613.
Ashraf et al., "Bacterial oxidation of propane," FEMS Microbiology Letters, 1994, pp. 1-6, Federation of European Microbiological Societies, Elsevier.
Aust, S. D., Redox Report, 1999, 4:195-7.
Avigad, "Oxidation Rates of Some Desialylated Glycoproteins by Galactose Oxidase," Archives of Biochemistry and Biophysics, Jun. 1985, pp. 531-537, vol. 239, No. 2, Academic Press, Inc.
Avigad, "An NADH Coupled Assay System for Galactose Oxidase," Analytical Biochemistry, 1978, pp. 470-476, 86, Academic Press, Inc.
Avigad et al., "The D-Galactose Oxidase of Polyporus circinatus," Journal of Biological Chemistry, Sep. 1962, pp. 2736-2743, vol. 237, No. 9, American Society of Biological Chemists, Baltimore, MD, USA.
Ayala, et al., "Enzymatic Activation of alkanes: constraints and prospective," Applied Catalysts A: General, 2004, pp. 1-13, vol. 272.
Barnes, "Maximizing Expression of Eukaryotic Cytochrome P450s in *Escherichia coli*," Methods in Enzymology, Cytochrome P450, Part B, 1996, pp. 3-14, vol. 272, Academic Press, Inc., San Diego, CA, USA.
Barnes, H. J., et al., "Expression and enzymatic activity of recombinant cytochrome P450 17 a-hydroxylase in *Escherichia coli,*" Proce. Natl Acad. Sci USA 1991; 88:5597-601.
Baron et al., "Structure and Mechanism of Galactose Oxidase," The Journal of Biological Chemistry, Sep. 23, 1994, pp. 25095-25105, vol. 269, No. 38, American Soc for Biochemistry and Molecular Biology.
Bell et al., "Butane and propane oxidation by engineered cytochromes P450(cam)," Chemical Communications, 2002, vol. 5, pp. 490-491.
Bell et al., "Engineering Cytochrome P450cam into an alkane hydroxylase," Dalton Transactions, 2003, vol. 11, pp. 2133-2140.
Boddupalli et al., "Fatty Acid Monooxygenation by P450BM-3: Product Identification and Proposed Mechanisms for the Sequential Hydroxylation Reactions," Archives of Biochemistry and Biophysics, Jan. 1992, pp. 20-28, vol. 292, No. 1, Academic Press, Inc.
Boddupalli et al., "Fatty Acid Monooxygenation by Cytochrome P-450BM-3," The Journal of Biological Chemistry, 1990, pp. 4233-4239, The American Society for Biochemistry and Molecular Biology.
Borman et al., "Kinetic studies on the reactions of Fusarium galactose oxidase with five different substrates in the presence of dioxygen," Journal of Biological Inorganic Chemistry, 1997, pp. 480-487, Society of Biological Inorganic Chemistry.
Capdevila, J. et al., "The Highly Stereoselective Oxidation of Polyunsaturated Fatty Acids by Cytochrome P450BM-3," The Journal of Biological Chemistry, Sep. 13, 1996, pp. 22663-22671, vol. 271, No. 37, The American Society for Biochemistry and Molecular Biology, Inc.
Carmichael, A. et al., "Protein engineering of *Bacillus megaterium* CYP102," Eur. J. Biochem., 2001, pp. 3117-3125, vol. 268, FEBS.
Chen et al., "Stereospecific alkane hydroxylation by non-heme iron catalysts: mechanistic evidence for an Fe-V = 0 active species," Journal of the American Chemical Society, 2001, vol. 123, No. 26, pp. 6327-6337.

(56) References Cited

OTHER PUBLICATIONS

Cirino et al., "Exploring the diversity of heme enzymes through directed evolution," in Directed Molecular Evolution of Proteins, 2002, pp. 215-243, S. Brakmann and K. Johnsson, eds., (Germany: Wiley-VCH).

Cirino & Arnold, "Protein engineering of oxygenases for biocatalysts", Current Opinion in Chemical Biology, 2002, vol. 6, pp. 130-135.

Cirino & Arnold, "Regioselectivity and Activity of Cytochrome P450 BM-3 and Mutant F87A in Reactions Driven by Hydrogen Peroxide", Adv. Synth. Catal., 2002, vol. 344, No. 9, pp. 932-937.

Dahlhoff, W. et al., "L-Glucose or D-gluco-Hexadialdose from D-Glucurono-6,3-lactone by Controlled Reductions," Angew. Chem. Int. Ed. Engl., 1980, pp. 546-547, 19 No. 7, Verlag Chemie, GmbH, Weinheim, Germany.

De Visser et al., "Hydrogen bonding modulates the slectivity of enzymatic oxidation by P450: Chameleon oxidant behavior by compound I," Angewandte Chemie-International Edition, 2002, vol. 41, No. 11, pp. 1947.

De Visser et al., "What factors affect the regioselectivity of oxidation by cytochrome P450? A DFT study of allylic hydroxylation and double bond epoxidation in a model reaction," Journal of the American Chemical Society, 2002, vol. 124, No. 39, pp. 11809-11826.

Deacon, S. et al., "Enhanced Fructose Oxidase Activity in a Galactose Oxidase Variant," ChemBioChem: A European Journal of Chemical Biology, 2004, pp. 971-979, 5, Wiley-VCH Verlag GmbH & Co., Weinheim, Germany.

Farinas, E., et al., "Directed Evolution of a Cytochrome P450 Monooxygenase for Alkane Oxidation," Adv. Synth. Catal., 2001, pp. 601-606, vol. 343, No. 6-7.

Fruetel, J., et al., "Relationship of Active Site Topology to Substrate Specificity for Cytochrome P450terp (CYP108)," The Journal of Biological Chemistry, Nov. 18, 1994, pp. 28815-28821, vol. 269, No. 46, The American Society for Biochemistry and Molecular Biology, Inc.

Gotoh, Cytochrome P450, 2nd Edition, 1993, pp. 255-272.

Govindaraj and Poulos; "Role of the linker region connecting the reductase and heme domains in cytochrome P450BM-3"; Biochemistry; vol. 34, No. 35, Abstract, 1995.

Govindaraj and Poulos; "Role of the linker region connecting the reductase and heme domains in cytochrome P450BM-3"; Biochemistry; vol. 34, No. 35, 1995, pp. 11221-11226.

Graham-Lorence, S., et al., "An Active Site Substitution, F87V, Converts Cytochrome P450 BM-3 into a Regio-and Stereoselective (14S,15R)-Arachidonic Acid Epoxygenase," The Journal of Biological Chemistry, Jan. 10, 1997, pp. 1127-1135, vol. 272, No. 2, The American Society for Biochemistry and Molecular Biology, Inc.

Groves, John et al., "Models and Mechanisms of Cytochrome P450 Action," Cytochrome P450: Structure, Mechanisms, and Biochemistry, 2nd Edition, New York, 1995, pp. 3-48.

Guengerich, F., et al., "Purification of Functional Recombinant P450s from Bacteria," Methods in Enzymology, 1996, pp. 35-44, vol. 272, Academic Press, Inc.

Kahn et al., "Feasibility and review of anomalous X-ray diffraction at long wavelengths in materials research and protein crystallography", J. Synchrotron Radiat., 2000, 7, pp. 131-138.

Kuchner, O. et al., "Directed evolution of enzyme catalysts," Trends in Biotechnology, Dec. 1997, pp. 523-530, vol. 15, Elsevier Science Ltd.

Landwehr, et al., "Diversification of Catalytic Function in a Synthetic Family of Chimeric Cytochrome P450s", Chemistry and Biology, Current Biology, vol. 14, No. 3, Mar. 23, 2007, pp. 269-278.

Lewis, D., "P450 Substrate Specificity and Metabolism," Cytochrome P450: Structure, Function and Mechanism, Aug. 2001, pp. 115-166, Taylor & Francis Publishers.

Lewis, D. F. W., et al., "Molecular modeling of CYP1 family enzymes CYP1A1, CYP1A2, CYP1A6 and CYP1B1 based on sequence homology with CYP102," Toxicology, 139, 1999, pp. 53-79.

Li, Qing-Shan, J. Ogawa, R. D. Schmid, and S. Shimizu, "Engineering Cytochrome P450 BM-3 for Oxidation of Polycyclic Aromatic Hydrocarbon" Appl. and Env. Microbiol. Dec. 2001, 67(10): 5735-5739.

Li et al., "Directed evolution of the fatty-acid hydroxylase P450 BM-3 into an indole-hydroxylating catalyst," Chemistry 2000, vol. 6, pp. 1531-1536.

Li et al., "residue size at position 87 of cytochrome P450 BM-3 determines its stereo selectivity in propylbenzene and 3-chlorostyrene oxidation," FEBS Lett 508, 2001, pp. 249-252.

Li, H. et al., "Characterization of Recombinant *Bacillus megaterium* Cytochrome P-450BM-3 and Its Two Functional Domains", Journal of Biological Chemistry, vol. 266, No. 18, 1991:266: pp. 11909-11914.

Li, Q. S., et al.; "Critical Role of the residue size at position 87 in H2)2-dependent substrate hydroxylation activity in h2o2 inactivation of cytochrome P450-BM-3"; Biochem, Biophysics Res Commun. vol. 280, No. 5, Abstract, 2001.

Li, et al., "Critical Role of the Residue Size at Position 87 in H2O2-Dependent Substrate Hydroxylation Activity and H2O2 Inactivation of Cytochrome P450BM-3", Biochemical and Biophysical Research Communications, 2001, vol. 280, pp. 1258-1261.

Miles, Caroline S. et al., "Protein engineering of cytochromes P-450," Biochimica et Biophysica Acta 1543, 2000, pp. 383-407.

Miura, Yoshiro, et al., "ω-1, ω-2 and ω-3 hydroxylation of long-chain fatty acids, amides and alcohols by a soluble enzyme system from *Bacillus megaterium*," Biochimica et Biophysica Acta 388, 1975, pp. 305-317.

Nelson, D., "Appendix A—Cytochrome P450 Nomenclature and Alignment of Selected Sequences," Cytochrome P450: Structure, Mechanism, and Biochemistry, Second Ed., 1995, pp. 575-606, Plenum Press, NY.

Noble, M. et al., "Roles of key active-site residues in flavocytochrome P450 BM3," Biochem. J., 1999, pp. 371-379, 339, Biochemical Society.

Oliver, C. et al., "Engineering the substrate specificity of *Bacillus megaterium* cytochrome P-450 BM3: hydroxylation of alkyl trimethylammonium compounds," Biochem. J., 1997, pp. 537-544, 327, The Biochemical Society, London, England.

Oliver, C. F., et al., "A single Mutation in Cytochrome P450 BM3 Changes Substrate Orientation in a Catalytic Intermediate and the Regiospecificity of Hydroxylation", Biochemistry 1997; 36:1567-72.

Ost, T. et al., "Rational re-design of the substrate binding site of flavocytochrome P450 BM3," FEBS Letters, 2000, pp. 173-177, 486, Elsevier Science B.V.

Ost, T. W., et al. "Rational re-design of the substrate binding site of flavocytochrome P450 BM3"; FEBS Lett., vol. 486, No. 2, Abstract 2000.

Otey et al., "Functional evolution and structural conservation in chimeric cytochromes P450: Calibrating a structure-guided approach," Chemistry and Biology, 2004, vol. 11, pp. 309-318.

Otey, Christopher R. et al., "Structure-guided recombination creates an artificial family of cytochromes P450", PLOS Biology, vol. 4, No. 5, May 2006, pp. 789-798.

Peters, Matthew W., "Regio- and Enantioselective Alkane Hydroxylation with Engineered Cytochromes P450 BM-3," J. Am. Chem. Soc., vol. 125, 2003, pp. 13442-13450.

Peterson, J. et al., "Chapter 5—Bacterial P450s—Structural Similarities and Functional Differences", Cytochrome P450: Structure, Mechanism, and Biochemistry, Second Ed., 1995, pp. 151-180.

Peterson et al., "The many faces of P450s and their structural and functional implications," Sixth International Symposium on Cytochrome P450 Biodiversity: University of California, Los Angels, 2002, p. 26.

Petrounia, Ioanna and F. H. Arnold "Designed evolution of enzymatic properties," Current Opinion in Biotech., 11 (4): 325-330, Aug. 2000.

Pompon, et al., "Protein engineering by cDNA recombination in yeasts: shuffling of mammalian cytochrome P-450 functions," Gene, 1989, vol. 83, pp. 15-24.

Roberts, "The power of evolution: accessing the synthetic potential of P450s", Chemistry & Biology, 1999, vol. 6, No. 10, pp. R269-R272.

(56) References Cited

OTHER PUBLICATIONS

Root, R., et al., "Enzymatic Synthesis of Unusual Sugars: Galactose Oxidase Catalyzed Stereospecific Oxidation of Polyols," Journal of the American Chemical Society, 1985, pp. 2997-2999, vol. 107, No. 10, American Chemical Society.

Scheller, U., et al., "Characterization of the n-Alkane and Fatty Acid Hydroxylating Cytochrome P450 Forms 52A3 and 52A4," Archives of Biochemistry and Biophysics, Apr. 15, 1996, pp. 245-254, vol. 328, No. 2, Academic Press, Inc.

Schmid, A., et al., "Industrial Biocatalysis Today and Tomorrow," Nature, Jan. 11, 2001, pp. 258-268, vol. 409, Macmillian Magazines Ltd.

Schneider, S., et al., "Controlled Regioelectivity of Fatty Acid Oxidation by Whole Cells Producing Cytochrome P450BM-3 Monooxygenase Under Varied Dissolved Oxygen Concentrations," Biotechnology and Bioengineering, Aug. 5, 1999, pp. 333-341, vol. 64, No. 3, John Wiley & Sons, Inc.

Schneider, et al., "Production of chiral hydroxyl long chain fatty acids by whole cells producing cytochrome P450 (BM-3) monooxygenase," Tetrahedron Asymetry, 1998, Vool. 9, No. 16, pp. 2833-2844.

Stevenson, J., et al., "The Catalytic Oxidation of Linear and Branched Alkanes by Cytochrome P450cam," J. Am. Chem. Soc., 1996, pp. 12846-12847, vol. 118, No. 50, American Chemical Society.

Stevenson et al., "Engineering molecular recognition in alkane oxidation catalysed by cytochrome P450(cam)", New Journal of Chemistry, 1998, vol. 22, No. 6, pp. 551-552.

Tsotsou et al., "High throughput assay for chytochroms P450BM3 for screening libraries of substrates and combinatorial mutants," Biosensors and Bioelectronics, 2002, vol. 17, No. 1-2, pp. 119-131.

Urlacher et al., "Biotransformations using prokaryotic P450 monooxygenases," Current Opinion in Biotechnology, 2002, vol. 13, pp. 557-564.

Urlacher et al., "Protein Engineering of cytochrome P450 monooxygenase from *Bacillus megaterium*." Methods in Enzymology, pp. 208-224, vol. 388, 2004.

Van Deurzen M. P. J., et al., "Selective Oxidations Catalyzed by Peroxidases", Tetrahedron Report No. 427, vol. 53, No. 39, 1997; pp. 13183-13220.

Vidakovic, Momcilo et al., "Understanding the role of the essential Asp251 in cytochrome P450cam using site-directed mutagenesis, crystallography, and kinetic solvent isotope effect", Biochemistry, vol. 37, No. 26, Jun. 30, 1998, pp. 9211-9219, XP002187779.

Wachter, R., et al., "Molecular Modeling Studies on Oxidation of Hexopyranoses by Galactose Oxidase. An Active Site Topology Apparently Designed to Catalyze Radical Reactions, Either Concerted or Stepwise," Journal of the American Chemical Society, Mar. 9, 1996, pp. 2782-2789, vol. 118, No. 9.

Yeom, H., et al., "Oxygen Activation by Cytochrome P450BM-3: Effects of Mutating an Active Site Acidic Residue," Archieves of Biochemistry and Biophysics, Jan. 15, 1997, pp. 209-216, vol. 337, No. 2, Academic Press.

Yeom, Sligar H., et al., "The role of Thr268 in oxygen activation of cytochrome P450BM-3" Biochemistry, vol. 34, No. 45., Abstract 1995.

Zhao, H. et al., "Methods for Optimizing Industrial Enzymes by Directed Evolution", Manual of Industrial Microbiology and Biotechnology, 2nd Edition, 1999, pp. 597-604.

Zimmer, T., et al., "The CYP52 Multigene Family of *Candida maltosa* Encodes Functionally Diverse n-Alkane-Inducible Cytochromes P450," Biochemical and Biophysical Research Communications, 1996, pp. 784-789, vol. 224, No. 3, Academic Press, Inc.

* cited by examiner

Sequence no.1 (9-10A)
TIKEMPQPKTFGELKNLPLLNTDKPVQALMKIADELGEIFKFEAPGCVTRYLSSQRLIKEACDESRFD
KNLSQALKFARDFAGDGLFTSWTHEINWKKAHNILLPSFSQQAMKGYHAMMVDIAVQLVQKWERLNAD
EHIEVSEDMTRLTLDTIGLCGFNYRFNSFYRDQPHPFIISMVRALDEVMNKLQRANPDDPAYDENKRQ
CQEDIKVMNDLVDKIIADRKARGEQSDDLLTQMLNGKDPETGEPLDDGNISYQIITFLIAGHETTSGL
LSFALYFLVKNPHVLQKVAEEAARVLVDPVPSYKQVKQLKYVGMVLNEALRLWPTAPAFSLYAKEDTV
LGGEYPLEKGDEVMVLIPQLHRDKTIWGDDVEEFRPERFENPSAIPQHAFKPFGNGQRACIGQQFALH
EATLVLGMMLKHFDFEDHTNYELDIKETLTLKPEGFVVKAKSKKIPLGGIPSPSTEQSAKKVRKKAEN
AHNTPLLVLYGSNMGTAEGTARDLADIAMSKGFAPQVATLDSHAGNLPREGAVLIVTASYNGHPPDNA
KQFVDWLDQASADEVKGVRYSVFGCGDKNWATTYQKVPAFIDETLAAKGAENIADRGEADASDDFEGT
YEEWREHMWSDVAAYFNLDIENSEDNKSTLSLQFVDSAADMPLAKMHGAFSTNVVASKELQQPGSARS
TRHLEIELPKEASYQEGDHLGVIPRNYEGIVNRVTARFGLDASQQIRLEAEEEKLAHLPLAKTVSVEE
LLQYVELQDPVTRTQLRAMAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAELQEGDTITCFISTP
QSEFTLPKDPETPLIMVGPGTGVAPFRGFVQARKQLKEQGQSLGEAHLYFGCRSPHEDYLYQEELENA
QSEGIITLHTAFSRMPNQPKTYVQHVMEQDGKKLIELLDQGAHFYICGDGSQMAPAVEATLMKSYADV
HQVSEADARLWLQQLEEKGRYAKDVWAG Sequence no.2 (9-10A F87A)
TIKEMPQPKTFGELKNLPLLNTDKPVQALMKIADELGEIFKFEAPGCVTRYLSSQRLIKEACDESRFD
KNLSQALKFARDFAGDGLATSWTHEINWKKAHNILLPSFSQQAMKGYHAMMVDIAVQLVQKWERLNAD
EHIEVSEDMTRLTLDTIGLCGFNYRFNSFYRDQPHPFIISMVRALDEVMNKLQRANPDDPAYDENKRQ
CQEDIKVMNDLVDKIIADRKARGEQSDDLLTQMLNGKDPETGEPLDDGNISYQIITFLIAGHETTSGL
LSFALYFLVKNPHVLQKVAEEAARVLVDPVPSYKQVKQLKYVGMVLNEALRLWPTAPAFSLYAKEDTV
LGGEYPLEKGDEVMVLIPQLHRDKTIWGDDVEEFRPERFENPSAIPQHAFKPFGNGQRACIGQQFALH
EATLVLGMMLKHFDFEDHTNYELDIKETLTLKPEGFVVKAKSKKIPLGGIPSPSTEQSAKKVRKKAEN
AHNTPLLVLYGSNMGTAEGTARDLADIAMSKGFAPQVATLDSHAGNLPREGAVLIVTASYNGHPPDNA
KQFVDWLDQASADEVKGVRYSVFGCGDKNWATTYQKVPAFIDETLAAKGAENIADRGEADASDDFEGT
YEEWREHMWSDVAAYFNLDIENSEDNKSTLSLQFVDSAADMPLAKMHGAFSTNVVASKELQQPGSARS
TRHLEIELPKEASYQEGDHLGVIPRNYEGIVNRVTARFGLDASQQIRLEAEEEKLAHLPLAKTVSVEE
LLQYVELQDPVTRTQLRAMAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAELQEGDTITCFISTP
QSEFTLPKDPETPLIMVGPGTGVAPFRGFVQARKQLKEQGQSLGEAHLYFGCRSPHEDYLYQEELENA
QSEGIITLHTAFSRMPNQPKTYVQHVMEQDGKKLIELLDQGAHFYICGDGSQMAPAVEATLMKSYADV
HQVSEADARLWLQQLEEKGRYAKDVWAG Sequence no.3 (9-10A F87V)
TIKEMPQPKTFGELKNLPLLNTDKPVQALMKIADELGEIFKFEAPGCVTRYLSSQRLIKEACDESRFD
KNLSQALKFARDFAGDGLVTSWTHEINWKKAHNILLPSFSQQAMKGYHAMMVDIAVQLVQKWERLNAD
EHIEVSEDMTRLTLDTIGLCGFNYRFNSFYRDQPHPFIISMVRALDEVMNKLQRANPDDPAYDENKRQ
CQEDIKVMNDLVDKIIADRKARGEQSDDLLTQMLNGKDPETGEPLDDGNISYQIITFLIAGHETTSGL
LSFALYFLVKNPHVLQKVAEEAARVLVDPVPSYKQVKQLKYVGMVLNEALRLWPTAPAFSLYAKEDTV
LGGEYPLEKGDEVMVLIPQLHRDKTIWGDDVEEFRPERFENPSAIPQHAFKPFGNGQRACIGQQFALH
EATLVLGMMLKHFDFEDHTNYELDIKETLTLKPEGFVVKAKSKKIPLGGIPSPSTEQSAKKVRKKAEN
AHNTPLLVLYGSNMGTAEGTARDLADIAMSKGFAPQVATLDSHAGNLPREGAVLIVTASYNGHPPDNA
KQFVDWLDQASADEVKGVRYSVFGCGDKNWATTYQKVPAFIDETLAAKGAENIADRGEADASDDFEGT
YEEWREHMWSDVAAYFNLDIENSEDNKSTLSLQFVDSAADMPLAKMHGAFSTNVVASKELQQPGSARS
TRHLEIELPKEASYQEGDHLGVIPRNYEGIVNRVTARFGLDASQQIRLEAEEEKLAHLPLAKTVSVEE
LLQYVELQDPVTRTQLRAMAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAELQEGDTITCFISTP
QSEFTLPKDPETPLIMVGPGTGVAPFRGFVQARKQLKEQGQSLGEAHLYFGCRSPHEDYLYQEELENA
QSEGIITLHTAFSRMPNQPKTYVQHVMEQDGKKLIELLDQGAHFYICGDGSQMAPAVEATLMKSYADV
HQVSEADARLWLQQLEEKGRYAKDVWAG

FIGURE 13A

Sequence no.4 (9-10A F87I)
TIKEMPQPKTFGELKNLPLLNTDKPVQALMKIADELGEIFKFEAPGCVTRYLSSQRLIKEACDESRFD
KNLSQALKFARDFAGDGLITSWTHEINWKKAHNILLPSFSQQAMKGYHAMMVDIAVQLVQKWERLNAD
EHIEVSEDMTRLTLDTIGLCGFNYRFNSFYRDQPHPFIISMVRALDEVMNKLQRANPDDPAYDENKRQ
CQEDIKVMNDLVDKIIADRKARGEQSDDLLTQMLNGKDPETGEPLDDGNISYQIITFLIAGHETTSGL
LSFALYFLVKNPHVLQKVAEEAARVLVDPVPSYKQVKQLKYVGMVLNEALRLWPTAPAFSLYAKEDTV
LGGEYPLEKGDEVMVLIPQLHRDKTIWGDDVEEFRPERFENPSAIPQHAFKPFGNGQRACIGQQFALH
EATLVLGMMLKHFDFEDHTNYELDIKETLTLKPEGFVVKAKSKKIPLGGIPSPSTEQSAKKVRKKAEN
AHNTPLLVLYGSNMGTAEGTARDLADIAMSKGFAPQVATLDSHAGNLPREGAVLIVTASYNGHPPDNA
KQFVDWLDQASADEVKGVRYSVFGCGDKNWATTYQKVPAFIDETLAAKGAENIADRGEADASDDFEGT
YEEWREHMWSDVAAYFNLDIENSEDNKSTLSLQFVDSAADMPLAKMHGAFSTNVVASKELQQPGSARS
TRHLEIELPKEASYQEGDHLGVIPRNYEGIVNRVTARFGLDASQQIRLEAEEEKLAHLPLAKTVSVEE
LLQYVELQDPVTRTQLRAMAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAELQEGDTITCFISTP
QSEFTLPKDPETPLIMVGPGTGVAPFRGFVQARKQLKEQGQSLGEAHLYFGCRSPHEDYLYQEELENA
QSEGIITLHTAFSRMPNQPKTYVQHVMEQDGKKLIELLDQGAHFYICGDGSQMAPAVEATLMKSYADV
HQVSEADARLWLQQLEEKGRYAKDVWAG Sequence no.5 (9-10A A82L)
TIKEMPQPKTFGELKNLPLLNTDKPVQALMKIADELGEIFKFEAPGCVTRYLSSQRLIKEACDESRFD
KNLSQALKFARDFLGDGLFTSWTHEINWKKAHNILLPSFSQQAMKGYHAMMVDIAVQLVQKWERLNAD
EHIEVSEDMTRLTLDTIGLCGFNYRFNSFYRDQPHPFIISMVRALDEVMNKLQRANPDDPAYDENKRQ
CQEDIKVMNDLVDKIIADRKARGEQSDDLLTQMLNGKDPETGEPLDDGNISYQIITFLIAGHETTSGL
LSFALYFLVKNPHVLQKVAEEAARVLVDPVPSYKQVKQLKYVGMVLNEALRLWPTAPAFSLYAKEDTV
LGGEYPLEKGDEVMVLIPQLHRDKTIWGDDVEEFRPERFENPSAIPQHAFKPFGNGQRACIGQQFALH
EATLVLGMMLKHFDFEDHTNYELDIKETLTLKPEGFVVKAKSKKIPLGGIPSPSTEQSAKKVRKKAEN
AHNTPLLVLYGSNMGTAEGTARDLADIAMSKGFAPQVATLDSHAGNLPREGAVLIVTASYNGHPPDNA
KQFVDWLDQASADEVKGVRYSVFGCGDKNWATTYQKVPAFIDETLAAKGAENIADRGEADASDDFEGT
YEEWREHMWSDVAAYFNLDIENSEDNKSTLSLQFVDSAADMPLAKMHGAFSTNVVASKELQQPGSARS
TRHLEIELPKEASYQEGDHLGVIPRNYEGIVNRVTARFGLDASQQIRLEAEEEKLAHLPLAKTVSVEE
LLQYVELQDPVTRTQLRAMAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAELQEGDTITCFISTP
QSEFTLPKDPETPLIMVGPGTGVAPFRGFVQARKQLKEQGQSLGEAHLYFGCRSPHEDYLYQEELENA
QSEGIITLHTAFSRMPNQPKTYVQHVMEQDGKKLIELLDQGAHFYICGDGSQMAPAVEATLMKSYADV
HQVSEADARLWLQQLEEKGRYAKDVWAG Sequence no.6 (9-10A A82F)
TIKEMPQPKTFGELKNLPLLNTDKPVQALMKIADELGEIFKFEAPGCVTRYLSSQRLIKEACDESRFD
KNLSQALKFARDFFGDGLFTSWTHEINWKKAHNILLPSFSQQAMKGYHAMMVDIAVQLVQKWERLNAD
EHIEVSEDMTRLTLDTIGLCGFNYRFNSFYRDQPHPFIISMVRALDEVMNKLQRANPDDPAYDENKRQ
CQEDIKVMNDLVDKIIADRKARGEQSDDLLTQMLNGKDPETGEPLDDGNISYQIITFLIAGHETTSGL
LSFALYFLVKNPHVLQKVAEEAARVLVDPVPSYKQVKQLKYVGMVLNEALRLWPTAPAFSLYAKEDTV
LGGEYPLEKGDEVMVLIPQLHRDKTIWGDDVEEFRPERFENPSAIPQHAFKPFGNGQRACIGQQFALH
EATLVLGMMLKHFDFEDHTNYELDIKETLTLKPEGFVVKAKSKKIPLGGIPSPSTEQSAKKVRKKAEN
AHNTPLLVLYGSNMGTAEGTARDLADIAMSKGFAPQVATLDSHAGNLPREGAVLIVTASYNGHPPDNA
KQFVDWLDQASADEVKGVRYSVFGCGDKNWATTYQKVPAFIDETLAAKGAENIADRGEADASDDFEGT
YEEWREHMWSDVAAYFNLDIENSEDNKSTLSLQFVDSAADMPLAKMHGAFSTNVVASKELQQPGSARS
TRHLEIELPKEASYQEGDHLGVIPRNYEGIVNRVTARFGLDASQQIRLEAEEEKLAHLPLAKTVSVEE
LLQYVELQDPVTRTQLRAMAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAELQEGDTITCFISTP
QSEFTLPKDPETPLIMVGPGTGVAPFRGFVQARKQLKEQGQSLGEAHLYFGCRSPHEDYLYQEELENA
QSEGIITLHTAFSRMPNQPKTYVQHVMEQDGKKLIELLDQGAHFYICGDGSQMAPAVEATLMKSYADV
HQVSEADARLWLQQLEEKGRYAKDVWAG

FIGURE 13B

Sequence no.7 (9-10A F87V A82G A328V (12-10C))
TIKEMPQPKTFGELKNLPLLNTDKPVQALMKIADELGEIFKFEAPGCVTRYLSSQRLIKEACDESRFDKNLSQAL
KFARDFGGDGLVTSWTHEINWKKAHNILLPSFSQQAMKGYHAMMVDIAVQLVQKWERLNADEHIEVSEDMTRLTL
DTIGLCGFNYRFNSFYRDQPHPFIISMVRALDEVMNKLQRANPDDPAYDENKRQCQEDIKVMNDLVDKIIADRKA
RGEQSDDLLTQMLNGKDPETGEPLDDGNISYQIITFLIAGHETTSGLLSFALYFLVKNPHVLQKVAEEAARVLVD
PVPSYKQVKQLKYVGMVLNEALRLWPTVPAFSLYAKEDTVLGGEYPLEKGDEVMVLIPQLHRDKTIWGDDVEEFR
PERFENPSAIPQHAFKPFGNGQRACIGQQFALHEATLVLGMMLKHFDFEDHTNYELDIKETLTLKPEGFVVKAKS
KKIPLGGIPSPSTEQSAKKVRKKAENAHNTPLLVLYGSNMGTAEGTARDLADIAMSKGFAPQVATLDSHAGNLPR
EGAVLIVTASYNGHPPDNAKQFVDWLDQASADEVKGVRYSVFGCGDKNWATTYQKVPAFIDETLAAKGAENIADR
GEADASDDFEGTYEEWREHMWSDVAAYFNLDIENSEDNKSTLSLQFVDSAADMPLAKMHGAFSTNVVASKELQQP
GSARSTRHLEIELPKEASYQEGDHLGVIPRNYEGIVNRVTARFGLDASQQIRLEAEEEKLAHLPLAKTVSVEELL
QYVELQDPVTRTQLRAMAAKTVCPPHKVELEALLEKQAYKEQVLAKRLTMLELLEKYPACEMKFSEFIALLPSIR
PRYYSISSSPRVDEKQASITVSVVSGEAWSGYGEYKGIASNYLAELQEGDTITCFISTPQSEFTLPKDPETPLIM
VGPGTGVAPFRGFVQARKQLKEQGQSLGEAHLYFGCRSPHEDYLYQEELENAQSEGIITLHTAFSRMPNQPKTYV
QHVMEQDGKKLIELLDQGAHFYICGDGSQMAPAVEATLMKSYADVHQVSEADARLWLQQLEEKGRYAKDVWAG Sequence no.8 (9-10A F87V A82G A328L A78T (23-11B))
TIKEMPQPKTFGELKNLPLLNTDKPVQALMKIADELGEIFKFEAPGCVTRYLSSQRLIKEACDESRFDKNLSQAL
KFTRDFGGDGLVTSWTHEINWKKAHNILLPSFSQQAMKGYHAMMVDIAVQLVQKWERLNADEHIEVSEDMTRLTL
DTIGLCGFNYRFNSFYRDQPHPFIISMVRALDEVMNKLQRANPDDPAYDENKRQCQEDIKVMNDLVDKIIADRKA
RGEQSDDLLTQMLNGKDPETGEPLDDGNISYQIITFLIAGHETTSGLLSFALYFLVKNPHVLQKVAEEAARVLVD
PVPSYKQVKQLKYVGMVLNEALRLWPTLPAFSLYAKEDTVLGGEYPLEKGDEVMVLIPQLHRDKTIWGDDVEEFR
PERFENPSAIPQHAFKPFGNGQRACIGQQFALHEATLVLGMMLKHFDFEDHTNYELDIKETLTLKPEGFVVKAKS
KKIPLGGIPSPSTEQSAKKVRKKAENAHNTPLLVLYGSNMGTAEGTARDLADIAMSKGFAPQVATLDSHAGNLPR
EGAVLIVTASYNGHPPDNAKQFVDWLDQASADEVKGVRYSVFGCGDKNWATTYQKVPAFIDETLAAKGAENIADR
GEADASDDFEGTYEEWREHMWSDVAAYFNLDIENSEDNKSTLSLQFVDSAADMPLAKMHGAFSTNVVASKELQQP
GSARSTRHLEIELPKEASYQEGDHLGVIPRNYEGIVNRVTARFGLDASQQIRLEAEEEKLAHLPLAKTVSVEELL
QYVELQDPVTRTQLRAMAAKTVCPPHKVELEALLEKQAYKEQVLAKRLTMLELLEKYPACEMKFSEFIALLPSIR
PRYYSISSSPRVDEKQASITVSVVSGEAWSGYGEYKGIASNYLAELQEGDTITCFISTPQSEFTLPKDPETPLIM
VGPGTGVAPFRGFVQARKQLKEQGQSLGEAHLYFGCRSPHEDYLYQEELENAQSEGIITLHTAFSRMPNQPKTYV
QHVMEQDGKKLIELLDQGAHFYICGDGSQMAPAVEATLMKSYADVHQVSEADARLWLQQLEEKGRYAKDVWAG Sequence no.9 (21313313)
ETSPIPQPKTFGPLGNLPLIDKDKPTLSLIKLAEEQGPIFQIHTPAGTTIVVSGHELVKEVCDESRFDKNLSQAL
KFVRDFAGDGLATSWTHEKNWKKAHNILLPSFSQQAMKGYHAMMVDIATQLIQKWSRLNPNEEIDVADDMTRLTL
DTIGLCGFNYRFNSFYRDQPHPFITSMVRALDEAMNKLQRANPDDPAYDENKRQFQEDIKVMNDLVDRMIAERKA
NPDEIKDLLSLMLYAKDPVTGETLDDENIRYQIITFLIAGHETTSGLLSFAIYCLLTHPEKLKKAQEEADRVLTD
DTPEYKQIQQLKYIRMVLNETLRLYPTAPAFSLYAKEDTVLGGEYPLEKGDELMVLIPQLHRDKTIWGDDVEEFR
PERFENPSAIPQHAFKPFGNGQRACIGQQFALQEATMVLGLVLKHFELINHTGYELKIKEALTIKPDDFKITVKP
RKTAAINV Sequence no.10 (9-10A F87A C47R I94K)
TIKEMPQPKTFGELKNLPLLNTDKPVQALMKIADELGEIFKFEAPGRVTRYLSSQRLIKEACDESRFDKNLSQAL
KFARDFAGDGLATSWTHEKNWKKAHNILLPSFSQQAMKGYHAMMVDIAVQLVQKWERLNADEHIEVSEDMTRLTL
DTIGLCGFNYRFNSFYRDQPHPFIISMVRALDEVMNKLQRANPDDPAYDENKRQCQEDIKVMNDLVDKIIADRKA
RGEQSDDLLTQMLNGKDPETGEPLDDGNISYQIITFLIAGHETTSGLLSFALYFLVKNPHVLQKVAEEAARVLVD
PVPSYKQVKQLKYVGMVLNEALRLWPTAPAFSLYAKEDTVLGGEYPLEKGDEVMVLIPQLHRDKTIWGDDVEEFR
PERFENPSAIPQHAFKPFGNGQRACIGQQFALHEATLVLGMMLKHFDFEDHTNYELDIKETLTLKPEGFVVKAKS
KKIPLGGIPSPSTEQSAKKVRKKAENAHNTPLLVLYGSNMGTAEGTARDLADIAMSKGFAPQVATLDSHAGNLPR
EGAVLIVTASYNGHPPDNAKQFVDWLDQASADEVKGVRYSVFGCGDKNWATTYQKVPAFIDETLAAKGAENIADR
GEADASDDFEGTYEEWREHMWSDVAAYFNLDIENSEDNKSTLSLQFVDSAADMPLAKMHGAFSTNVVASKELQQP
GSARSTRHLEIELPKEASYQEGDHLGVIPRNYEGIVNRVTARFGLDASQQIRLEAEEEKLAHLPLAKTVSVEELL
QYVELQDPVTRTQLRAMAAKTVCPPHKVELEALLEKQAYKEQVLAKRLTMLELLEKYPACEMKFSEFIALLPSIR
PRYYSISSSPRVDEKQASITVSVVSGEAWSGYGEYKGIASNYLAELQEGDTITCFISTPQSEFTLPKDPETPLIM
VGPGTGVAPFRGFVQARKQLKEQGQSLGEAHLYFGCRSPHEDYLYQEELENAQSEGIITLHTAFSRMPNQPKTYV
QHVMEQDGKKLIELLDQGAHFYICGDGSQMAPAVEATLMKSYADVHQVSEADARLWLQQLEEKGRYAKDVWAG

FIGURE 13C

Sequence no.11 (9-10A F87A C47R I94K F81W A82S)
TIKEMPQPKTFGELKNLPLLNTDKPVQALMKIADELGEIFKFEAPGRVTRYLSSQRLIKEACDESRFDKNL
SQALKFARDWSGDGLATSWTHEKNWKKAHNILLPSFSQQAMKGYHAMMVDIAVQLVQKWERLNADEHIEVS
EDMTRLTLDTIGLCGFNYRFNSFYRDQPHPFIISMVRALDEVMNKLQRANPDDPAYDENKRQCQEDIKVMN
DLVDKIIADRKARGEQSDDLLTQMLNGKDPETGEPLDDGNISYQIITFLIAGHETTSGLLSFALYFLVKNP
HVLQKVAEEAARVLVDPVPSYKQVKQLKYVGMVLNEALRLWPTAPAFSLYAKEDTVLGGEYPLEKGDEVMV
LIPQLHRDKTIWGDDVEEFRPERFENPSAIPQHAFKPFGNGQRACIGQQFALHEATLVLGMMLKHFDFEDH
TNYELDIKETLTLKPEGFVVKAKSKKIPLGGIPSPSTEQSAKKVRKKAENAHNTPLLVLYGSNMGTAEGTA
RDLADIAMSKGFAPQVATLDSHAGNLPREGAVLIVTASYNGHPPDNAKQFVDWLDQASADEVKGVRYSVFG
CGDKNWATTYQKVPAFIDETLAAKGAENIADRGEADASDDFEGTYEEWREHMWSDVAAYFNLDIENSEDNK
STLSLQFVDSAADMPLAKMHGAFSTNVVASKELQQPGSARSTRHLEIELPKEASYQEGDHLGVIPRNYEGI
VNRVTARFGLDASQQIRLEAEEEKLAHLPLAKTVSVEELLQYVELQDPVTRTQLRAMAAKTVCPPHKVELE
ALLEKQAYKEQVLAKRLTMLELLEKYPACEMKFSEFIALLPSIRPRYYSISSSPRVDEKQASITVSVVSGE
AWSGYGEYKGIASNYLAELQEGDTITCFISTPQSEFTLPKDPETPLIMVGPGTGVAPFRGFVQARKQLKEQ
GQSLGEAHLYFGCRSPHEDYLYQEELENAQSEGIITLHTAFSRMPNQPKTYVQHVMEQDGKKLIELLDQGA
HFYICGDGSQMAPAVEATLMKSYADVHQVSEADARLWLQQLEEKGRYAKDVWAG Sequence no.12 (9-10A C47R A78L F87A I94K A180V V184T A330V (E12r12A87V))
TIKEMPQPKTFGELKNLPLLNTDKPVQALMKIADELGEIFKFEAPGRVTRYLSSQRLIKEACDESRFDKNL
SQALKFLRDFAGDGLVTSWTHEKNWKKAHNILLPSFSQQAMKGYHAMMVDIAVQLVQKWERLNADEHIEVS
EDMTRLTLDTIGLCGFNYRFNSFYRDQPHPFIISMVRALDETMNKLQRANPDDPAYDENKRQCQEDIKVMN
DLVDKIIADRKARGEQSDDLLTQMLNGKDPETGEPLDDGNISYQIITFLIAGHETTSGLLSFALYFLVKNP
HVLQKVAEEAARVLVDPVPSYKQVKQLKYVGMVLNEALRLWPTAPVFSLYAKEDTVLGGEYPLEKGDEVMV
LIPQLHRDKTIWGDDVEEFRPERFENPSAIPQHAFKPFGNGQRACIGQQFALHEATLVLGMMLKHFDFEDH
TNYELDIKETLTLKPEGFVVKAKSKKIPLGGIPSPSTEQSAKKVRKKAENAHNTPLLVLYGSNMGTAEGTA
RDLADIAMSKGFAPQVATLDSHAGNLPREGAVLIVTASYNGHPPDNAKQFVDWLDQASADEVKGVRYSVFG
CGDKNWATTYQKVPAFIDETLAAKGAENIADRGEADASDDFEGTYEEWREHMWSDVAAYFNLDIENSEDNK
STLSLQFVDSAADMPLAKMHGAFSTNVVASKELQQPGSARSTRHLEIELPKEASYQEGDHLGVIPRNYEGI
VNRVTARFGLDASQQIRLEAEEEKLAHLPLAKTVSVEELLQYVELQDPVTRTQLRAMAAKTVCPPHKVELE
ALLEKQAYKEQVLAKRLTMLELLEKYPACEMKFSEFIALLPSIRPRYYSISSSPRVDEKQASITVSVVSGE
AWSGYGEYKGIASNYLAELQEGDTITCFISTPQSEFTLPKDPETPLIMVGPGTGVAPFRGFVQARKQLKEQ
GQSLGEAHLYFGCRSPHEDYLYQEELENAQSEGIITLHTAFSRMPNQPKTYVQHVMEQDGKKLIELLDQGA
HFYICGDGSQMAPAVEATLMKSYADVHQVSEADARLWLQQLEEKGRYAKDVWAG Sequence no.13 (9-10A C47R A78L F87A I94K V184T I263M A330V (B1))
TIKEMPQPKTFGELKNLPLLNTDKPVQALMKIADELGEIFKFEAPGRVTRYLSSQRLIKEACDESRFDKNL
SQALKFLRDFAGDGLATSWTHEKNWKKAHNILLPSFSQQAMKGYHAMMVDIAVQLVQKWERLNADEHIEVS
EDMTRLTLDTIGLCGFNYRFNSFYRDQPHPFIISMVRALDETMNKLQRANPDDPAYDENKRQCQEDIKVMN
DLVDKIIADRKARGEQSDDLLTQMLNGKDPETGEPLDDGNISYQIITFLMAGHETTSGLLSFALYFLVKNP
HVLQKVAEEAARVLVDPVPSYKQVKQLKYVGMVLNEALRLWPTAPVFSLYAKEDTVLGGEYPLEKGDEVMV
LIPQLHRDKTIWGDDVEEFRPERFENPSAIPQHAFKPFGNGQRACIGQQFALHEATLVLGMMLKHFDFEDH
TNYELDIKETLTLKPEGFVVKAKSKKIPLGGIPSPSTEQSAKKVRKKAENAHNTPLLVLYGSNMGTAEGTA
RDLADIAMSKGFAPQVATLDSHAGNLPREGAVLIVTASYNGHPPDNAKQFVDWLDQASADEVKGVRYSVFG
CGDKNWATTYQKVPAFIDETLAAKGAENIADRGEADASDDFEGTYEEWREHMWSDVAAYFNLDIENSEDNK
STLSLQFVDSAADMPLAKMHGAFSTNVVASKELQQPGSARSTRHLEIELPKEASYQEGDHLGVIPRNYEGI
VNRVTARFGLDASQQIRLEAEEEKLAHLPLAKTVSVEELLQYVELQDPVTRTQLRAMAAKTVCPPHKVELE
ALLEKQAYKEQVLAKRLTMLELLEKYPACEMKFSEFIALLPSIRPRYYSISSSPRVDEKQASITVSVVSGE
AWSGYGEYKGIASNYLAELQEGDTITCFISTPQSEFTLPKDPETPLIMVGPGTGVAPFRGFVQARKQLKEQ
GQSLGEAHLYFGCRSPHEDYLYQEELENAQSEGIITLHTAFSRMPNQPKTYVQHVMEQDGKKLIELLDQGA
HFYICGDGSQMAPAVEATLMKSYADVHQVSEADARLWLQQLEEKGRYAKDVWAG

FIGURE 13D

SEQ ID NO: 15 (CYP102A1 from *Bacillus megaterium*)

```
   1 TIKEMPQPKT FGELKNLPLL NTDKPVQALM KIADELGEIF KFEAPGRVTR YLSSQRLIKE
  61 ACDESRFDKN LSQALKFVRD FAGDGLFTSW THEKNWKKAH NILLPSFSQQ AMKGYHAMMV
 121 DIAVQLVQKW ERLNADEHIE VPEDMTRLTL DTIGLCGFNY RFNSFYRDQP HPFITSMVRA
 181 LDEAMNKLQR ANPDDPAYDE NKRQFQEDIK VMNDLVDKII ADRKASGEQS DDLLTHMLNG
 241 KDPETGEPLD DENIRYQIIT FLIAGHETTS GLLSFALYFL VKNPHVLQKA AEEAARVLVD
 301 PVPSYKQVKQ LKYVGMVLNE ALRLWPTAPA FSLYAKEDTV LGGEYPLEKG DELMVLIPQL
 361 HRDKTIWGDD VEEFRPERFE NPSAIPQHAF KPFGNGQRAC IGQQFALHEA TLVLGMMLKH
 421 FDFEDHTNYE LDIKETLTLK PEGFVVKAKS KKIPLGGIPS PSTEQSAKKV RKKAENAHNT
 481 PLLVLYGSNM GTAEGTARDL ADIAMSKGFA PQVATLDSHA GNLPREGAVL IVTASYNGHP
 541 PDNAKQFVDW LDQASADEVK GVRYSVFGCG DKNWATTYQK VPAFIDETLA AKGAENIADR
 601 GEADASDDFE GTYEEWREHM WSDVAAYFNL DIENSEDNKS TLSLQFVDSA ADMPLAKMHG
 661 AFSTNVVASK ELQQPGSARS TRHLEIELPK EASYQEGDHL GVIPRNYEGI VNRVTARFGL
 721 DASQQIRLEA EEEKLAHLPL AKTVSVEELL QYVELQDPVT RTQLRAMAAK TVCPPHKVEL
 781 EALLEKQAYK EQVLAKRLTM LELLEKYPAC EMKFSEFIAL LPSIRPRYYS ISSSPRVDEK
 841 QASITVSVVS GEAWSGYGEY KGIASNYLAE LQEGDTITCF ISTPQSEFTL PKDPETPLIM
 901 VGPGTGVAPF RGFVQARKQL KEQGQSLGEA HLYFGCRSPH EDYLYQEELE NAQSEGIITL
 961 HTAFSRMPNQ PKTYVQHVME QDGKKLIELL DQGAHFYICG DGSQMAPAVE ATLMKSYADV
1021 HQVSEADARL WLQQLEEKGR YAKDVWAG
```

FIGURE 14A

SEQ ID NO: 17 (CYP102A2 from *Bacillus subtilis*, 59% identity to CYP102A1)

```
   1 KETSPIPQPK TFGPLGNLPL IDKDKPTLSL IKLAEEQGPI FQIHTPAGTT IVVSGHELVK
  61 EVCDEERFDK SIEGALEKVR AFSGDGLFTS WTHEPNWRKA HNILMPTFSQ RAMKDYHEKM
 121 VDIAVQLIQK WARLNPNEAV DVPGDMTRLT LDTIGLCGFN YRFNSYYRET PHPFINSMVR
 181 ALDEAMHQMQ RLDVQDKLMV RTKRQFRYDI QTMFSLVDSI IAERRANGDQ DEKDLLARML
 241 NVEDPETGEK LDDENIRFQI ITFLIAGHET TSGLLSFATY FLLKHPDKLK KAYEEVDRVL
 301 TDAAPTYKQV LELTYIRMIL NESLRLWPTA PAFSLYPKED TVIGGKFPIT TNDRISVLIP
 361 QLHRDRDAWG KDAEEFRPER FEHQDQVPHH AYKPFGNGQR ACIGMQFALH EATLVLGMIL
 421 KYFTLIDHEN YELDIKQTLT LKPGDFHISV QSRHQEAIHA DVQAAEKAAP DEQKEKTEAK
 481 GASVIGLNNR PLLVLYGSDT GTAEGVAREL ADTASLHGVR TKTAPLNDRI GKLPKEGAVV
 541 IVTSSYNGKP PSNAGQFVQW LQEIKPGELE GVHYAVFGCG DHNWASTYQY VPRFIDEQLA
 601 EKGATRFSAR GEGDVSGDFE GQLDEWKKSM WADAIKAFGL ELNENADKER STLSLQFVRG
 661 LGESPLARSY EASHASIAEN RELQSADSDR STRHIEIALP PDVEYQEGDH LGVLPKNSQT
 721 NVSRILHRFG LKGTDQVTLS ASGRSAGHLP LGRPVSLHDL LSYSVEVQEA ATRAQIRELA
 781 SFTVCPPHRR ELEELSAEGV YQEQILKKRI SMLDLLEKYE ACDMPFERFL ELLRPLKPRY
 841 YSISSSPRVN PRQASITVGV VRGPAWSGRG EYRGVASNDL AERQAGDDVV MFIRTPESRF
 901 QLPKDPETPI IMVGPGTGVA PFRGFLQARD VLKREGKTLG EAHLYFGCRN DRDFIYRDEL
 961 ERFEKDGIVT VHTAFSRKEG MPKTYVQHLM ADQADTLISI LDRGGRLYVC GDGSKMAPDV
1021 EAALQKAYQA VHGTGEQEAQ NWLRHLQDTG MYAKDVWAGI
```

FIGURE 14B

SEQ ID NO: 19 (CYP102A3 from *Bacillus subtilis*, 58% identity to CYP102A1)

```
   1 KQASAIPQPK TYGPLKNLPH LEKEQLSQSL WRIADELGPI FRFDFPGVSS VFVSGHNLVA
  61 EVCDEKRFDK NLGKGLQKVR EFGGDGLFTS WTHEPNWQKA HRILLPSFSQ KAMKGYHSMM
 121 LDIATQLIQK WSRLNPNEEI DVADDMTRLT LDTIGLCGFN YRFNSFYRDS QHPFITSMLR
 181 ALKEAMNQSK RLGLQDKMMV KTKLQFQKDI EVMNSLVDRM IAERKANPDE NIKDLLSLML
 241 YAKDPVTGET LDDENIRYQI ITFLIAGHET TSGLLSFAIY CLLTHPEKLK KAQEEADRVL
 301 TDDTPEYKQI QQLKYIRMVL NETLRLYPTA PAFSLYAKED TVLGGEYPIS KGQPVTVLIP
 361 KLHRDQNAWG PDAEDFRPER FEDPSSIPHH AYKPFGNGQR ACIGMQFALQ EATMVLGLVL
 421 KHFELINHTG YELKIKEALT IKPDDFKITV KPRKTAAINV QRKEQADIKA ETKPKETKPK
 481 HGTPLLVLFG SNLGTAEGIA GELAAQGRQM GFTAETAPLD DYIGKLPEEG AVVIVTASYN
 541 GAPPDNAAGF VEWLKELEEG QLKGVSYAVF GCGNRSWAST YQRIPRLIDD MMKAKGASRL
 601 TAIGEGDAAD DFESHRESWE NRFWKETMDA FDINEIAQKE DRPSLSITFL SEATETPVAK
 661 AYGAFEGIVL ENRELQTAAS TRSTRHIELE IPAGKTYKEG DHIGILPKNS RELVQRVLSR
 721 FGLQSNHVIK VSGSAHMAHL PMDRPIKVVD LLSSYVELQE PASRLQLREL ASYTVCPPHQ
 781 KELEQLVSDD GIYKEQVLAK RLTMLDFLED YPACEMPFER FLALLPSLKP RYYSISSSPK
 841 VHANIVSMTV GVVKASAWSG RGEYRGVASN YLAELNTGDA AACFIRTPQS GFQMPNDPET
 901 PMIMVGPGTG IAPFRGFIQA RSVLKKEGST LGEALLYFGC RRPDHDDLYR EELDQAEQDG
 961 LVTIRRCYSR VENEPKGYVQ HLLKQDTQKL MTLIEKGAHI YVCGDGSQMA PDVERTLRLA
1021 YEAEKAASQE ESAVWLQKLQ DQRRYVKDVW TGM
```

FIGURE 14C

```
SEQ15    1  ----------TIKEMPQPKTFGELKNLPLLNTDKPVQALMKIADELGEIFKFE    50
SEQ17   (1) ----------KETSPIPQPKTFGPLGNLPLIDKDKPTLSLIKLAEEQGPIFQIH
SEQ19   (1) ----------KQASAIPQPKTYGPLKNLPHLEKEQLSQSLWRIADELGPIERFD

SEQ15  (44) APGRVTRYLSSQRLIKFACDESREDKNISQAIKFVRDFAGDGLFTSWTHE    100
SEQ17  (45) TPAGTIIVVSGHELVKEVCDEERFDKSIEGALEKVRAFSGDGLFTSWTHE
SEQ19  (45) FPGVSSVFVSGHNLVAEVCDEKREDKNLGKGLQKVREFGGDGLFTSWTHE

SEQ15  (94) KNWKKAHNIILPSFSQQAMKGYHAMMVDIAVQLVQKWERLNADEHIEVPE    150
SEQ17  (95) PNWRKAHNIILMPTFSQRAMKDYHEKMVDIAVQLIQKWARLNPNEAVDVPG
SEQ19  (95) PNWQKAHRILLPSFSQKAMKGYHSMMLDIATQLIQKWSRLNPNEEIDVAD

SEQ15 (144) DMTRLTLDTIGLCGFNYRFNSFYRDQPHPFITSMVRALDEAMNKLQRANP    200
SEQ17 (145) DMTRLTLDTIGLCGFNYRFNSYYRETPHPFINSMVRALDEAMHQMRLDV
SEQ19 (145) DMTRLTLDTIGLCGFNYRFNSFYRDSQHPFITSMIRALKEAMNQSKRLGL
```

Figure 15A

```
                     201                                               250
SEQ15  (194)  DDPAYDENKRQFQEDIKVMNDIVDKIIAD---RKASGEQ-SDDLITHMLNG
SEQ17  (195)  QDKLMVRTKRQFRYDIQTMFSIVDSIHAE---RRANGDQDEKDIIARMLNV
SEQ19  (195)  QDKMMVKTKLQFQKDIEVMNSIVDRMIAE---RKANPDENIKDILSIMLYA 251                                               300
SEQ15  (241)  KDPETGEPLDDENIRYQIITFLIAGHETTSGLLSFALYFLVKNPHVLQKA
SEQ17  (243)  EDPETGEKLDDENIREQIITFLIAGHETTSGLLSFATYFLKHPDKLKKA
SEQ19  (243)  KDPVIGETLDDENIRYQIITFLIAGHETTSGLLSFAIYCLTHPEKLKKA 301                                               350
SEQ15  (291)  AEFAARVLVDPV-----PSYKQVKQLKYVGMVINEALRIWPTAPAFSLYAKE
SEQ17  (293)  YEEVDRVLTDAA-----PTYKQVLELTYIRMILNESLRIWPTAPAFSLYPKE
SEQ19  (293)  QEEADRVLTDDT-----PFYKQIQQLKYIRMVLNETLRLYPTAPAFSLYAKE 351                                               400
SEQ15  (338)  DTVLGGEYPLEKG-DELMVLIPQLHRDKTIWGDDVEEFRPERFE--NPSA
SEQ17  (340)  DTVLGGKFPITTN-DRISVLIPQLHRDRDAWGKDAEEFRPERFE--HQDQ
SEQ19  (340)  DTVLGGEYPISKG-QPVTVLIPKLHRDQNAWGPDAEDRPERFE--DPSS
```

Figure 15A (cont'd)

```
                401                                               450
SEQ15 (385)  IPQHAFKPFGNGQRACIGQQFALHEATLVLGMMIKHFDEDHTNYELDIK
SEQ17 (387)  VPHHAYKPFGNGQRACIGQQFALHEATLVLGMILKYFTLIDHENYELDIK
SEQ19 (387)  IPHHAYKPFGNGQRACIGMQFALQEATMVLGLVLKHFELINHTGYELKIK 451                                               500
SEQ15 (435)  ETLTLKPEGFVKAKSKK------IPLGGIPSPSTEQSAKKVRKKAE
SEQ17 (437)  QTLTLKPGDFHISVQSRHQEAIHADVQAAEKAAPDEQKEK-TEAKGASVI
SEQ19 (437)  EALTIKPDDEKITVKPRK-------TAAINVQRKEQADIKAETKPKETK 501                                               550
SEQ15 (476)  NAHNTPLIVLYGSNMGTAEGTARDLADIAMSKGFAPQVATIDSHAGNLPR
SEQ17 (486)  GLNNRPLIVLYGSDTGTAEGVARELADTASLHGVRTKTAPLNDRIGKLPK
SEQ19 (479)  PKHGTPLIVLFGSNLGTAEGIAGELAAQGRQMGFTAETAPLDDYIGKLPE 551                                               600
SEQ15 (526)  EGAVLIVTASYNGHPPDNAKQFVDWLDQAS--ADEVKGVRYSVFGCGDKN
SEQ17 (536)  EGAVVIVTSSYNGKPPSNAGQFVQWLQEIK--PGELEGVHYAVFGCGDHN
SEQ19 (529)  EGAVVIVTASYNGAPPDNAAGFVEWLKELE--EGQLKGVSYAVFGCGNRS
```

Figure 15A (cont'd)

```
       601                                                          650
SEQ15  (574) WATTYQKVPAFIDETLAAKGAENIADRGEADASDDFEGTYEEWREHMWSD
SEQ17  (584) WASTYQYVPRFIDEQLAEKGATRFSARGEGDVSGDFEGQLDEWKKSMWAD
SEQ19  (577) WASTYQRIPRLIDMKAKGASRLTAIGEGDAADFESHRESWENRFWKE 651                                                          700
SEQ15  (624) VAAYFNIDIENSE--DNKSTLSLQFVDSAADMPLAKMHGAFSTNVVASKE
SEQ17  (634) AIKAFGELNENAD-KERSTLSLQFVRGLGESPLARSYEASHASIAENRE
SEQ19  (627) TMDAFDINEIAQK--EDRPSLSITFLSEATETPVAKAYGAFEGIVLENRE 701                                                          750
SEQ15  (672) LQQPG-----SARSTRHIEIELPKEASYQEGDHLGVIPRNYEGIVNRVTAR
SEQ17  (683) LQSAD-----SDRSTRHIEIALPPDVEYQEGDHLGVLPKNSQTNVSRILHR
SEQ19  (675) LQTAA-----STRSTRHIELEIPAGKTYKEGDHIGILPKNSRELVQRVLSR 751                                                          800
SEQ15  (718) FGLDASQQIRLEAEEKIAHLPLAKTVSVELLQY-VELQDPVTRTQLRA
SEQ17  (729) FGLKGTDQVTLSASGRSAGHLPLGRPVSLHDLLSYSVEVQEAATRAQIRE
SEQ19  (721) FGLQSNHVIKVSG-SAHMAHLPMDRPIKVVDLLSSYVELQEPASRLQLRE
```

Figure 15B

```
              801                                                       850
SEQ15 (767)   MAAKTVCPPHKVELEALLEKQ------AYKEQVLAKRLTMLELTEKYPACE
SEQ17 (779)   LASFTVCPPHRRELEELSAEG------VYQEQILKKRISMLDLLEKYEACD
SEQ19 (770)   LASYTVCPPHQKELEQIVSDDG------IYKEQVLAKRLTMLDFLEDYPACE 851                                                       900
SEQ15 (812)   MKFSEFIALLPSIRPRYYSISSSPRVDEKQASITVVSGEAWSGYGEYK
SEQ17 (824)   MPFERFLELLRPLKPRYYSISSSPRVNPRQASITVGVVRGPAWSGRGEYR
SEQ19 (816)   MPFERFLALLPSIKPRYYSISSSPKVHANIVSMTVGVKASAWSGRGEYR 901                                                       950
SEQ15 (862)   GIASNYLAELQEGDTITCFISTPQSEFTLPKDPETPLIMVGPGTVAPFR
SEQ17 (874)   GVASNDLAERQAGDDVMFIRTPESRFQLPKDPETPIIMVGPGTVAPFR
SEQ19 (866)   GVASNYLAELNTGDAAACFIRTPQSGEQMPNDPETPMIMVGPGTGIAPFR 951                                                      1000
SEQ15 (912)   GFVQARKQIKEQGQSLGEAHLYFGCRSPHEDYLMQEELENAQSEGIITLH
SEQ17 (924)   GFLQARDVLKREGKILGEAHLYFGCRN-DRDFIYRDELERFEKDGIVIVH
SEQ19 (916)   GFIQARSVIKKEGSILGEALLYFGCRRPDHDDLYREELDQAEQDGLVTIR
```

Figure 15B (cont'd)

```
                1050
SEQ15  (1001)  TAFSRMPNQPKTYVQHVMEQDGKKLIELLLDQGAHFYICGDGSQMAPAVEA
SEQ17   (962)  TAFSRKEGMPKTYVQHLMADQADTLISILDRGGRLYVCGDGSKMAPDVEA
SEQ19   (973)  RCYSRVENEPKGYVQHLLKQDTQKIMTLIEKGAHIYVCGDGSQMAPDVER
                       (966)

1051                         1088
SEQ15  (1012)  TLMKSYADVHQVSEADARLWLQQLEEKGRYAKDVWAG-
SEQ17  (1023)  ALQKAYQAVHGTGEQFAQNWLRHLQDTGMYAKDVWAGI
SEQ19  (1016)  TLRLAYEAEKAASQEESAVWLQKLQDQRRYVKDVWTGM
```

Figure 15B (cont'd)

SEQ 14

```
   1 atgacaatta aagaaatgcc tcagccaaaa acgtttggag agcttaaaaa tttaccgtta
  61 ttaaacacag ataaaccggt tcaagctttg atgaaaattg cggatgaatt aggagaaatc
 121 tttaaattcg aggcgcctgg tcgtgtaacg cgctacttat caagtcagcg tctaattaaa
 181 gaagcatgcg atgaatcacg ctttgataaa aacttaagtc aagcgcttaa atttgtacgt
 241 gattttgcag gagacgggtt atttacaagc tggacgcatg aaaaaaattg gaaaaaagcg
 301 cataatatct tacttccaag cttcagtcag caggcaatga aaggctatca tgcgatgatg
 361 gtcgatatcg ccgtgcagct tgttcaaaag tgggagcgtc taaatgcaga tgagcatatt
 421 gaagtaccgg aagacatgac acgtttaacg cttgatacaa ttggtctttg cggctttaac
 481 tatcgcttta acagctttta ccgagatcag cctcatccat ttattacaag tatggtccgt
 541 gcactggatg aagcaatgaa caagctgcag cgagcaaatc cagacgaccc agcttatgat
 601 gaaaacaagc gccagtttca agaagatatc aaggtgatga cgacctagt agataaaatt
 661 attgcagatc gcaaagcaag cggtgaacaa agcgatgatt tattaacgca tatgctaaac
 721 ggaaaagatc cagaaacggg tgagccgctt gatgacgaga acattcgcta tcaaattatt
 781 acattcttaa ttgcgggaca cgaaacaaca agtggtcttt tatcatttgc gctgtatttc
 841 ttagtgaaaa atccacatgt attacaaaaa gcagcagaag aagcagcacg agttctagta
 901 gatcctgttc caagctacaa acaagtcaaa cagcttaaat atgtcggcat ggtcttaaac
 961 gaagcgctgc gcttatggcc aactgctcct gcgttttccc tatatgcaaa agaagatacg
1021 gtgcttggag gagaatatcc tttagaaaaa ggcgacgaac taatgttct gattcctcag
1081 cttcaccgtg ataaaacaat tggggagac gatgtggaag agttccgtcc agagcgtttt
1141 gaaaatccaa gtgcgattcc gcagcatgcg tttaaaccgt tggaaacgg tcagcgtgcg
1201 tgtatcggtc agcagttcgc tcttcatgaa gcaacgctgg tacttggtat gatgctaaaa
1261 cactttgact tgaagatca tacaaactac gagctggata ttaaagaaac tttaacgtta
1321 aaacctgaag gctttgtggt aaaagcaaaa tcgaaaaaaa ttccgcttgg cggtattcct
1381 tcacctagca ctgaacagtc tgctaaaaaa gtacgcaaaa aggcagaaaa cgctcataat
1441 acgccgctgc ttgtgctata cggttcaaat atgggaacag ctgaaggaac ggcgcgtgat
1501 ttagcagata ttgcaatgag caaaggattt gcaccgcagg tcgcaacgct tgattcacac
1561 gccggaaatc ttccgcgcga aggagctgta ttaattgtaa cggcgtctta taacggtcat
1621 ccgcctgata acgcaaagca atttgtcgac tggttagacc aagcgtctgc tgatgaagta
1681 aaaggcgttc gctactccgt atttggatgc ggcgataaaa actgggctac tacgtatcaa
1741 aaagtgcctg cttttatcga tgaaacgctt gccgctaaag gggcagaaaa catcgctgac
1801 cgcggtgaag cagatgcaag cgacgacttt gaaggcacat atgaagaatg gcgtgaacat
1861 atgtggagtg acgtagcagc ctactttaac ctcgacattg aaaacagtga agataataaa
1921 tctactcttt cacttcaatt tgtcgacagc gccgcggata tgccgcttgc gaaaatgcac
1981 ggtgcgtttt caacgaacgt cgtagcaagc aaagaacttc aacagccagg cagtgcacga
2041 agcacgcgac atcttgaaat tgaacttcca aaagaagctt cttatcaaga aggagatcat
2101 ttaggtgtta ttcctcgcaa ctatgaagga atagtaaacc gtgtaacagc aaggttcggc
2161 ctagatgcat cacagcaaat ccgtctggaa gcagaagaag aaaaattagc tcatttgcca
2221 ctcgctaaaa cagtatccgt agaagagctt ctgcaatacg tggagcttca agatcctgtt
2281 acgcgcacgc agcttcgcgc aatggctgct aaaacggtct gcccgccgca taagtagag
2341 cttgaagcct tgcttgaaaa gcaagcctac aaagaacaag tgctggcaaa acgtttaaca
2401 atgcttgaac tgcttgaaaa atacccggcg tgtgaaatga attcagcga atttatcgcc
2461 cttctgccaa gcatacgccc gcgctattac tcgatttctt catcacctcg tgtcgatgaa
2521 aaacaagcaa gcatcacggt cagcgttgtc tcaggagaag cgtggagcgg atatggagaa
2581 tataaaggaa ttgcgtcgaa ctatcttgcc gagctgcaag aaggagatac gattacgtgc
2641 tttatttcca caccgcagtc agaatttacg ctgccaaaag accctgaaac gccgcttatc
2701 atggtcggac cgggaacagg cgtcgcgccg tttagaggct ttgtgcaggc gcgcaaacag
2761 ctaaaagaac aaggacagtc acttggagaa gcacatttat acttcggctg ccgttcacct
2821 catgaagact atctgtatca agaagagctt gaaaacgccc aaagcgaagg catcattacg
2881 cttcataccg ctttttctcg catgccaaat cagccgaaaa catacgttca gcacgtaatg
2941 gaacaagacg caagaaatt gattgaactt cttgatcaag gagcgcactt ctatatttgc
3001 ggagacggaa gccaaatggc acctgccgtt gaagcaacgc ttatgaaaag ctatgctgac
3061 gttcaccaag tgagtgaagc agacgctcgc ttatggctgc agcagctaga agaaaaaggc
3121 cgatacgcaa aagacgtgtg ggctgggtaa
```

FIGURE 16A

SEQ 16
```
   1 atgaaggaaa caagcccgat tcctcagccg aagacgtttg ggccgctcgg caatttgcct
  61 ttaattgata aagacaaacc gacgctttcg ctgatcaaac tggcggaaga acagggcccg
 121 attttcaaa tccatacacc cgcgggcacg accattgtag tgtccggcca tgaattggtg
 181 aaagaggttt gtgatgaaga acggtttgat aaaagcattg aaggcgcctt ggaaaaggtt
 241 cgcgcatttt ccggtgacgg attgtttacg agctggacgc atgagcctaa ctggagaaaa
 301 gcgcacaaca ttctgatgcc gacgttcagc cagcgggcca tgaaggacta tcatgagaaa
 361 atggtcgata tcgctgttca gctcattcaa aaatgggcaa ggctcaaccc gaatgaagca
 421 gtcgatgtcc cgggagatat gacccggctg acgctcgaca ccattgggct atgcgggttt
 481 aactaccgct taacagtta ctacagagaa acgccccacc cgtttatcaa cagcatggtg
 541 cgggcgcttg atgaagcgat gcatcaaatg cagcggcttg atgttcaaga taagcttatg
 601 gtcagaacaa agcggcaatt ccgctatgat attcaaacga tgttttcgtt agtcgacagc
 661 attattgcag agcgcagggc gaatggagac caggatgaaa aagatttgct cgcccgcatg
 721 ctgaatgtgg aagatccgga aactggtgaa aagctcgacg acgaaaatat ccgctttcag
 781 atcatcacgt ttttgattgc cggccatgaa acaacgagcg gcctgctttc ctttgcgact
 841 tacttttat tgaagcatcc tgacaaactg aaaaaggcgt atgaagaggt cgatcgggtg
 901 ctgacggatg cagcgccgac ctataaacaa gtgctggagc ttacatacat acggatgatt
 961 ttaaatgaat cactgcgctt atggccgaca gctccggctt tcagccttta tccaaaagaa
1021 gacacagtca ttggcggaaa atttccgatc acgacgaatg acagaatttc tgtgctgatt
1081 ccgcagcttc atcgtgatcg agacgcttgg ggaaaggacg cagaagaatt ccggccggaa
1141 cggtttgagc atcaggacca agtgcctcat catgcgtaca aaccattcgg aaatggacaa
1201 cgggcctgta tcggcatgca gtttgccctt catgaagcca cacttgtgtt aggcatgatt
1261 ctaaaatatt tcacattgat tgatcatgag aattatgagc ttgatatcaa acaaacctta
1321 acacttaagc cgggcgattt tcacatcagt gttcaaagcc gtcatcagga agccattcat
1381 gcagacgtcc aggcagctga aaaagccgcg cctgatgagc aaaaggagaa acggaagca
1441 aaggtgcat cggtcatcgg tcttaacaac cgcccgcttc tcgtgctgta cggctcagat
1501 accggcaccg cagaaggcgt cgcccgggag cttgctgata ctgccagtct tcacggcgta
1561 aggacaaaga cagcacctct gaacgaccgg attggaaagc tgccgaaaga gggagcggtt
1621 gtcattgtga cctcgtctta taatgaaaag ccgccaagca atgccggaca attcgtgcag
1681 tggcttcaag aaatcaaacc gggtgagctt gagggcgtcc attacgcggt atttggctgc
1741 ggcgaccaca actgggcgag cacgtatcaa tacgtgccga gattcattga tgagcagctt
1801 gcggagaaag gcgcgactcg gttttctgcg cgcggggaag gggatgtgag cggtgatttt
1861 gaagggcagc ttgacgagtg aaaaaagc atgtgggcgg atgccatcaa agcattcgga
1921 cttgagctta atgaaaacgc tgataaggaa cgaagcacgc tgagccttca gtttgtcaga
1981 gggctgggcg agtctccgct cgctagatcg tacgaagcct ctcacgcatc cattgccgaa
2041 aatcgtgaac tccagtccgc agacagcgat cgaagcactc gccatatcga aattgcattg
2101 ccgccggatg ttgaatatca agagggcgac catcttggcg tattgccaaa aaacagccaa
2161 accaatgtca gccggattct tcacagattc ggtctgaagg aaccgacca agtgacattg
2221 tcggcaagcg gccgcagtgc ggggcatctg ccattgggcc gtcctgtcag cctgcatgat
2281 cttctcagct acagcgtcga ggtgcaggaa gcagccacaa gagcgcaaat acgtgaactg
2341 gcgtcattta cagtgtgtcc gccgcatagg cgcgaattag aagaactgtc agcagagggt
2401 gtttatcagg agcaaatatt gaaaaaacga atttccatgc tggatctgct tgaaaagtat
2461 gaagcgtgtg acatgccgtt tgaacgattt ttagagcttt tacggccgtt aaaaccgaga
2521 tactattcga tttcaagctc tccaagagtg aatccgcggc aagcatcgat cacagtcggt
2581 gtcgtgcgcg gcccggcgtg gagcggccgt ggcgaataca ggggtgtggc atcaaatgat
2641 ttagctgagc gtcaagccgg tgatgatgtc gtgatgttta tccgcacacc ggaatcccgg
2701 tttcagcttc cgaaagaccc tgaaacgcca attattatgg tcgggccagg cacgggagtc
2761 gcgccatttc gcggttttcct tcaagcccgc gatgttttaa agcgggaggg caaaacgctc
2821 ggtgaggctc atctctattt tggatgcagg aacgatcggg attttattta ccgagatgag
2881 cttgagcggt ttgaaaaaga cggaatcgtc actgtccaca cagccttttc ccgaaaagag
2941 ggcatgccga aaacatatgt ccagcatctc atggctgacc aagcagatac attaatatca
3001 atccttgacc gcggtggcag gctttatgta tgcggtgatg gcagcaaaat ggccccggat
3061 gtggaggcgg cacttcaaaa agcgtatcag gctgtccatg gaaccgggga acaagaagcg
3121 caaaactggc tgagacatct gcaggatacc ggtatgtacg ctaaggatgt ctgggcaggg
3181 atatag
```

FIGURE 16B

SEQ 18
```
   1 ttacattcct gtccaaacgt ctttcacata acgtctttga tcttgcagct tttgcagcca
  61 tacagctgat tcttcctgac ttgctgcttt ttcagcttca tatgccaatc gcaaagttct
 121 ctctacatca ggagccattt gcgatccatc accgcatacg taaatatgag cccctttttc
 181 aatgagtgtc atcaatttct gcgtatcttg cttgagcaag tgctggacat atcctttggg
 241 ttcgttttcg acgcgcgagt agcatcggcg gattgtgacc aaaccgtcct gttccgcttg
 301 atccagctct tctctgtaaa ggtcgtcatg gtccgggcgg cggcagccga agtataaaag
 361 tgcttcacca agggtgcttc cttccttctt caaaaccgat cttgcctgaa taaagcctct
 421 gaatggcgca attcctgtgc ccggcccgac cataatcata ggcgtttcag gatcattcgg
 481 catctgaaat ccggactgcg gcgtacgaat gaagcaagct gctgcatcac ctgtattcaa
 541 ttctgctaaa taattagagg cgacaccccg gtattcacct cggccgctcc atgctgaggc
 601 tttcacaact cctaccgtca tgctcacgat atttgcatga actttcggtg agcttgaaat
 661 ggaatagtat ctcggtttta gtgatggcaa aagtgctaaa aaccgttcaa acggcatttc
 721 gcaagcagga taatcctcta aaaaatcaag catggtaaga cgttttgcaa gtacctgctc
 781 tttgtaaatg ccatcatctg aaacgagctg ttccagctct ttttgatgcg gcggacaaac
 841 tgtataagag gccagctccc gaagctgaag ccttgatgcc ggttcctgca gctctacata
 901 ggacgacaat aaatccacta ctttgattgg ccgatccatc ggcagatgag ccatatgagc
 961 gcttccgctt acttttatca catgattgga ctgcaaaccg aatcggctga gaacccgctg
1021 aacaagctcc ctgctgttct ttggcaggat tccgatatga tcgccttctt tatatgtttt
1081 accagccgga atttccaatt caatatggcg ggttgaacgc gtgctggcag ctgtctggag
1141 ttctcgattc tctaacacaa tcccttcaaa cgcgccatat gctttagcaa ccggcgtttc
1201 cgtcgcttca ctgagaaaag taatcgataa tgaaggcctg tcttctttct gggctatttc
1261 gttaatatca aatgcgtcca tcgtttcctt ccagaagcgg ttttcccaag actcgcggtg
1321 gctttcaaaa tcatcggcgg cgtcaccttc cccaatcgct gttaaacgcg atgccccctt
1381 tgctttcatc atgtcatcaa tcaggcgggg aatccgctga tacgtgctgg cccagctccg
1441 gtttccgcag ccgaataccg cataggaaac acctttcaat tggccttcct caagctcttt
1501 cagccactct acaaatccgg cagcattatc aggcggcgcc ccattataag aagccgttac
1561 aatgacgact gccccttctt cagggagctt gccgatataa tcatcaagcg gagccgtttc
1621 agctgtaaag cccatctggc ggccttgagc agccagttca ccggctattc cctcagctgt
1681 cccaagattt gaaccaaaaa gaacaagtaa aagtgtgccg tgtttaggtt tggtttcttt
1741 tggctttgtt tctgctttga tgtctgcctg ttcttttctc tgtacattga ttgccgctgt
1801 ttttcgcggt ttcacagtaa ttttaaaatc atccggcttg atcgttaatg cttctttgat
1861 ttttagttcg tagccagtat ggtttatcaa ttcaaaatgc tttaatacaa gaccgagaac
1921 cattgtcgct tcttgaagag caaactgcat gccaatacaa gcgcgctgtc cgtttccaaa
1981 cggcttatac gcatggtgag ggatacttga aggatcctca aaccgttccg gacggaaatc
2041 ttccgcatcc ggtccccaag cgttttgatc ccggtgcagt tttggaatta aaacagtgac
2101 tggctgccct ttgctgatcg gatattcccc gcctagaaca gtatcctcct tgcatatag
2161 agaaaaagcc ggagctgttg gatacagtct gagggtttca tttaaaacca tccgaatgta
2221 tttgagctgc tggatttgtt tatattcagg cgtgtcatcc gttaacacgc gatccgcttc
2281 ctcctgagct ttttcagtt tttccggatg tgtaagcaga caataaatcg caaaggatag
2341 caacccgctt gttgtctcat gtccagcaat taaaaatgtg atgatttggt atcgaatgtt
2401 ttcgtcatcc agcgttttcac ccgttactgg atcttttggca taaagcatga gagacaagag
2461 atccttaatg ttttcatccg gattcgcctt tcgctccgct atcattctat caaccaggga
2521 gttcatgact tctatatcct tttggaactg cagcttcgtt ttcaccatca ttttatcttg
2581 caggcccagt cttttcgatt gattcatcgc ctcttttaag gcacggagca tactggtgat
2641 aaacggatgc tgtgaatcac ggtaaaagct gttgaatcga tagttaaacc cgcataaccc
2701 aatcgtatca agcgtcagac gtgtcatatc gtccgctaca tcaatttctt cattagggtt
2761 taaccggctc cacttttgaa tcagctgggt tgcgatatcc agcatcatag aatgatagcc
2821 tttcatcgct ttttgactaa aactcggcag caaaatgcgg tgggcttttt gccagttcgg
2881 ttcgtgcgtc cagcttgtaa ataagccatc tcccccgaac tcacgcacct tttgcaagcc
2941 tttgccaagg ttcttgtcaa agcgtttttc atcacacact tcagcacaa gattgtggcc
3001 ggacacaaaa acactggata ctcccggaaa atcaaaacgg aaaatcggtc ccaattcatc
3061 agctatccgc cataaggatt gagaaagctg ttcttttcc agatgcgaa gattttttaa
3121 aggtccgtat gttttgggct gaggtattgc gcttgcctgt ttcat
```
FIGURE 16C

METHODS AND COMPOSITIONS FOR PREPARATION OF SELECTIVELY PROTECTED CARBOHYDRATES

CROSS REFERENCE TO RELATED APPLICATIONS

This application claims priority under 35 U.S.C. §119 from Provisional Application Ser. No. 60/936,044, filed Jun. 18, 2007, and Provisional Application Ser. No. 60/936,774, filed Jun. 22, 2007, the disclosures of which are incorporated herein by reference.

STATEMENT AS TO FEDERALLY SPONSORED RESEARCH

A portion of the work described herein was supported by Grant No. GM044154 and GM 73500 awarded by the National Institutes of Health. The United States Government has certain rights in this invention.

TECHNICAL FIELD

The disclosure relates to engineered P450 polypeptides and use of such polypeptides in chemoenzymatic methods to construct selectively protected carbohydrates, which are useful as building blocks for preparation of carbohydrate derivatives and oligosaccharides.

BACKGROUND

Oligosaccharides are important in a wide variety of intracellular recognition events, including processes that mediate inflammation, cancer metastasis, and bacterial and viral infection. Glycosylation mediates the function and stability of glycoproteins, including biopharmaceuticals such as erythropoietin. (Varki, A. et al. 1999; Ernst, B. et al. 2000; Bertozzi, C. et al. 2001; Schofield, L. et al. 2002). Oligosaccharide biosynthesis is non-template directed, and leads to heterogenous mixtures of related structures that are difficult to separate. Thus, natural sources of oligosaccharides are not structurally defined, and detailed mechanistic studies of oligosaccharide-mediated events require synthetic material.

SUMMARY

The disclosure provides methods to differentiate hydroxyl groups, to provide selectively protected monosaccharides by regio-selective deprotection of peralkylated monosaccharide derivatives using one or more monooxygenases.

Unlike other methods, this synthetic route proceeds in as few as two steps to differentiate a particular carbohydrate hydroxyl group by deprotecting alkyl ethers under mild aqueous conditions, without the use of toxic reagents or organic solvents.

The disclosure provides a method for regioselective removal of alkyl ethers in protected carbohydrates comprising contacting the carbohydrate with a monooxygenase. In another aspect the disclosure provides a method for the selective demethylation of permethylated monosaccharide derivatives with a variety of substituents at an anomeric position comprising contacting the permethylated monosaccharide with a monooxygenase. In one embodiment, the monooxygenase is a cytochrome P450. In another embodiment, the cytochrome P450 comprises at least 80% sequence identity to a member of the CYP102A family. In another embodiment, the monooxygenase comprises at least 80%-100% sequence identity to SEQ ID NO:1, 2, 3, 4, 5, 6, 7, 8, 9, 10, 11, 12 or 13. In another embodiment, the monooxygenase comprises a sequence as set forth in SEQ ID NO:1, 2, 3, 4, 5, 6, 7, 8, 9, 10, 11, 12 or 13 and comprises from 1-20 conservative amino acid substitutions.

The disclosure also provides a substantially purified polypeptide comprising a sequence that is at least 80% identical to a sequence selected from the group consisting of: (a) SEQ ID NO:1 having a mutation at position F87; (b) SEQ ID NO:1 having a mutation at position A82; (c) SEQ ID NO:1 having a mutation at position F87 and A82; (d) SEQ ID NO:1 having a mutation at position F87, A82, and A328; (e) SEQ ID NO:1 having a mutation at position F87, A82, A328, and A78; (f) SEQ ID NO:1 having a mutation at position F87, C47, and I94; (g) SEQ ID NO:1 having a mutation at position F87, C47, and I94; (h) SEQ ID NO:1 having a mutation at position C47, A78, F87, I94, A180, V184, and A330; and (i) SEQ ID NO:1 having a mutation at position C47, A78, F87, I94, I263, V184, and A330, wherein the polypeptide catalyzes the selective deprotection of a monosaccharide. In one embodiment, the F87 mutation is selected from the group consisting of an F87A, F87V, and F87I mutation. In another embodiment, the A82 mutation is selected from the group consisting of an A82L, A82F, and A82G mutation. In yet another embodiment, the A328 mutation is selected from the group consisting of an A328V and an A328L mutation. In a further embodiment, the A78 mutation is selected from the group consisting of an A78T and A78L. In another embodiment, the C47 mutation is a C47R mutation. In yet another embodiment, the I94 mutation is an I94K mutation. In another embodiment, the A180 mutation is an A180V mutation. In yet a further embodiment, the V184 mutation is a V184T mutation. In another embodiment, the I263 mutation is an I263M mutation. In another embodiment, the A330 mutation is an A330V mutation.

The disclosure also provides a substantially purified polypeptide having at least 80-100% identity to a sequence selected from the group consisting of: (a) SEQ ID NO:2, (b) SEQ ID NO:3, (c) SEQ ID NO:4, (d) SEQ ID NO:5, (e) SEQ ID NO:6, (f) SEQ ID NO:7, (g) SEQ ID NO:8, (h) SEQ ID NO:9, (i) SEQ ID NO:10, (j) SEQ ID NO:11, (k) SEQ ID NO:12, and (l) SEQ ID NO:13, wherein the polypeptide selectively deprotects a monosaccharide.

The disclosure also provides an isolated polynucleotide encoding a polypeptide useful in the methods of the disclosure. A vector (e.g., an expression vector) comprising the polynucleotide is also provided. In addition, cells recombinantly produced to contain or express the polynucleotide or vector are also provided.

The disclosure also provides a method to analyze carbohydrate composition, comprising: (a) permethylating hydroxyl groups of a carbohydrate substrate; and (b) selectively deprotecting the carbohydrate substrate by a polypeptide of the disclosure.

A method of identifying a monooxygenase comprising the activity of regio-selective deprotection of a carbohydrate comprising screening an enzyme library for relative activity among different methylated carbohydrates or carbohydrate derived molecule or their analogs.

A method of generating selectively protected oligosaccharides is also provided, the method including contacting a protected monosaccharide with a polypeptide of the disclosure under conditions wherein the polypeptide and protected monosaccharide interact and the monosaccharide is selectively deprotected.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 13A-D show useful monooxygenase variants of the disclosure.

FIG. 14A-C shows the sequence of parental P450 monooxygenases (SEQ ID NO:15, 17 and 19).

FIG. 15A-B shows an alignment of the sequences from FIG. 14A-C. One of skill in the art can readily identify conserved residues based upon the alignment.

FIG. 16A-C shows the cDNA sequences (SEQ ID NO:14, 16, and 18) encoding parental P450 monooxygenases.

DETAILED DESCRIPTION

Figure 1A:
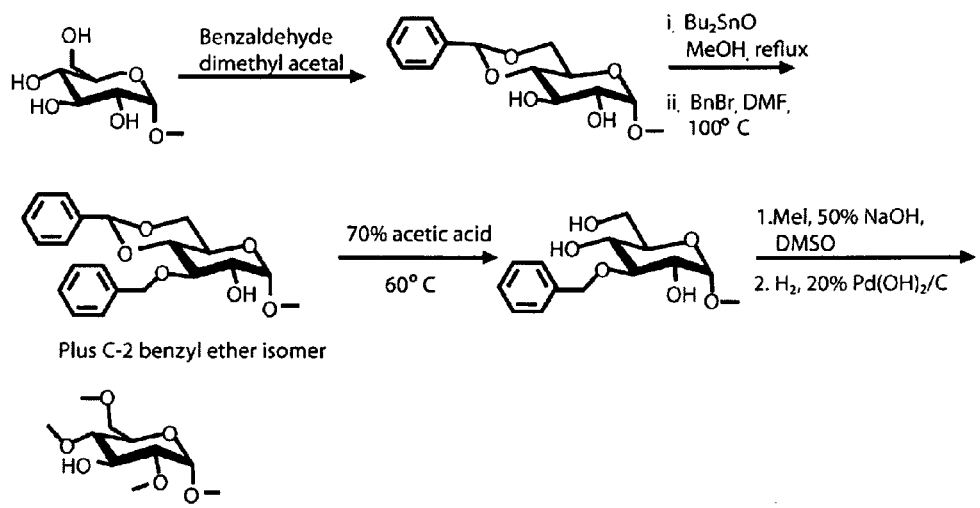
FIG. 1A-D shows a comparison between a typical synthesis procedure (A), and the procedure described in this disclosure (B, C, and D).
Figure 1B:
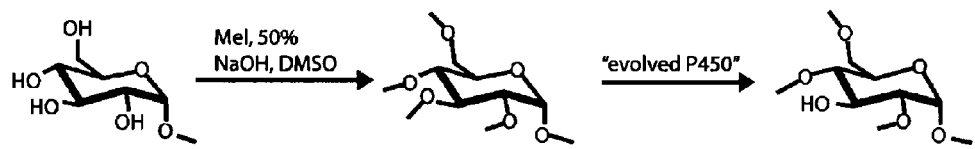

As used herein and in the appended claims, the singular forms "a," "and," and "the" include plural referents unless the context clearly dictates otherwise. Thus, for example, reference to "a P450 enzyme" includes a plurality of such P450 enzymes and reference to "the polypeptide" includes reference to one or more polypeptides and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Compared to the chemical synthesis of the other biopolymers, nucleic acids and proteins, oligosaccharides have an additional level of complexity that has to be addressed, such as region-selectivity. In addition, anomeric stereo selectivity must be controlled.

Unlike nucleic acids and proteins, many oligosaccharide building blocks are not commercially available, and each target oligosaccharide requires a different set of building blocks, which can only be accessed through tedious, multistep synthesis. To date, there is no general method for preparing selectively protected monosaccharides.

Several strategies to prepare specific regio-selectively protected monosaccharide units have been developed, to obtain free hydroxyl groups at desired positions as nucleophile acceptors in glycosylation reactions. (Tsuchiya, T. in Glycoscience: Chemistry and Chemical Biology, Vol. 1, Fraser-Reid, B., Tatsuta, K, Thiem, J. Eds.; Springer: Berlin, 2001; pp. 119-194). These methods are of limited applicability, being specific for a particular building block. They also require multiple steps, use of organic solvents and toxic reagents. Recently, a chemical "one-pot" approach to the synthesis of selectively protected glucose derivatives has been reported (Wang, C.-C.; Lee, J.-C.; Luo, S.-Y.; Kulkarni, S. S.; Huang, Y.-W.; Lee, C.-C.; Chang, K.-L.; Hung, S.-C. Nature, 2007, 446, 869-899). Although this approach is a significant advance over previous methods, it still requires the use of toxic and highly reactive reagents, and a high level of technical expertise.

Chemoenzymatic methods utilizing lipases or esterases to region-selective lyde-protect acetylated carbohydrates have been reported (Bastida, A. et al., 1999; Terreni, M. et al. 2002; Shaw, J. F. et al., 1987; Hennen, W. J. et al., 1988; Khan, R. et al., 1993). However, yields and selectivities were variable, suggesting that this is not a general approach, and no attempts to improve the activity beyond that observed for wild type enzymes were reported.

The disclosure provides methods and compositions for selective oligosaccharide synthesis. The synthesized carbohydrates with differentiated hydroxyl groups can be used as intermediates in the synthesis of various polysaccharides, including drug candidates that possess carbohydrate moieties for their function or improved solubility or biological half-life. Examples of these products include glycoproteins such as erythropoietin, and analogs of natural products such as vancomycin, erythromycin, calicheamicin, doxorubicin, and novobiocin, or compounds with low solubility such as taxol.

The disclosure provides a method for differentiating hydroxyl groups on carbohydrates by region selective dealkylation of peralkylated monosaccharide derivatives using one or more monooxygenases engineered as described herein or modified by mutagenesis and selected for an activity. Comparison between a typical procedure to synthesize a protected compound having a single free hydroxyl group and the chemo-enzymatic procedure of this disclosure is shown in FIG. 1. Examples of alkyl ethers include methyl, substituted ethyl, benzyl, 4-methoxybenzyl, 4-nitrobenzyl, methoxymethyl, benzyloxymethyl, allyl and propargyl ethers. Alkyl carbonates may be used in analogous fashion as cleavage of the alkyl group will result in release of $CO_2$ and deprotection of the hydroxyl. The peralkylated carbohydrates are readily obtained in a single step, using an alkylating reagent such as methyl iodide, dimethyl sulfate, benzyl bromide, 4-methyoxybenzyl chloride, 4-nitrobenzyl bromide, methoxymethyl chloride, benzyloxymethyl chloride, allyl bromide, propargyl bromide and 2-(trimethylsilyl)ethoxymethyl chloride, and the carbonates are obtained through the use of the corresponding alkyl chloroformate. Examples of monosaccharide substrates are D-glucose, D-galactose, D-mannose, D-fucose, N-acetyl D-glucosamine, N-acetylneuraminic acid, Neuraminic acid, L-galactose, L-arabinose, D-xylose, D-ribose and D-deoxyribose. Examples of disaccharide substrates are sucrose, lactose, maltose, trehalose and cellobiose. Partly modified derivatives of these compounds such as benzyl, octyl, benzoyl, p-nitrobenzoyl, alkyne, methyleneazide, e.g., at the anomeric and/or primary alcohol positions.

Saccharide-selective dealkylation by monooxygenases can be used to analyze the sequence of an oligosaccharide, by detecting the presence of one or more specific carbohydrate molecules in the substrate. The dealkylation assay is monitored by a simple calorimetric assay that can be read on a multi-well plate reader. The aldehyde formed by this dealkylation reaction can be quantified by reaction with reagents such as Purpald (Hopps et al. 2000). The reaction can also be monitored by gas chromatography, high performance liquid chromatography, mass spectrometry, or related methods or combinations thereof. For example, this method can be applied to identify the composition of complex polysaccharides, such as glycans attached to glyco-proteins or other glyco-conjugates.

Cytochrome P450 enzymes (P450s) are exceptional oxidizing catalysts, effecting highly selective transformations that are sometimes impossible to achieve by chemical methods under similarly mild conditions. These versatile enzymes have enormous potential for applications in drug discovery, chemical synthesis, bioremediation, and biotechnology.

The P450 catalytic cycle is initiated by a substrate binding event that is accompanied by large conformational changes and a shift in the heme redox potential. This induces electron transfer from the NAD(P)H cofactor to the heme, resulting in the formation of the highly reactive iron-oxo species that activates the substrate. P450s insert oxygen into a broad range of compounds.

Accordingly, the term "hydroxylase" or "monooxygenase" should be considered to include any enzyme that can insert one oxygen atom from diatomic oxygen into a substrate. Exemplary enzymes include the cytochrome P450 monooxygenases. "Cytochrome P450 monooxygenase" or "P450 enzyme" means an enzyme in the superfamily of P450 heme-thiolate proteins, which are widely distributed in bacteria, fungi, plants and animals. The unique feature which defines whether an enzyme is a cytochrome P450 enzyme is traditionally considered to be the characteristic absorption maximum ("Soret band") near 450 nm observed upon binding of carbon monoxide (CO) to the reduced form of the heme iron of the enzyme. Reactions catalyzed by cytochrome P450 enzymes include epoxidation, N-dealkylation, O-dealkylation, S-oxidation and hydroxylation. The most common reaction catalyzed by P450 enzymes is the monooxygenase reaction, i.e., insertion of one atom of oxygen into a substrate while the other oxygen atom is reduced to water.

As described more fully herein an engineered bacterial cytochrome P450 BM-3 (BM3), a fatty acid hydroxylase from *Bacillus megaterium*, was engineered and used to regio-selectively deprotect globally protected monosaccharides, providing a potentially general method to access any desired building block. P450-BM3 provides a flexibly-engineered polypeptide because it possesses properties that make it both a practical catalyst and straight forward to engineer: BM-3 is highly soluble, exhibits high catalytic rates on substrates (thousands of turnovers per minute) and is readily expressed at high levels in a heterologous host such as *Escherichia coli*. Additionally, BM3 is catalytically self-sufficient (its hydroxylase domain and reductase domains occur as a natural fusion on a single peptide chain), unlike most other monooxygenases that require additional electron transfer proteins for activity. Engineered BM3 variants were identified that were able to differentiate several hydroxyl group positions of different permethylated monosaccharide derivatives with high selectivity. Examples of suitable monooxygenases are members of the cytochrome P450 family of enzymes (EC 1.14.14.1). Bacterial cytochrome P450s include CYP101A, CYP102A and derivatives and mutants thereof such as 9-10A derivatives and the chimeric enzymes, as described more fully below. Examples of mammalian cytochrome P450s that can be used in the methods of the disclosure (or mutated) include CYP2C9, CYP3A4, and CYP2A6. Other cytochrome P450s are CYP1A1, CYP1A2, CYP1B1, CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1, CYP3A4, CYP3A5, CYP3A7, CYP3A43, CYP4A11, CYP4A22, CYP4B1, CYP4F2, CYP4F3, CYP4F8, CYP4F11, CYP4F12, CYP4F22, CYP4V2, CYP4X1, CYP4Z1, CYP5A1, CYP7A1, CYP7B1, CYP8A1, CYP8B1, CYP11A1, CYP11B1, CYP11B2, CYP17A1, CYP19A1, CYP20A1, CYP21A2, CYP24A1, CYP26A1, CYP26B1, CYP26C1, CYP27A1, CYP27C1, CYP39A1, CYP46A1, CYP51A1.

The disclosure provides cytochrome P450 enzymatic polypeptides that are able to regio-selectively deprotect alkyl ethers of peralkylated monosaccharide derivatives. By a combination of chemical alkylation and selective monooxygenase-catalyzed deprotection, the P450 polypeptides of the disclosure were used to prepare selectively protected carbohydrates as building blocks for chemical synthesis of oligosaccharides.

The engineered cytochromes P450 mutants described throughout the disclosure comprise point mutations to a wild-type P450, chimeric P450 domains or a combination of both. An alternative method for making libraries of P450 mutants capable of being used in the methods of the disclosure include directed evolution to obtain P450s with new or altered properties by recombination, or chimeragenesis, in which portions of homologous P450s are swapped to form functional chimeras. Recombining equivalent segments of homologous proteins generates variants in which every amino acid substitution has already proven to be successful in one of the parents. A structure-based algorithm, such as SCHEMA, identifies fragments of proteins that can be recombined to minimize disruptive interactions that would prevent the protein from folding into an active form. SCHEMA has been used to design chimeras of P450 BM-3 and its homolog CYP102A2, sharing 63% amino acid sequence identity. Properly folded heme domains can be determined by CO difference spectra.

As presented in this disclosure, it has been found that when these recombined, functional cytochrome p450 heme domains enzyme are fused to the reductase domain to generate functional monooxygenase activity, the enzymes have different substrate activity profiles as well as changes in enzyme properties, such as enzyme activity, as compared to a unrecombined heme domain fused to a reductase domain or as compared to the parent cytochrome p450 enzyme. Because of differences in activity profiles, these engineered cytochrome p450 holoenzymes provide a unique basis to screen for activities on novel substrates, including drug compounds, as well as identifying activity against organic chemicals, such as environmental toxins, not normally recognized by the parent enzymes.

Thus, as illustrated by various embodiments herein, the disclosure provides heme-reductase polypeptides, wherein the reductase domain is operably linked or fused to the heme domain (see, e.g., the Chimera table for exemplary sequences of segments and reductase domains). In some embodiments, the polypeptide comprises a chimeric heme domain and a reductase domain; the heme domain comprising from N- to C-terminus: (segment 1)-(segment 2)-(segment 3)-(segment 4)-(segment 5)-(segment 6)-(segment 7)-(segment 8);

wherein segment 1 is amino acid residue from about 1 to about $x_1$ of SEQ ID NO:15 ("1"), SEQ ID NO:17 ("2") or SEQ ID NO:19 ("3"); segment 2 is from about amino acid residue $x_1$ to about $x_2$ of SEQ ID NO:15 ("1"), SEQ ID NO:27 ("2") or SEQ ID NO:19 ("3"); segment 3 is from about amino acid residue $x_2$ to about $x_3$ of SEQ ID NO:15 ("1"), SEQ ID NO:17 ("2") or SEQ ID NO:19 ("3"); segment 4 is from about amino acid residue $x_3$ to about $x_4$ of SEQ ID NO:15 ("1"), SEQ ID NO:17 ("2") or SEQ ID NO:19 ("3"); segment 5 is from about amino acid residue $x_4$ to about $x_5$ of SEQ ID NO:15 ("1"), SEQ ID NO:17 ("2") or SEQ ID NO:19 ("3"); segment 6 is from about amino acid residue $x_5$ to about $x_6$ of SEQ ID NO:15 ("1"), SEQ ID NO:17 ("2") or SEQ ID NO:19 ("3"); segment 7 is from about amino acid residue x6 to about $x_7$ of SEQ ID NO:15 ("1"), SEQ ID NO:17 ("2") or SEQ ID NO:19 ("3"); and segment 8 is from about amino acid residue $x_7$ to about $x_8$ of SEQ ID NO:15 ("1"), SEQ ID NO:17 ("2") or SEQ ID NO:19 ("3");

wherein: $x_1$ is residue 62, 63, 64, 65 or 66 of SEQ ID NO:15, or residue 63, 64, 65, 66 or 67 of SEQ ID NO:17 or SEQ ID NO:19; $x_2$ is residue 120, 121, 122, 123, 124, 125, 126, 127, 128, 129, 130, 132 or 132 of SEQ ID NO:15, or residue 121, 122, 123, 124, 125, 126, 127, 128, 129, 130, 131, 132, or 133 of SEQ ID NO:17 or SEQ ID NO:19; $x_3$ is residue 164, 165, 166, 167, 168, 169, 170, 171, 172, 173, 174, 175, 176, or 177 of SEQ ID NO:15, or residue 165, 166, 167, 168, 169, 170, 171, 172, 173, 174, 175, 176, 177, or 178 of SEQ ID NO:17 or SEQ ID NO:19; $x_4$ is residue 214, 215, 216, 217 or 218 of SEQ ID NO:15, or residue 215, 216, 217, 218 or 219 of SEQ ID NO:17 or SEQ ID NO:19; $x_5$ is residue 266, 267, 268, 269 or 270 of SEQ ID NO:15, or residue 268, 269, 270, 271 or 272 of SEQ ID NO:17 or SEQ ID NO:19; $x_6$ is residue 326, 327, 328, 329 or 330 of SEQ ID NO:15, or residue 328, 329, 330, 331 or 332 of SEQ ID NO:17 or SEQ ID NO:19; $x_7$ is residue 402, 403, 404, 405 or 406 of SEQ ID NO:15, or residue 404, 405, 405, 407 or 408 of SEQ ID NO:17 or SEQ ID NO:19; and $x_8$ is an amino acid residue corresponding to the C-terminus of the heme domain of CYP102A1, CYP102A2 or CYP102A3 or the C-terminus of SEQ ID NO:15, SEQ ID NO:17 or SEQ ID NO:19.

In some embodiments, the polypeptides can comprise a general structure from N-terminus to C-terminus: (segment 1)-(segment 2)-(segment 3)-(segment 4)-(segment 5)-(segment 6)-(segment 7)-(segment 8)-reductase domain, wherein segment 1 comprises an amino acid sequence from about residue 1 to about $x_1$ of SEQ ID NO:15 ("1"), SEQ ID NO:17 ("2") or SEQ ID NO:19 ("3") and having about 1-10 conservative amino acid substitutions; segment 2 is from about amino acid residue $x_1$ to about $x_2$ of SEQ ID NO:15 ("1"), SEQ ID NO:17 ("2") or SEQ ID NO:19 ("3") and having about 1-10 conservative amino acid substitutions; segment 3 is from about amino acid residue $x_2$ to about $x_3$ of SEQ ID NO:15 ("1"), SEQ ID NO:17 ("2") or SEQ ID NO:19 ("3") and having about 1-10 conservative amino acid substitutions; segment 4 is from about amino acid residue $x_3$ to about $x_4$ of SEQ ID NO:15 ("1"), SEQ ID NO:17 ("2") or SEQ ID NO:19 ("3") and having about 1-10 conservative amino acid substitutions; segment 5 is from about amino acid residue $x_4$ to about $x_5$ of SEQ ID NO:15 ("1"), SEQ ID NO:17 ("2") or SEQ ID NO:19 ("3") and having about 1-10 conservative amino acid substitutions; segment 6 is from about amino acid residue $x_5$ to about $x_6$ of SEQ ID NO:15 ("1"), SEQ ID NO:17 ("2") or SEQ ID NO:19 ("3") and having about 1-10 conservative amino acid substitutions; segment 7 is from about amino acid residue $x_6$ to about $x_7$ of SEQ ID NO:15 ("1"), SEQ ID NO:17 ("2") or SEQ ID NO:19 ("3") and having about 1-10 conservative amino acid substitutions; and segment 8 is from about amino acid residue $x_7$ to about $x_8$ of SEQ ID NO:15 ("1"), SEQ ID NO:17 ("2") or SEQ ID NO:19 ("3") and having about 1-10 conservative amino acid substitutions;

wherein: $x_1$ is residue 62, 63, 64, 65 or 66 of SEQ ID NO:15, or residue 63, 64, 65, 66 or 67 of SEQ ID NO:17 or SEQ ID NO:19; $x_2$ is residue 120, 121, 122, 123, 124, 125, 126, 127, 128, 129, 130, 132 or 132 of SEQ ID NO:15, or residue 121, 122, 123, 124, 125, 126, 127, 128, 129, 130, 131, 132, or 133 of SEQ ID NO:17 or SEQ ID NO:19; $x_3$ is residue 164, 165, 166, 167, 168, 169, 170, 171, 172, 173, 174, 175, 176, or 177 of SEQ ID NO:15, or residue 165, 166, 167, 168, 169, 170, 171, 172, 173, 174, 175, 176, 177, or 178 of SEQ ID NO:17 or SEQ ID NO:19; $x_4$ is residue 214, 215, 216, 217 or 218 of SEQ ID NO:15, or residue 215, 216, 217, 218 or 219 of SEQ ID NO:17 or SEQ ID NO:19; $x_5$ is residue 266, 267, 268, 269 or 270 of SEQ ID NO:15, or residue 268, 269, 270, 271 or 272 of SEQ ID NO:17 or SEQ ID NO:19; $x_6$ is residue 326, 327, 328, 329 or 330 of SEQ ID NO:15, or residue 328, 329, 330, 331 or 332 of SEQ ID NO:17 or SEQ ID NO:19; $x_7$ is residue 402, 403, 404, 405 or 406 of SEQ ID NO:15, or residue 404, 405, 405, 407 or 408 of SEQ ID NO:17 or SEQ ID NO:19; and $x_8$ is an amino acid residue corresponding to the C-terminus of the heme domain of CYP102A1, CYP102A2 or CYP102A3 or the C-terminus of SEQ ID NO:15, SEQ ID NO:17 or SEQ ID NO:19.

The Chimera reference table below provides exemplary sequences associated with the chimeras described herein.

Chimera reference table: Exemplary segments and segment sequences

| Position | Parent | Sequence (amino acid) |
|---|---|---|
| 1 | A1 | TIKEMPQPKTFGELKNLPLLNTDKPVQALMKIADELGEIFKFEAPGRVTRYLSSQRLIKE ACDE (SEQ ID NO: 20) |
| 1 | A2 | KETSPIPQPKTFGPLGNLPLIDKDKPTLSLIKLAEEQGPIFQIHTPAGTTIVVSGHELVKEV CDE (SEQ ID NO: 21) |
| 1 | A3 | KQASAIPQPKTYGPLKNLPHLEKEQLSQSLWRIADELGPIFRFDFPGVSSVFVSGHNLVA EVCDE (SEQ ID NO: 22) |
| 2 | A1 | SRFDKNLSQALKFVRDFAGDGLATSWTHEKNWKKAHNILLPSFSQQAMKGYHAMMVD I (SEQ ID N0: 23) |
| 2 | A2 | ERFDKSIEGALEKVRAFSGDGLATSWTHEPNWRKAHNILMPTFSQRAMKDYHEKMV DI (SEQ ID NO: 24) |
| 2 | A3 | KRFDKNLGKGLQKVREFGGDGLATSWTHEPNWQKAHRILLPSFSQKAMKGYHSMML DI (SEQ ID NO: 25) |
| 3 | A1 | AVQLVQKWERLNADEHIEVPEDMTRLTLDTIGLCGFNYRFNSFY (SEQ ID NO: 26) |
| 3 | A2 | AVQLIQKWARLNPNEAVDVPGDMTRLTLDTIGLCGFNYRFNSYY (SEQ ID NO: 27) |
| 3 | A3 | ATQLIQKWSRLNPNEEIDVADDMTRLTLDTIGLCGFNYRFNSFY (SEQ ID NO: 28) |
| 4 | A1 | RDQPHPFITSMVRALDEAMNKLQRANPDDPAYDENKRQFQEDIKVMNDLV (SEQ ID NO: 29) |
| 4 | A2 | RETPHPFINSMVRALDEAMHQMQRLDVQDKLMVRTKRQFRYDIQTMFSLV (SEQ ID NO: 30) |
| 4 | A3 | RDSQHPFITSMLRALKEAMNQSKRLGLQDKMMVKTKLQFQKDIEVMNSLV (SEQ ID NO: 31) |
| 5 | A1 | DKIIADRKASGEQ, SDDLLTHMLNGKDPETGEPLDDENIRYQIITFLIAGHET (SEQ ID NO: 32) |
| 5 | A2 | DSIIAERRANGDQDEKDLLARMLNVEDPETGEKLDDENIRFQIITFLIAGHET (SEQ ID NO: 33) |
| 5 | A3 | DRMIAERKANPDENIKDLLSLMLYAKDPVTGETLDDENIRYQIITFLIAGHET (SEQ ID NO: 34) |
| 6 | A1 | TSGLLSFALYFLVKNPHVLQKAAEEAARVLVDPVPSYKQVKQLKYVGMVLNEALRL WPTAA (SEQ ID NO: 35) |
| 6 | A2 | TSGLLSFATYFLLKHPDKLKKAYEEVDRVLTDAAPTYKQVLELTYIRMILNESLRLWPT A (SEQ ID NO: 36) |
| 6 | A3 | TSGLLSFAIYCLLTHPEKLKKAQEEADRVLTDDTPEYKQIQQLKYIRMVLNETLRLYPT A (SEQ ID NO: 37) |
| 7 | A1 | PAFSLYAKEDTVLGGEYPLEKGDELMVLIPQLHRDKTIWGDDVEEFRPERFENPSAIPQ HAFKPFGNGQRACIGQQ (SEQ ID NO: 38) |
| 7 | A2 | PAFSLYPKEDTVIGGKFPITTNDRISVLIPQLHRDRDAWGKDAEEFRPERFEHQDQVPHH AYKPFGNGQRACIGMQ (SEQ ID NO: 39) |

-continued

| Chimera reference table: Exemplary segments and segment sequences | | | |
|---|---|---|---|
| Position | Parent | | Sequence (amino acid) |
| 7 | A3 | | PAFSLYAKEDTVLGGEYPISKGQPVTVLIPKLHRDQNAWGPDAEDFRPERFEDPSSIPHH AYKPFGNGQRACIGMQ (SEQ ID NO: 40) |
| 8 | A1 | | FALHEATLVLGMMLKHFDFEDHTNYELDIKETLTLKPEGFVVKAKSKKIPLGGIPSPST (SEQ ID NO: 41) |
| 8 | A2 | | FALHEATLVLGMILKYFTLIDHENYELDIKQTLTLKPGDFHISVQSRHQEAIHADVQAA E (SEQ ID NO: 42) |
| 8 | A3 | | FALQEATMVLGLVLKHFELINHTGYELKIKEALTIKPDDFKITVKPRKTAAINVQRKEQA A (SEQ ID NO: 43) |

The disclosure provides methods for synthesizing modified sugars and oligosaccharides, polypeptides useful for generating such modified sugars and oligosaccharides and polynucleotides encoding such polypeptides.

As used herein an "oligosaccharide" refers generally to a saccharide polymer containing a number of component sugars, typically 2 to 10 or more (e.g., 3, 4, 5, 6, 7, 8, or 9 or more).

"Amino acid" is a molecule having the structure wherein a central carbon atom (the -carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond, and occurs when the carboxyl carbon atom of the carboxylic acid group bonded to the -carbon of one amino acid (or amino acid residue) becomes covalently bound to the amino nitrogen atom of amino group bonded to the -carbon of an adjacent amino acid. The term "protein" is understood to include the terms "polypeptide" and "peptide" (which, at times may be used interchangeably herein) within its meaning. In addition, proteins comprising multiple polypeptide subunits (e.g., heme and FAD domain) or other components (for example, an RNA molecule, as occurs in telomerase) will also be understood to be included within the meaning of "protein" as used herein. Similarly, fragments of proteins and polypeptides are also within the scope of the disclosure and may be referred to herein as "proteins." In one aspect of the disclosure, a stabilized protein comprises a chimera of two or more parental peptide segments.

"Peptide segment" refers to a portion or fragment of a larger polypeptide or protein. A peptide segment need not on its own have functional activity, although in some instances, a peptide segment may correspond to a domain of a polypeptide wherein the domain has its own biological activity. A stability-associated peptide segment is a peptide segment found in a polypeptide that promotes stability, function, or folding compared to a related polypeptide lacking the peptide segment. A destabilizing-associated peptide segment is a peptide segment that is identified as causing a loss of stability, function or folding when present in a polypeptide.

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Fused," "operably linked," and "operably associated" are used interchangeably herein to broadly refer to a chemical or physical coupling of two otherwise distinct domains, wherein each domain has independent biological function. As such, the present disclosure provides heme and reductase domains that are fused to one another such that they function as a holo-enzyme. A fused heme and reductase domain can be connected through peptide linkers such that they are functional or can be fused through other intermediates or chemical bonds. For example, a heme domain and a reductase domain can be part of the same coding sequence, each domain encoded by a heme and reductase polynucleotide, wherein the polynucleotides are in frame such that the polynucleotide when transcribed encodes a single mRNA that when translated comprises both domains (i.e., a heme and reductase domain) as a single polypeptide. Alternatively, both domains can be separately expressed as individual polypeptides and fused to one another using chemical methods. Typically, the coding domains will be linked "in-frame" either directly of separated by a peptide linker and encoded by a single polynucleotide. Various coding sequences for peptide linkers and peptide are known in the art and can include, for example, sequences having identity to the linker sequence separating the domains in the wild-type P450 enzymes.

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the disclosure can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA. Polynucleotides encoding P450 from *Bacillus megaterium* see e.g., GenBank accession no. J04832 and *subtilis* are known.

"Nucleic acid segment," "oligonucleotide segment" or "polynucleotide segment" refers to a portion of a larger polynucleotide molecule. The polynucleotide segment need not correspond to an encoded functional domain of a protein; however, in some instances the segment will encode a functional domain of a protein. A polynucleotide segment can be about 6 nucleotides or more in length (e.g., 6-20, 20-50, 50-100, 100-200, 200-300, 300-400 or more nucleotides in length). A stability-associated peptide segment can be encoded by a stability-associated polynucleotide segment, wherein the peptide segment promotes stability, function, or folding compared to a polypeptide lacking the peptide segment.

"Chimera" refers to a combination of at least two segments of at least two different parent proteins. As appreciated by one of skill in the art, the segments need not actually come from each of the parents, as it is the particular sequence that is relevant, and not the physical nucleic acids themselves. For example, a chimeric P450 will have at least two segments from two different parent P450s. The two segments are connected so as to result in a new P450. In other words, a protein will not be a chimera if it has the identical sequence of either one of the parents. A chimeric protein can comprise more than two segments from two different parent proteins. For example, there may be 2, 3, 4, 5-10, 10-20, or more parents for each final chimera or library of chimeras. The segment of each parent enzyme can be very short or very long, the segments can range in length of contiguous amino acids from 1 to the entire length of the protein. In one embodiment, the minimum length is 10 amino acids. In one embodiment, a single crossover point is defined for two parents. The crossover location defines where one parent's amino acid segment will stop and where the next parent's amino acid segment will start. Thus, a simple chimera would only have one crossover location where the segment before that crossover location would belong to one parent and the segment after that crossover location would belong to the second parent. In one embodiment, the chimera has more than one crossover location. For example, 2, 3, 4, 5, 6, 7, 8, 9, 10, 11-30, or more crossover locations. How these crossover locations are named and defined are both discussed below. In an embodiment where there are two crossover locations and two parents, there will be a first contiguous segment from a first parent, followed by a second contiguous segment from a second parent, followed by a third contiguous segment from the first parent. Contiguous is meant to denote that there is nothing of significance interrupting the segments. These contiguous segments are connected to form a contiguous amino acid sequence. For example, a P450 chimera from CYP102A1 (hereinafter "A1") and CYP102A2 (hereinafter "A2"), with two crossovers at 100 and 150, could have the first 100 amino acids from A1, followed by the next 50 from A2, followed by the remainder of the amino acids from A1, all connected in one contiguous amino acid chain. Alternatively, the P450 chimera could have the first 100 amino acids from A2, the next 50 from A1 and the remainder followed by A2. As appreciated by one of skill in the art, variants of chimeras exist as well as the exact sequences. Thus, not 100% of each segment need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids which encode for the amino acids.

"Conservative amino acid substitution" refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Reference sequence" refers to a defined sequence used as a basis for a sequence comparison. A reference sequence may be a subset of a larger sequence, for example, a segment of a full-length gene or polypeptide sequence. Generally, a reference sequence can be at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Sequence identity" means that two amino acid sequences are substantially identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share sequence identity or sequence similarity.

One example of an algorithm that is suitable for determining percent sequence identity or sequence similarity is the FASTA algorithm, which is described in Pearson, W. R. & Lipman, D. J., (1988) Proc. Natl. Acad. Sci. USA 85:2444. See also, W. R. Pearson, (1996) Methods Enzymology 266: 227-258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) J. Mol. Evol. 35:351-360. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc. Acids Res. 12:387-395).

Another example of an algorithm that is suitable for multiple DNA and amino acid sequence alignments is the CLUSTALW program (Thompson, J. D. et al., (1994) Nuc. Acids Res. 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) Proc. Natl. Acad. Sci. USA 89:10915-10919).

"Functional" refers to a polypeptide which possesses either the native biological activity of the naturally-produced proteins of its type, or any specific desired activity, for example as judged by its ability to bind to ligand molecules or carry out an enzymatic reaction.

"Heme domain" refers to an amino acid sequence capable of binding an iron-complexing structure, such as porphyrin. Generally, iron is complexed in a porphyrin ring, which may differ in side chain. For example, in *Bacillus* megatarium cytochrome p450 BM3, the porphyrin is typically protoporphyrin IX.

"Reductase domain" refers to an amino acid sequence capable of binding a flavin molecule, such as flavin adenine dinucleotide (FAD) and/or flavin adenine mononucleotide (FMN). Generally, these forms of flavin are present as a prosthetic group in the reductase domain and functions in electron transfer reactions. The domain structure of the cytochrome p450 BMS enzyme is described in Govindarag and Poulos, (1996) J. Biol. Chem. 272(12):7915-7921, incorporated herein by reference.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis).

The disclosure provides P450 BM3 mutants useful for regio-selectively deprotecting a monosaccharide. A "P450 BM3 mutant" refers to a polypeptide that contains or comprises an amino acid sequence as set forth SEQ ID NO:1, 2, 3, 4, 5, 6, 7, 8, 9, 10, 11, 12 or 13; polypeptides having substantial homology or substantial identity (e.g., 60, 70, 80, 90, 92, 94, 96, 97, 98, 99 or 99.5% identity) to the sequences set forth in SEQ ID Nos:1, 2, 3, 4, 5, 6, 7, 8, 9, 10, 11, 12 or 13 and that regio-selectively deprotected a monosaccharide; fragments of the foregoing sequences; and conservative variants of the foregoing. Accordingly, the disclosure provides a polypeptide comprising a sequence selected from the group consisting of SEQ ID Nos:1, 2, 3, 4, 5, 6, 7, 8, 9, 10, 11 and 12. In another aspect, the disclosure provides polypeptides obtained from a directed SCHEMA recombination library to generate cytochrome p450 chimeric enzymes based on member of this diverse enzyme family, cytochrome P450 BM3 (CYP102A1, or "A1"; SEQ ID NO:15; see also GenBank Accession No. J04832, which is incorporated herein by reference) from *Bacillus megaterium*. SCHEMA is a computational based method for predicting which fragments of homologous proteins can be recombined without affecting the structural integrity of the protein (see, e.g., Meyer et al., (2003) Protein Sci., 12:1686-1693). This computational is used to identify recombination points in the heme domain of the cytochrome p450 enzyme, thereby allowing the formation of a library of heme domain polypeptides, where each polypeptide comprises two to eight segments. Segments can comprise any two or more (e.g., three) of the naturally occurring cytochrome p450 variants, CYP102A1, CYP102A2, and CYP102A3, or mutants thereof. Chimeras with higher stability are identifiable by determining the additive contribution of each segment to the overall stability, either by use of linear regression of sequence-stability data, or by reliance on consensus analysis of the MSAs of folded versus unfolded proteins. SCHEMA recombination ensures that the chimeras retain biological function and exhibit high sequence diversity by conserving important functional residues while exchanging tolerant ones.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999) (each of which is incorporated by reference).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" Proc. Natl. Acad. Sci. USA, 83:7177-7181) (each of which is incorporated by reference). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardaye et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter (each of which is incorporated by reference).

P450 polynucleotides, including nucleotide sequences that encode P450 polypeptides and variants thereof, fragments of P450 polypeptides, related fusion proteins, or functional equivalents thereof, are used in recombinant DNA molecules that direct the expression of the P450 polypeptides in appropriate host cells, such as bacterial cells. Due to the inherent degeneracy of the genetic code, other nucleic acid sequences which encode substantially the same or a functionally equivalent amino acid sequence can also be used to clone and express the P450 polynucleotides. The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218; incorporated by reference herein). Methodology for optimizing a nucleotide sequence for expression in a plant is provided, for example, in U.S. Pat. No. 6,015,891, and the references cited therein (incorporated herein by reference).

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a polynucleotide of the disclosure has been inserted, in a forward or reverse orientation. In one aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the disclosure are provided. In other embodiments, host cells transfected with a nucleic acid molecule of the disclosure, or a vector that includes a nucleic acid molecule of the disclosure, are provided. Host cells include eukaryotic cells such as yeast cells, insect cells, or animal cells. Host cells also include prokaryotic cells such as bacterial cells.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express an inventive protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc.

In bacterial systems, a number of expression vectors may be selected depending upon the use intended for the P450 polypeptide. For example, when large quantities of P450 polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the P450 polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the P450 polypeptides of the invention. For reviews, see Ausubel (supra) and Grant et al. (1987) Methods in Enzymology 153:516-544 (incorporated herein by reference).

Also provided are engineered host cells that are transduced (transformed or transfected) with a vector provided herein (e.g., a cloning vector or an expression vector), as well as the production of polypeptides of the disclosure by recombinant techniques. The vector may be, for example, a plasmid, a viral particle, a phage, etc. The engineered host cells can be cultured in conventional nutrient media modified as appropriate for activating promoters, selecting transformants, or amplifying the P450 homologue gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In other embodiments, methods for producing a cell that selectively deprotects a saccharide, are provided. Such methods generally include: (a) transforming a cell with an isolated nucleic acid molecule encoding a polypeptide of the disclosure (e.g., SEQ ID NO: 1, 2, 3, 4, 5, 6, 7, 8, 9, 10, 11, 12, or 13).

In other embodiments, methods for selecting a cell that selectively deprotects a monosaccharide, are provided. The methods generally include: (a) providing a cell containing a nucleic acid construct that includes a nucleotide sequence that encodes a modified cytochrome P450 polypeptide, the nucleic acid molecule encoding a polypeptide comprising an amino acid sequence set forth in SEQ ID NO: 1, 2, 3, 4, 5, 6, 7, 8, 9, 10, 11, 12, 13 and polypeptide having 1-20 conservative substitutions thereto. The methods further include (b) culturing the cell in the presence of a suitable substrate and under conditions where the modified cytochrome P450 is expressed at an effective level; and (c) detecting the production of a modified deprotected monosaccharide.

In other embodiments, methods for producing an alcohol, are provided. The methods include: (a) providing a cell containing a nucleic acid construct comprising a nucleotide sequence that encodes a modified cytochrome P450 polypeptide, the nucleotide sequence selected from: (i) a nucleic acid molecule encoding a polypeptide comprising an amino acid sequence set forth in SEQ ID NO: 1, 2, 3, 4, 5, 6, 7, 8, 9, 10, 11, 12 or 13; (ii) a nucleic acid molecule encoding a polypeptide of the disclosure; or (iii) a nucleic acid molecule of the disclosure. The methods further include (b) culturing the cell in the presence of a suitable alkane and under conditions where the modified cytochrome P450 is expressed at an effective level; and (c) deprotecting a protected monosaccharide by hydroxylation.

A mutant cytochrome P450 can be expressed in its functional form in *Escherichia coli* and the whole cell conversion of a protected carbohydrate or monosaccharide to a deprotected form using optimized versions of these enzymes in *E. coli* will be possible. As demonstrated in the examples provided herein, *Escherichia coli* expressing mutant BM-3 enzymes will act as whole cell biocatalysts with relative activities equivalent to the activities of the individual BM-3 catalyst. Further, the metabolism of host organisms can be engineered to further increase the levels of NADPH (or NADH for BM-3 variants that accept NADH) available to biocatalysts provided herein.

Enzymes applied in this disclosure are P450 BM3 variants including, but not limited to, 9-10A (SEQ ID NO:1), 9-10A F87A (SEQ ID NO:2), 9-10A F87V (SEQ ID NO:3), 9-10A F87I (SEQ ID NO:4), 9-10A A82L (SEQ ID NO:5), 9-10A A82F (SEQ ID NO:6), 9-10A F87V A82G A328V (12-10C, SEQ ID NO:7), 9-10A F87V A82G A328L A78T (23-11B, SEQ ID NO:8), 21313313 (SEQ ID NO:9), 9-10A F87A C47R I94K, 9-10A F87A C47R I94K F81W A82S, 9-10A C47R A78L F87A I94K A180V V184T A330V (E12r12, SEQ ID NO:12), and 9-10A C47R A78L F87A I94K I263M V184T A330V (B1, SEQ ID NO:13).

TABLE 1

Active monooxygenases for methylated sugar compounds described.

| | |
|---|---|
| 9-10A | SEQ ID NO: 1 |
| 9-10A F87A | SEQ ID NO: 2 |
| 9-10A F87V | SEQ ID NO: 3 |
| 9-10A F87I | SEQ ID NO: 4 |
| 9-10A A82L | SEQ ID NO: 5 |
| 9-10A A82F | SEQ ID NO: 6 |
| 9-10A F87V A82G A328V (12-10C) | SEQ ID NO: 7 |
| 9-10A F87V A82G A328L A78T (23-11B) | SEQ ID NO: 8 |
| 21313313 | SEQ ID NO: 9 |
| 9-10A F87A C47R I94K | SEQ ID NO: 10 |
| 9-10A F87A C47R I94K 81W 82S | SEQ ID NO: 11 |
| 9-10A C47R A78L F87A I94K A180V V184T A330V (E12r12) | SEQ ID NO: 12 |
| 9-10A C47R A78L F87A I94K I263M V184T A330V (B1) | SEQ ID NO: 13 |

Mutant P450 9-10A and 9-10A derivatives having mutations at Phe87, Ala82, Ala328 and Ala78, and 21313313, a chimeric P450, and other variants of 9-10A F87A are useful. Enzymes included as derivatives of these enzymes can be utilized for the dealkylation reaction.

Figure 2:
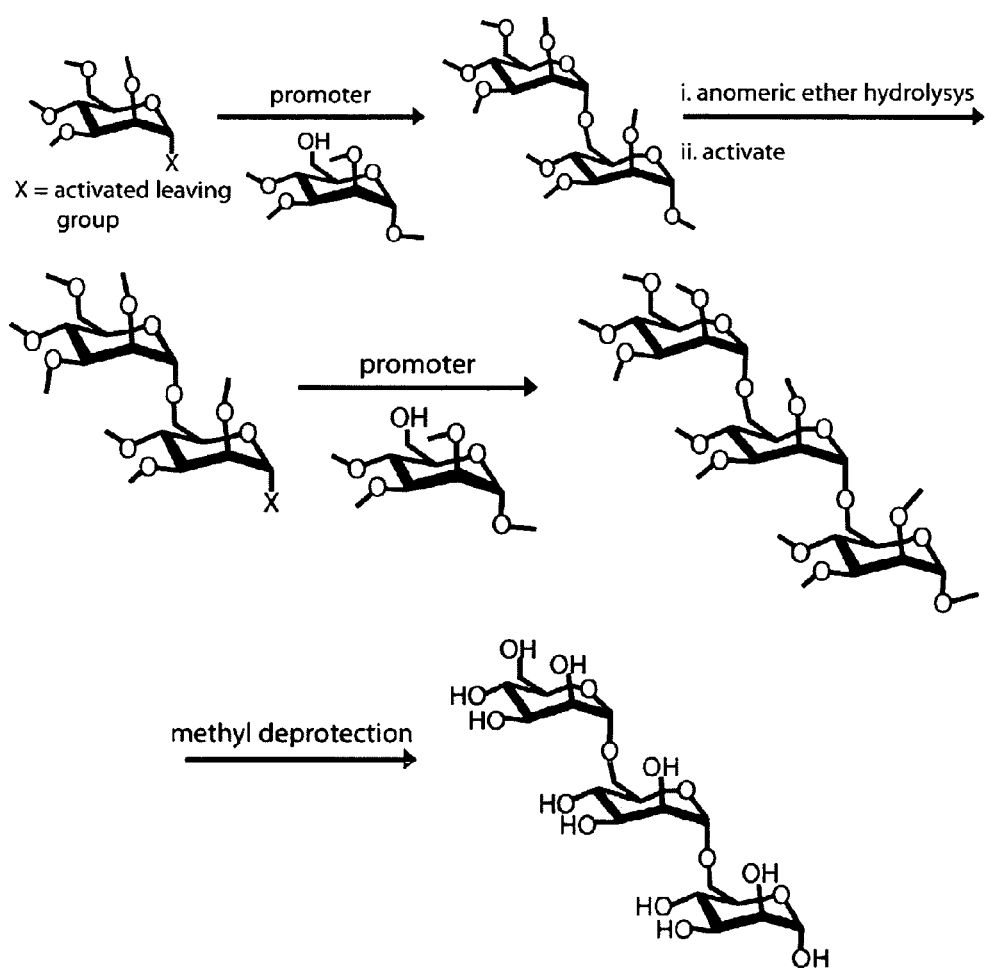
FIG. 2 shows an example of how the reaction is used in the synthesis of oligosaccharides, in this case mannotriose. X=an activated leaving group such as halide, trichloroacetimidate, actyl and thioether.

Four mutant derivatives were examined and are exemplified herein. Other derivatives will be apparent to those of skill in the art based upon the teachings herein. For mutants comprising (i) 9-10A F87I, (ii) 9-10A F87V A82G A328V (12-10C), (iii) 9-10A C47R A78L F87A I94K A180V V184T A330V (E12r12), and (iv) 9-10A C47R A78L F87A I94K I263M V184T A330V (B1) were shown to possess high regio-selectivities and total turnover numbers (TTN) with certain permethylated monosaccharides. The selectivity was higher than 90% for the C6 position when either 9-10A F87V or 12-10C was applied to 1, 2,3,4,6 pentamethyla-D-mannopyranoside, and higher than 85% for the C4 position when 9-10A F87I was applied to 1-benzyl 2, 3,4,6 tetramethylβ-D-glucopyranoside. On the other hand, B1 and E12 demethylated 1-benzoyl-2,3,4,6-tetramethyl-β-D-galctopyranoside (C3) and 1,2,3,4,6-β-D-pentamethylgalactopyranoside (C2) respectively had greater than 95% regio-selectivity. Generally, no second demethylation occurred when a fully methylated carbohydrate such as 1,2,3,4,6 pentamethyla-D-glucopyranoside, 1,2,3,4,6 pentamethyla-D-galactopyranoside and 1,2,3,4,6 pentamethyla-D-mannopyranoside were used as substrates. There also was significant difference in substrate preference among permethylated monosaccharides, such as 1,2,3,4,6 pentamethyla-D-glucopyranoside, 1,2,3,4,6 pentamethyla-D-galactopyranoside and 1,2,3,4,6 pentamethyla-D-mannopyranoside, as shown in FIG. 2. These results show that mutations to these enzymes can significantly alter substrate specificity or substrate preference, by substitution of amino acid residues in the protein surrounding the active site. In one aspect, the mutation sites include Phe87, Ala82, Ala328 and Ala78.

Methods of screening for mutant enzymes can be used in the methods of the disclosure or to identify the activity of mutant P450 polypeptides are provide. For example, directed evolution can be used to alter the substrate specificity of the monooxygenase. This is accomplished by screening mutated enzymes on selected substrates, using a high throughput assay such as the Purpald assay described herein, or measuring the product distribution by gas chromatography, or a combination of these methods.

The disclosure is applicable for gram scale production of a selectively de-protected carbohydrate. Regio-selectively monodeprotected products have been obtained with greater than 90% purity, in over 1 mg per ml reaction mixture. In these reactions the cofactor NADPH was regenerated using an enzyme-coupled regeneration system such as glucose 6-phosphate dehydrogenase. Glucose dehydrogenase, formate dehydrogenase, isocitrate dehydrogenase, can also be used for cofactor regeneration. Reagents such as superoxide dismutase, catalase or other reductive agents can be used to prevent enzyme inactivation from reactive oxygen species, to enhance the productivity. In vivo conversion methods such as that shown in Lu, Y. et al. 2006 may be utilized as well. The dealkylated products may be isolated by extracting in organic solvents such as dichloromethane or ethylacetate.

The following examples are intended to illustrate but not limit the disclosure. While they are typical of those that might be used, other procedures known to those skilled in the art may alternatively be used.

EXAMPLES

Example 1

Figure 1C:
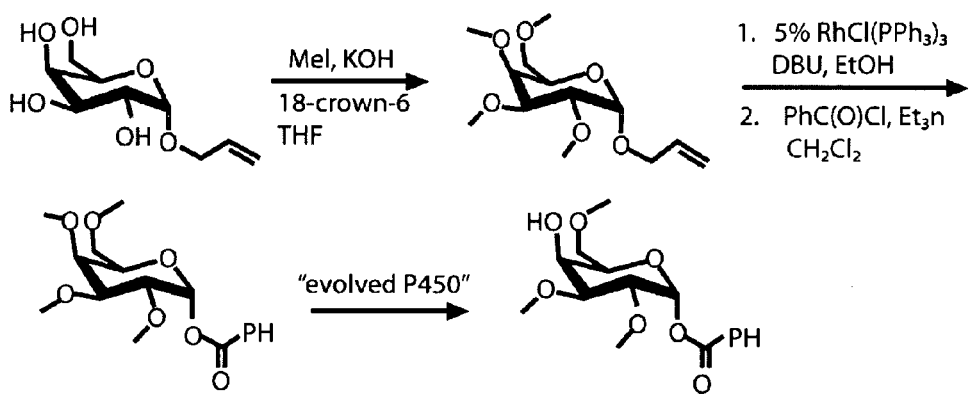
Figure 1D:
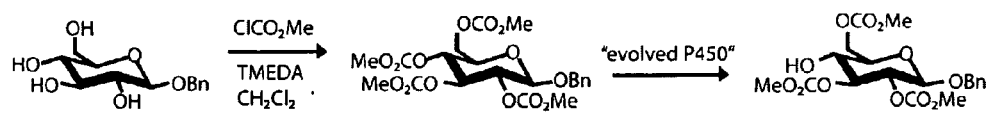
Figure 3:
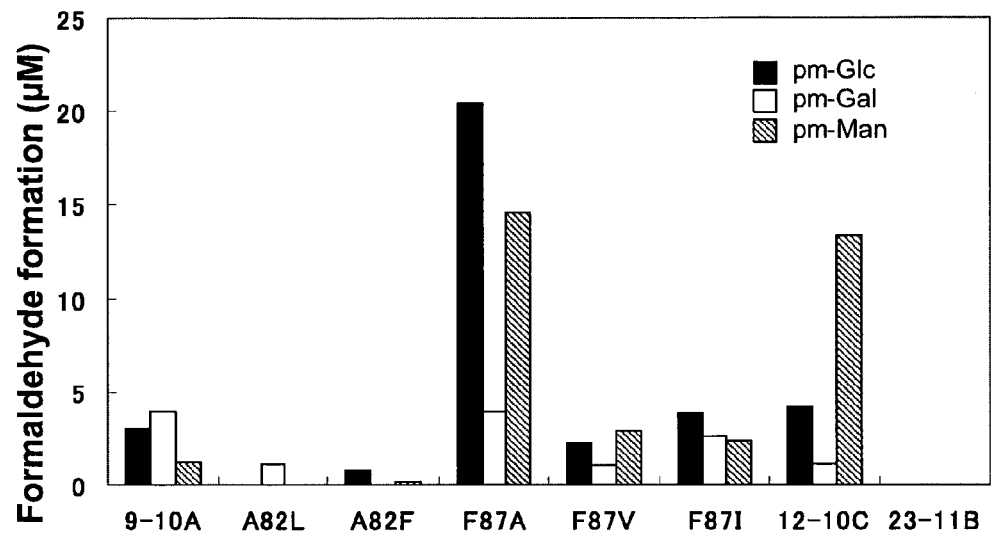
FIG. 3 shows the deprotection activity of P450 holoenzymes for 1,2,3,4,6 pentamethyl-α-D-glucopyranoside (pm-Glc), 1,2,3,4,6 pentamethyl-α-D-galactopyranoside (pm-Gal) and 1,2,3,4,6 pentamethyl-α-D-mannopyranoside (pm-Man). Reaction conditions were 1 mM substrate, 0.2 µM enzyme, 5 mM NADPH, 100 mM potassium phosphate, pH 8.0, 25° C., 30 min, 1 ml in a 24 well-plate, shaking at 170 rpm on Kuhner ISF-1-W. The formaldehyde deprotection product was analyzed by adding 50 µl of 168 mM Purpald in 2N NaOH solution to 200 µl of reaction mixture, and measuring $A_{550}$ after 15 min at room temperature.
Figure 4:
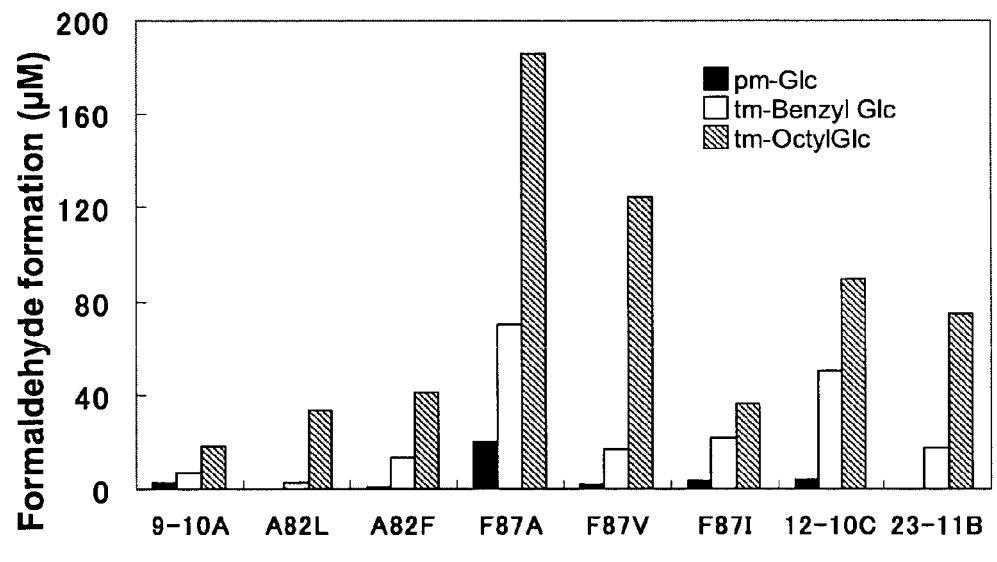
FIG. 4 shows the deprotection activity of P450 holoenzymes for 1,2,3,4,6 pentamethyl-α-D-glucopyranoside (pm-Glc), 1-benzyl 2,3,4,6 tetramethyl-β-D-glucopyranoside (tm-Benzyl Glc) and 1-octyl 2,3,4,6 tetramethyl β-D-glucopyranoside (tm-OctylGlc). Reaction conditions were 1 mM substrate, 0.2 µM enzyme, 5 mM NADPH, 100 mM potassium phosphate, pH 8.0, 25° C., 30 min, 1 ml in a 24 well-plate, shaking at 170 rpm on Kuhner ISF-1-W. The formaldehyde deprotection product was analyzed by adding 50 µl of 168 mM Purpald in 2 N NaOH solution to 200 µl of reaction mixture, and measuring $A_{550}$ after 15 min at room temperature.

Screening to identify monooxygenases that are active on methylated carbohydrates. Cytochrome P450 mutant libraries developed from CYP102A1 and also the recombination of CYP102A1, CYP102A2, CYP012A3 were screened by detection of the formaldehyde product by reaction with the calorimetric reagent Purpald. The assay was carried out by mixing lysate of E. coli DH5α expressing the particular protein with 0.5 mM permethylated sugar molecules in presence of 0.4 mM NADPH in a total volume of 200 µl. E. coli lysate containing the enzyme in 0.1 M potassium phosphate buffer pH 8.0 was prepared by the method described in (Glieder et al. 2003). After 40 min reaction at room temperature, 50 µl of 168 mM Purpald solution in 2N NaOH was added. The amount of formaldehyde product was determined by measuring the absorbance at 550 nm 1 hour after the addition of Purpald. The methylated carbohydrates used for this screen were 1,2,3,4,6-pentamethyl-α-D-glucopyranoside, 1,2,3,4, 6-pentamethyl-α-D-galactopyranoside, 1,2,3,4,6-pentamethyl-α-D-mannopyranoside, 1-benzyl-2,3,4,6-tetramethyl-β-D-glucopyranoside and 1-octyl-2,3,4,6-tetramethyl-β-D-glucopyranoside. These compounds were prepared from methyl α-D-glucopyranoside, methyl-β-D-galactopyranoside, methyl β-D-mannopyranoside, methyl β-D-glucopyranoside, 1-benzyl β-D-glucopyranoside, 1-octyl β-D-glucopyranoside, respectively, by reaction with methyl iodide in 50% aqueous NaOH in dimethylsulfoxide. Using this screen, nine BM3 variants were found to be active for deprotection of the methylated sugar compounds, as shown in Table 1. Their substrate preferences, determined as described below, are shown in FIG. 3 and FIG. 4. An additional substrate, 1-benzoyl-2,3,4,6,-tetramethyl-β-D-galacto-pyranoside, was synthesized as shown in FIG. 1C and screened in an analogous fashion in later efforts.

Example 2

Figure 5:
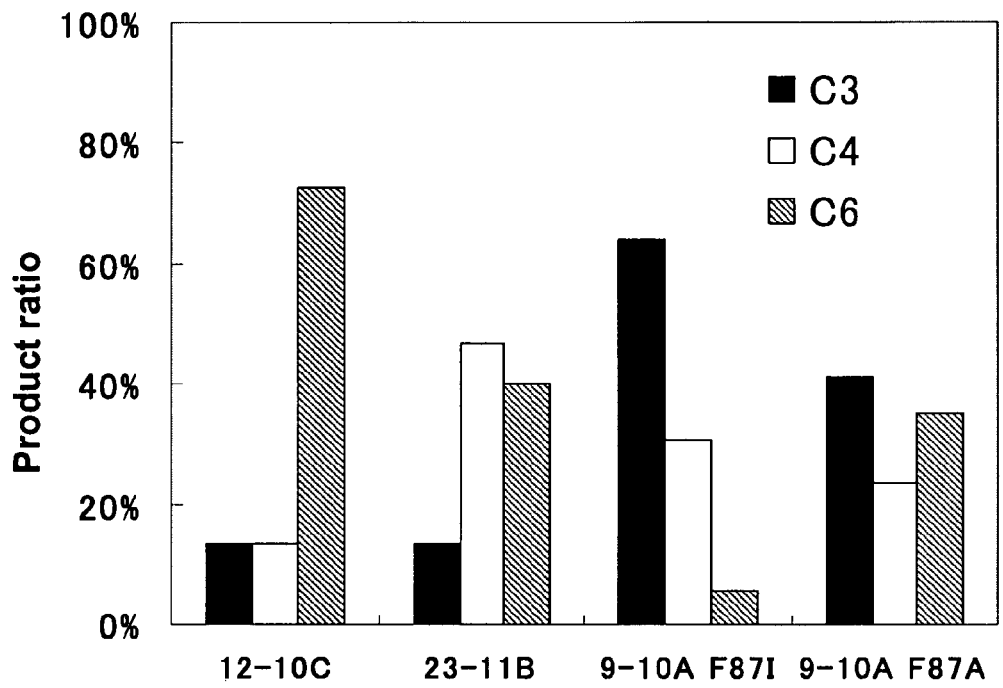
FIG. 5 shows the distribution of de-protected 1, 2,3,4,6 pentamethyl-α-D-glucopyranoside as catalyzed by P450 BM3 variants 12-10C, 23-11B, 9-10A F87I and 9-10A F87A. Reaction conditions were 1 mM substrate, 1-2 µM of purified enzyme, 5 mM NADPH, 100 mM potassium phosphate, pH 8.0, 25° C., 2 h, 1 ml in a 24 well-plate, shaking at 170 rpm on Kuhner ISF-1-W. A 20-60% conversion was obtained.
Figure 6:
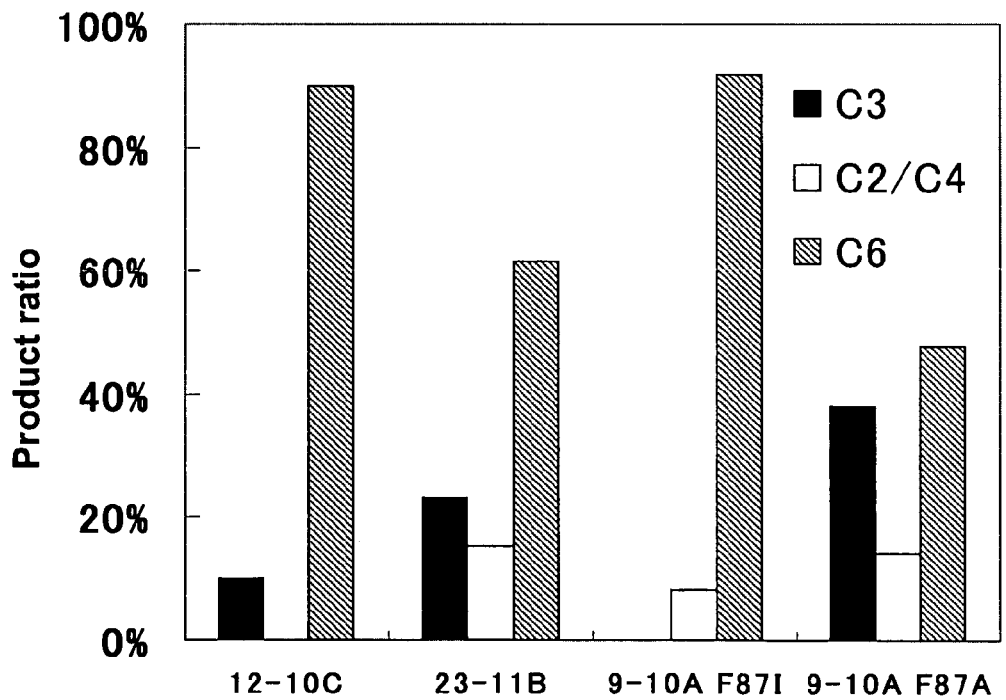
FIG. 6 shows distribution of de-protected 1,2,3,4,6 pentamethyl-α-D-mannopyranoside by P450 BM3 variants 12-10C, 23-11B, 9-10A F87I and 9-10A F87A. Reaction conditions were 1 mM substrate, 1-2 µM of purified enzyme, 5 mM NADPH, 100 mM potassium phosphate, pH 8.0, 25° C., 2 h, 1 ml in a 24 well-plate, shaking at 170 rpm on Kuhner ISF-1-W. A 20-60% conversion was obtained. C-2 and C-4 de-protected product was indistinguishable on GC analysis.
Figure 7:
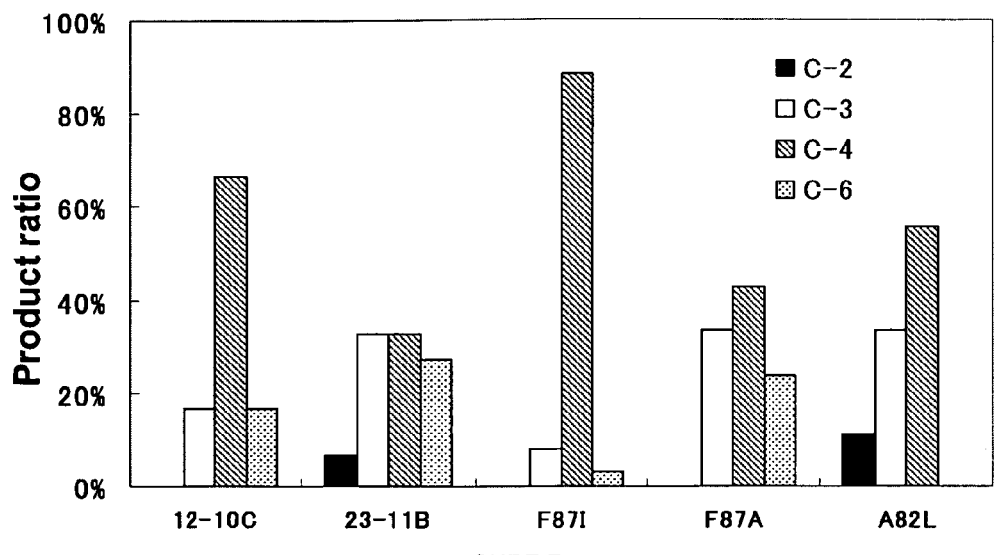
FIG. 7 shows distribution of de-protected 1-benzyl 2, 3, 4, 6 tetramethyl-β-D-glucopyranoside by P450 variants 12-10C, 23-11B, 9-10A F87I and 9-10A F87A. Reaction condition was 1 mM substrate, 1-2 µM of purified enzyme, 5 mM NADPH, 100 mM potassium phosphate, pH 8.0, 25° C., 2 h, 1 ml in a 24 well-plate, shaking at 170 rpm on Kuhner ISF-1-W. A 20-60% conversion was obtained.

Regio-specificity of screened monooxygenases. The regio-selectivity of these enzymes was analyzed as follows. The reactions were performed on 1 ml scale in 24-well plates under reaction conditions of 25° C., 2 h, shaking at 170 rpm on a Kuhner ISF-1-W, 1 mM substrate, 0.5-2 µM of enzyme, 2.5-10 mM NADPH, 100 mM potassium phosphate, pH 8.0 adjusted in 0.2-0.6 mM of formaldehyde per substrate. The product mixtures were extracted with 1 mL chloroform three times, dried over anhydrous sodium sulfate, filtered, concentrated under reduced pressure, and analyzed by GC/MS. FIG. 5, FIG. 6 and FIG. 7 show the product distributions. Notably, some of the enzymes showed high regio-selectivity. 9-10A F87I displayed >90% selectivity for demethylation at the C6 position of 1,2,3,4,6-pentamethyl β-D-mannopyranoside. The same enzyme was >90% selective for the C4 methyl group of 1-benzyl-2,3,4,6-tetramethyl β-D-glucopyranoside. 12-10C showed over 90% selectivity for C6 demethylation of 1,2,3,4,6-pentamethyl α-D-mannopyranoside. No deprotection of a second position was observed the above reactions; only monodeprotection was observed. Substrates possessing a 1-benzyl group displayed different reactivity with the same enzymes. For the 1-benzyl substrates, all of the enzymes applied here were specific for C-4 demethylation, with 9-10A F87I possessing the highest specificity.

Example 3

Figure 8:
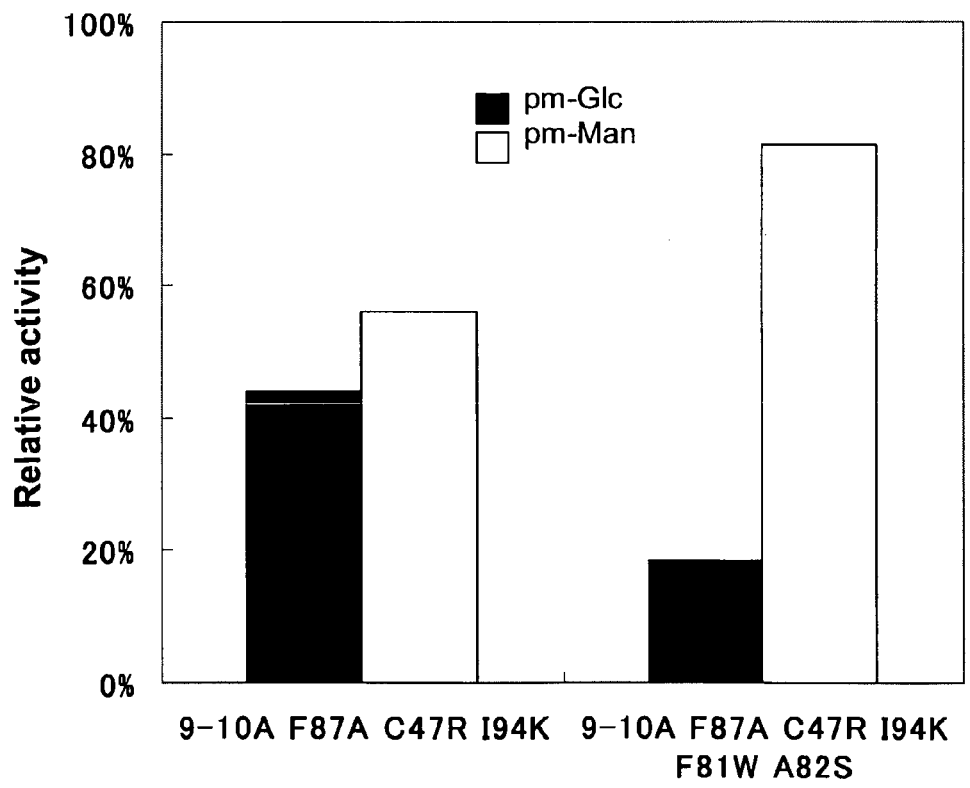
FIG. 8 shows de-protecting activity of P450 BM3 variants 9-10A F87A C47R I9K and 9-10A F87A C47R I9K I94K F81W A82S for 1,2,3,4,6 pentamethyl-α-D-glucopyranoside (pm-Glc) and 1,2,3,4,6 pentamethyl-α-D-mannopyranoside (pm-Man), as a relative value for these two substrates. The reaction conditions were 1 mM substrate, 2 µM enzyme, 5 mM NADPH, 100 mM potassium phosphate, pH 8.0, 25° C., 2 h, 1 ml in a 24 well plate, shaking at 170 rpm on Kuhner ISF-1-W. Product was assayed by gas chromatography.
Figure 9:
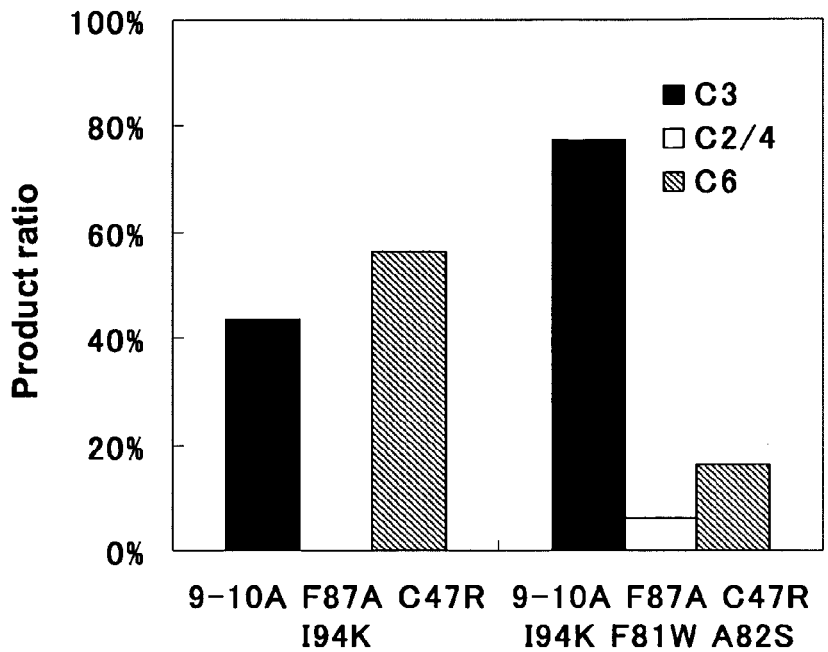
FIG. 9 shows distribution of de-protected 1,2,3,4,6 pentamethyl-α-D-mannopyranoside catalyzed by P450 BM3 variants 9-10A F87A C47R I9K and 9-10A F87A C47R I9K I94K F81W A82S. Reaction conditions were 1 mM substrate, 2 µM enzyme, 5 mM NADPH, 100 mM potassium phosphate, pH 8.0, 25° C., 2 h, 1 ml in 24 well plate, shaking at 170 rpm on Kuhner ISF-1-W. Product was assayed by gas chromatography.

Directed evolution of a specific deprotecting enzyme. The specificity of the enzyme can be altered by directed evolution as shown below. 9-10A F87A exhibited high activity for demethylation of permethylated substrates (FIG. 3). However, it did not have significant regio-selectivity. After introducing amino acid substitutions C47R and I94K (9-10A F87A C47R I94K, SEQ ID NO:10) to the enzyme to enhance stability, random mutations were introduced by error-prone PCR and screened for enzymes with specific demethylation profiles. A double mutation at amino acid positions 81, 82 was found to alter the substrate preference. By targeting residues 81, 82 by saturation mutagenesis and screening for altered regio-selectivity, monooxygenase variant 9-10A F81W C47R I94K A82S F87A (SEQ ID NO:11) was found to have 80% specificity for C3 demethylation of 1,2,3,4,6-pentamethyl α-D-mannopyranoside. This enzyme had four fold higher activity for this substrate compared to 1,2,3,4,6-pentamethyl α-D-glucopyranoside (FIGS. 8, 9). Thus, mutants with higher specificity could be screened by a method for enhanced reaction rate for one substrate over another by the simple Purpald colorimetric assay.

Example 4

Directed evolution of a specific deprotecting enzyme. A process similar to that described in Example 3 was utilized to improve the activity and regio-selectivity of an enzyme for demethylation of 1-benzoyl-2,3,4,6-β-D-tetramethyl-galactopyranoside, which was identified in a manner similar to that described in Example 1. Specifically, introduction of C47R and I94K and one round of error prone mutagenesis and screening on 9-10A A78L F87A V184T A330V (2C6) provided 9-10A C47R A78L F87A I94K I263M V184T A330V (B1). This variant provided quantitative conversion >95% selectivity for demethylation at the 3-position of the substrate.

Example 5

Directed evolution of a specific deprotecting enzyme. A process similar to that described in Example 4 was utilized to evolve an enzyme for regio-selective demethylation of 1,2,3,4,6-β-D-pentamethylgalactopyranoside. Specifically, introduction of C47R and I94K and one round of error prone mutagenesis and screening on 9-10A A78L F87A V184T A330V (2C6) provided 9-10A C47R A78L F87A I94K A111V V141I A180V V184T A330V (E12). Subsequent point mutations provided 9-10A C47R A78L A87V I94K A180V V184T A330V (E12r12A87V). This variant provided 49% conversion and >95% selectivity for demethylation at the 2-position of the substrate.

Example 6

Figure 10:
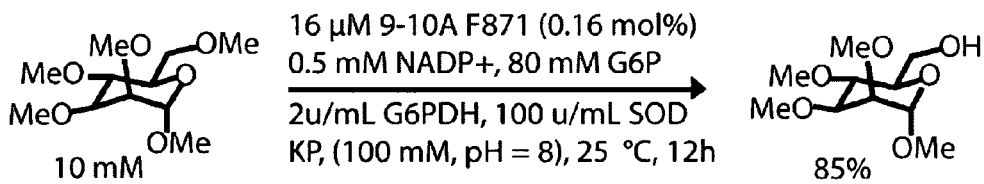
FIG. 10 shows the preparative-scale deprotection of 1,2,3,4,6pentamethyl-α-D-mannopyranoside catalyzed by P450 BM3 variant 9-10A F87I.

Preparative synthesis of selectively protected monosaccharides using a monooxygenase. 1,2,3,4-tetramethyl mannopyranoside was synthesized on preparative scale in 24-well plates, 1 ml reaction mixture, 25° C., 16 h, 210 rpm on Kuhner ISF-1-W (FIG. 10). The composition of the reaction mixture is as follows: 10 mM substrate, 16 µM 9-10A F87I, 2 U/ml glucose-6-phospate dehydrogenase, 0.5 mM NADP+, 80 mM glucose-6-phosphate, 100 U/ml superoxide dismutase, 100 mM potassium phosphate buffer, pH 8.0. The conversion of the substrate was over 95%, as determined by gas chromatography. The desired C6-demethylated product represented 92% of the product mixture, and C2 or C4-demethylated products were 8% combined. Following the reaction, the crude mixture was extracted three times with chloroform, and the pooled organic extracts were dried over $Na_2SO_4$, filtered and concentrated to afford product. Larger scale reactions were performed by replicating 1 ml reaction mixtures in 24-well plates. 10 plates of reaction were used to convert 600 mg of substrate under the same reaction conditions as shown above. A product in shaker flasks would provide better yield with less product loss to interaction with the vessel sides. A better mixing and aeration can also be provided by a shaker vessel.

Example 7

Figure 11:
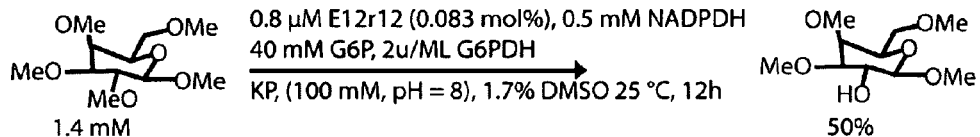
FIG. 11 shows the preparative-scale deprotection of 1,2,3,4,6 pentamethyl-β-D-galactopyranoside catalyzed by P450 BM3 variants 9-10A C47R A78L F87A I94K A180V V184T A330V (E12r12).

Preparative synthesis of selectively protected monosaccharides using a monooxygenase. 1,3,4,6-tetramethyl-β-D-galactopyranoside was synthesized on preparative scale in a 500 mL evaporation dish covered with air-permeable film with stirring at 25° C. for 12 h (FIG. 11). The composition of the reaction mixture is as follows: 1 mM 1,2,3,4,6-pentamethyl-β-D-galactopyranoside, 0.8 µM E12r12A87V, 2 U/ml glucose-6-phospate dehydrogenase, 0.5 mM NADPH, 40 mM glucose-6-phosphate, 100 U/ml superoxide dismutase, 100 mM potassium phosphate buffer, pH 8.0. A single product was observed for form by gas chromatography and identified as 1,3,4,6-tetramethyl-β-D-galactopyranoside by comparison to an authentic standard. The reaction mixture was saturated with NaCl, 150 mL $CH_2Cl_2$ was added, and the mixture was stirred for approximately 15 min. The mixture was poured into a separatory funnel and the organic phase was separated. The aqueous phase was extracted with 4×50 mL $CH_2Cl_2$. The organic phases were combined, dried over MgSO$_4$, filtered, and concentrated. The crude product was purified by chromatography (SiO$_2$, EtOAc/hexanes) to provide the desired product.

Example 8

Figure 12:
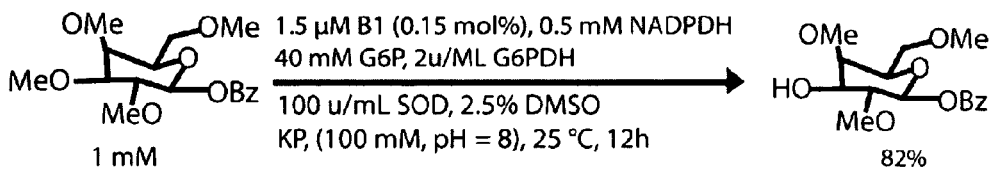
FIG. 12 shows the preparative-scale deprotection of 1-benzoyl-2,3,4,6-pentamethyl β-D-galactopyranoside catalyzed by P450 BM3 variants 9-10A C47R A78L F87A I94K I263M V184T A330V (B1).

Preparative synthesis of selectively protected monosaccharides using a monooxygenase. 1-benzoyl-2,4,6-trimethyl-β-D-galactopyranoside was synthesized on preparative scale in an identical fashion described in Example 7 starting with 0.1 g of 1-benzoyl-2,3,4,6-trimethyl-β-D-galactopyranoside (FIG. 12). The product was isolated in 87% yield following workup and purification as described above and the structure was confirmed by X-ray crystallography.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method for regioselective removal of alkyl ethers groups on protected peralkylated carbohydrates comprising contacting the carbohydrate with a polypeptide having at least 95% identity to a polypeptide comprising a sequence selected from the group consisting of SEQ ID NO:1, 2, 3, 4, 5, 6, 7, 8, 9, 10, 11, 12 and 13, wherein the polypeptide has monooxygenase activity, and wherein the alkyl ether is removed.

2. The method of claim 1, wherein the polypeptide having monooxygenase activity is a cytochrome P450.

3. The method of claim 2, wherein the monooxygenase comprises at least 98% sequence identity to a polypeptide comprising a sequence selected from the group consisting of SEQ ID NO:1, 2, 3, 4, 5, 6, 7, 8, 9, 10, 11, 12 and 13.

4. The method of claim 1, wherein the monooxygenase comprises a sequence as set forth in SEQ ID NO:1 and having a mutation at a position selected from the group consisting F87, A82 and a combination thereof.

5. The method of claim 4, wherein the monooxygenase comprises a mutation at F87 and A82 of SEQ ID NO:1.

6. The method of claim 5, wherein the monooxygenase further comprises a mutation at a position selected from the group consisting of A328, A78 and a combination thereof of SEQ ID NO:1.

7. The method of claim 6, wherein the monooxygenase comprises a mutation at position F87, A82 and A328 of SEQ ID NO:1.

8. The method of claim 6, wherein the monooxygenase comprises a mutation at position F87, A82, A328 and A78 of SEQ ID NO:1.

9. The method of claim 4, wherein the monooxygenase comprises a mutation at F87 of SEQ ID NO:1.

10. The method of claim 9, wherein the monooxygenase further comprises a mutation at position C47, I94, or a combination thereof of SEQ ID NO:1.

11. The method of claim 10, wherein the monooxygenase comprises a mutation at position F87, C47 and I94 of SEQ ID NO:1.

12. The method of claim 11, wherein the monooxygenase further comprises a mutation at position A78, V184, A330 or a combination thereof.

13. The method of claim 12, wherein the monooxygenase further comprises a mutation at position A180.

14. The method of claim 12, wherein the monooxygenase further comprises a mutation at position I263.

* * * * *

SEQUENCE LISTING

```
<160> NUMBER OF SEQ ID NOS: 43

<210> SEQ ID NO 1
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 1

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Cys Val
            35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285
```

```
Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
```

```
            705                 710                 715                 720
Asp Ala Ser Gln Gln Ile Arg Leu Glu Ala Glu Glu Lys Leu Ala
                    725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 2
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 2

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
```

```
            20                  25                  30
Ala Asp Glu Leu Gly Glu Ile Phe Lys Phe Glu Ala Pro Gly Cys Val
            35                  40                  45
Thr Arg Tyr Leu Ser Ser Gln Arg Leu Ile Lys Glu Ala Cys Asp Glu
50                  55                  60
Ser Arg Phe Asp Lys Asn Leu Ser Gln Ala Leu Lys Phe Ala Arg Asp
65                  70                  75                  80
Phe Ala Gly Asp Gly Leu Ala Thr Ser Trp Thr His Glu Ile Asn Trp
                    85                  90                  95
Lys Lys Ala His Asn Ile Leu Leu Pro Ser Phe Ser Gln Gln Ala Met
            100                 105                 110
Lys Gly Tyr His Ala Met Met Val Asp Ile Ala Val Gln Leu Val Gln
            115                 120                 125
Lys Trp Glu Arg Leu Asn Ala Asp Glu His Ile Glu Val Ser Glu Asp
            130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Ile Ser
                    165                 170                 175
Met Val Arg Ala Leu Asp Glu Val Met Asn Lys Leu Gln Arg Ala Asn
            180                 185                 190
Pro Asp Asp Pro Ala Tyr Asp Glu Asn Lys Arg Gln Cys Gln Glu Asp
            195                 200                 205
Ile Lys Val Met Asn Asp Leu Val Asp Lys Ile Ala Asp Arg Lys
            210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Ser Tyr
                    245                 250                 255
Gln Ile Ile Thr Phe Leu Ile Ala Gly His Glu Thr Thr Ser Gly Leu
            260                 265                 270
Leu Ser Phe Ala Leu Tyr Phe Leu Val Lys Asn Pro His Val Leu Gln
            275                 280                 285
Lys Val Ala Glu Glu Ala Ala Arg Val Leu Val Asp Pro Val Pro Ser
            290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                    325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
            355                 360                 365
Asp Asp Val Glu Glu Phe Arg Pro Glu Arg Phe Glu Asn Pro Ser Ala
            370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                    405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
            435                 440                 445
```

```
Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
                610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860
```

```
Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
        900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
        980                 985                 990

Gly Ala His Phe Tyr Ile Cys Gly Asp Gly Ser Gln Met Ala Pro Ala
            995                1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045
```

<210> SEQ ID NO 3
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 3

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Val Thr Ser Trp Thr His Glu Ile Asn Trp
            85                  90                  95

Lys Lys Ala His Asn Ile Leu Leu Pro Ser Phe Ser Gln Gln Ala Met
        100                 105                 110

Lys Gly Tyr His Ala Met Met Val Asp Ile Ala Val Gln Leu Val Gln
    115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
            165                 170                 175
```

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
            195                 200                 205

Ile Lys Val Met Asn Asp Leu Val Asp Lys Ile Ile Ala Asp Arg Lys
            210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
            245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp

-continued

```
            595                 600                 605
Phe Glu Gly Thr Tyr Glu Glu Trp Arg Glu His Met Trp Ser Asp Val
            610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Asp Met Pro Leu Ala
                    645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
            675                 680                 685
Pro Lys Glu Ala Ser Tyr Gln Glu Gly Asp His Leu Gly Val Ile Pro
            690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                    725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
            755                 760                 765
Ala Lys Thr Val Cys Pro Pro His Lys Val Glu Leu Glu Ala Leu Leu
770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                    805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
            835                 840                 845
Val Ser Gly Glu Ala Trp Ser Gly Tyr Gly Glu Tyr Lys Gly Ile Ala
850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                    885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
            915                 920                 925
Glu Ala His Leu Tyr Phe Gly Cys Arg Ser Pro His Glu Asp Tyr Leu
            930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                    965                 970                 975
His Val Met Glu Gln Asp Gly Lys Lys Leu Ile Glu Leu Leu Asp Gln
                980                 985                 990
Gly Ala His Phe Tyr Ile Cys Gly Asp Gly Ser Gln Met Ala Pro Ala
            995                 1000                1005
Val Glu Ala Thr Leu Met Lys Ser Tyr Ala Asp Val His Gln Val
    1010                1015                1020
```

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 4
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 4

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Ile Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

```
Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
            450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750
```

Val Glu Leu Gln Asp Pro Val Thr Arg Thr Gln Leu Arg Ala Met Ala
            755                 760                 765

Ala Lys Thr Val Cys Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 5
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 5

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
            35                  40                  45

Thr Arg Tyr Leu Ser Ser Gln Arg Leu Ile Lys Glu Ala Cys Asp Glu
        50                  55                  60

-continued

```
Ser Arg Phe Asp Lys Asn Leu Ser Gln Ala Leu Lys Phe Ala Arg Asp
 65                  70                  75                  80

Phe Leu Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
```

-continued

```
            485                 490                 495
Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910
```

-continued

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 6
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 6

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Phe Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

```
Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
            245                 250                 255

Gln Ile Ile Thr Phe Leu Ile Ala Gly His Glu Thr Thr Ser Gly Leu
        260                 265                 270

Leu Ser Phe Ala Leu Tyr Phe Leu Val Lys Asn Pro His Val Leu Gln
    275                 280                 285

Lys Val Ala Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
        580                 585                 590

Gly Ala Glu Asn Ile Ala Asp Arg Gly Glu Ala Asp Ala Ser Asp Asp
595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640
```

-continued

Thr Leu Ser Leu Gln Phe Val Asp Ser Ala Asp Met Pro Leu Ala
                    645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

```
<210> SEQ ID NO 7
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 7
```

| | | | | | | | | | | | | | | |
|---|---|---|---|---|---|---|---|---|---|---|---|---|---|---|
| Thr | Ile | Lys | Glu | Met | Pro | Gln | Pro | Lys | Thr | Phe | Gly | Glu | Leu | Lys | Asn |
| 1 | | | | 5 | | | | | 10 | | | | | 15 |

| Leu | Pro | Leu | Leu | Asn | Thr | Asp | Lys | Pro | Val | Gln | Ala | Leu | Met | Lys | Ile |
| | | | 20 | | | | | 25 | | | | | 30 | | |

| Ala | Asp | Glu | Leu | Gly | Glu | Ile | Phe | Lys | Phe | Glu | Ala | Pro | Gly | Cys | Val |
| | | 35 | | | | | 40 | | | | | 45 | | | |

Thr Arg Tyr Leu Ser Ser Gln Arg Leu Ile Lys Glu Ala Cys Asp Glu
              50                  55                  60

Ser Arg Phe Asp Lys Asn Leu Ser Gln Ala Leu Lys Phe Ala Arg Asp
65                  70                  75                  80

Phe Gly Asp Gly Leu Val Thr Ser Trp Thr His Glu Ile Asn Trp
                    85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala

```
                370             375             380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Thr Leu Thr Leu Lys Pro Glu Gly Phe Val Val Lys Ala
                435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
                515                 520                 525
Val Leu Ile Val Thr Ala Ser Tyr Asn Gly His Pro Pro Asp Asn Ala
                530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
                595                 600                 605
Phe Glu Gly Thr Tyr Glu Glu Trp Arg Glu His Met Trp Ser Asp Val
                610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
                755                 760                 765
Ala Lys Thr Val Cys Pro Pro His Lys Val Glu Leu Glu Ala Leu Leu
                770                 775                 780
Glu Lys Gln Ala Tyr Lys Glu Gln Val Leu Ala Lys Arg Leu Thr Met
785                 790                 795                 800
```

```
Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Tyr Lys Gly Ile Ala
                850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                1000                1005

Val Glu Ala Thr Leu Met Lys Ser Tyr Ala Asp Val His Gln Val
                1010                1015                1020

Ser Glu Ala Asp Ala Arg Leu Trp Leu Gln Gln Leu Glu Glu Lys
                1025                1030                1035

Gly Arg Tyr Ala Lys Asp Val Trp Ala Gly
                1040                1045

<210> SEQ ID NO 8
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 8

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Cys Val
                35                  40                  45

Thr Arg Tyr Leu Ser Ser Gln Arg Leu Ile Lys Glu Ala Cys Asp Glu
                50                  55                  60

Ser Arg Phe Asp Lys Asn Leu Ser Gln Ala Leu Lys Phe Thr Arg Asp
65                  70                  75                  80

Phe Gly Gly Asp Gly Leu Val Thr Ser Trp Thr His Glu Ile Asn Trp
                85                  90                  95

Lys Lys Ala His Asn Ile Leu Leu Pro Ser Phe Ser Gln Gln Ala Met
                100                 105                 110
```

```
Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Leu Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525
```

```
Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
```

```
                          945                 950                 955                 960
His Thr Ala Phe Ser Arg Met Pro Asn Gln Pro Lys Thr Tyr Val Gln
              965                 970                 975

His Val Met Glu Gln Asp Gly Lys Lys Leu Ile Glu Leu Leu Asp Gln
              980                 985                 990

Gly Ala His Phe Tyr Ile Cys Gly Asp Gly Ser Gln Met Ala Pro Ala
              995                1000                1005

Val Glu Ala Thr Leu Met Lys Ser Tyr Ala Asp Val His Gln Val
         1010                1015                1020

Ser Glu Ala Asp Ala Arg Leu Trp Leu Gln Gln Leu Glu Glu Lys
         1025                1030                1035

Gly Arg Tyr Ala Lys Asp Val Trp Ala Gly
         1040                1045

<210> SEQ ID NO 9
<211> LENGTH: 458
<212> TYPE: PRT
<213> ORGANISM: Artificial Sequence
<220> FEATURE:
<223> OTHER INFORMATION: Mutant P450 monooxygenase

<400> SEQUENCE: 9

Glu Thr Ser Pro Ile Pro Gln Pro Lys Thr Phe Gly Pro Leu Gly Asn
  1               5                  10                  15

Leu Pro Leu Ile Asp Lys Asp Lys Pro Thr Leu Ser Leu Ile Lys Leu
                 20                  25                  30

Ala Glu Glu Gln Gly Pro Ile Phe Gln Ile His Thr Pro Ala Gly Thr
             35                  40                  45

Thr Ile Val Val Ser Gly His Glu Leu Val Lys Glu Val Cys Asp Glu
         50                  55                  60

Ser Arg Phe Asp Lys Asn Leu Ser Gln Ala Leu Lys Phe Val Arg Asp
 65                  70                  75                  80

Phe Ala Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Thr Gln Leu Ile Gln
        115                 120                 125

Lys Trp Ser Arg Leu Asn Pro Asn Glu Glu Ile Asp Val Ala Asp Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Arg Met Ile Ala Glu Arg Lys
    210                 215                 220

Ala Asn Pro Asp Glu Ile Lys Asp Leu Leu Ser Leu Met Leu Tyr Ala
225                 230                 235                 240

Lys Asp Pro Val Thr Gly Glu Thr Leu Asp Asp Glu Asn Ile Arg Tyr
                245                 250                 255

Gln Ile Ile Thr Phe Leu Ile Ala Gly His Glu Thr Thr Ser Gly Leu
```

```
            260                 265                 270
Leu Ser Phe Ala Ile Tyr Cys Leu Leu Thr His Pro Glu Lys Leu Lys
        275                 280                 285

Lys Ala Gln Glu Glu Ala Asp Arg Val Leu Thr Asp Asp Thr Pro Glu
        290                 295                 300

Tyr Lys Gln Ile Gln Gln Leu Lys Tyr Ile Arg Met Val Leu Asn Glu
305                 310                 315                 320

Thr Leu Arg Leu Tyr Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu Gln Glu Ala Thr Met Val Leu Gly Leu
                405                 410                 415

Val Leu Lys His Phe Glu Leu Ile Asn His Thr Gly Tyr Glu Leu Lys
            420                 425                 430

Ile Lys Glu Ala Leu Thr Ile Lys Pro Asp Asp Phe Lys Ile Thr Val
        435                 440                 445

Lys Pro Arg Lys Thr Ala Ala Ile Asn Val
        450                 455

<210> SEQ ID NO 10
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 10

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
```

```
            165                 170                 175
Met Val Arg Ala Leu Asp Glu Val Met Asn Lys Leu Gln Arg Ala Asn
            180                 185                 190

Pro Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
        210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Arg Val Leu Val Asp Pro Val Pro Ser
        290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590
```

-continued

```
Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005
```

```
Val Glu  Ala Thr Leu Met Lys  Ser Tyr Ala Asp Val  His Gln Val
    1010             1015              1020

Ser Glu  Ala Asp Ala Arg Leu  Trp Leu Gln Gln Leu  Glu Glu Lys
    1025             1030              1035

Gly Arg  Tyr Ala Lys Asp Val  Trp Ala Gly
    1040             1045

<210> SEQ ID NO 11
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 11

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Trp Ser Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Asp Pro Val Pro Ser
    290                 295                 300

Tyr Lys Gln Val Lys Gln Leu Lys Tyr Val Gly Met Val Leu Asn Glu
305                 310                 315                 320
```

-continued

```
Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
        340                 345                 350

Val Met Val Leu Ile Pro Gln Leu His Arg Asp Lys Thr Ile Trp Gly
    355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
```

```
                    740                 745                 750
Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
        1010                1015                1020

Ser Glu Ala Asp Ala Arg Leu Trp Leu Gln Gln Leu Glu Glu Lys
        1025                1030                1035

Gly Arg Tyr Ala Lys Asp Val Trp Ala Gly
        1040                1045

<210> SEQ ID NO 12
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 12

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
```

-continued

```
                50                  55                  60
Ser Arg Phe Asp Lys Asn Leu Ser Gln Ala Leu Lys Phe Leu Arg Asp
65                  70                  75                  80

Phe Ala Gly Asp Gly Leu Val Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
                115                 120                 125

Lys Trp Glu Arg Leu Asn Ala Asp Glu His Ile Glu Val Ser Glu Asp
                130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Val Leu Asp Glu Thr Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Val Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
                450                 455                 460

Gln Ser Ala Lys Lys Val Arg Lys Lys Ala Glu Asn Ala His Asn Thr
465                 470                 475                 480
```

```
Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
        500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895
```

```
Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 13
<211> LENGTH: 1048
<212> TYPE: PRT
<213> ORGANISM: Artificial Sequence
<220> FEATURE:
<223> OTHER INFORMATION: Mutant P450 monooxygenase

<400> SEQUENCE: 13

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Leu Arg Asp
65                  70                  75                  80

Phe Ala Gly Asp Gly Leu Ala Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Thr Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205
```

```
Ile Lys Val Met Asn Asp Leu Val Asp Lys Ile Ile Ala Asp Arg Lys
210                 215                 220

Ala Arg Gly Glu Gln Ser Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Met Ala Gly His Glu Thr Thr Ser Gly Leu
                260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Val Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
```

```
                625                 630                 635                 640
         Thr Leu Ser Leu Gln Phe Val Asp Ser Ala Asp Met Pro Leu Ala
                         645                 650                 655
         Lys Met His Gly Ala Phe Ser Thr Asn Val Val Ala Ser Lys Glu Leu
                         660                 665                 670
         Gln Gln Pro Gly Ser Ala Arg Ser Thr Arg His Leu Glu Ile Glu Leu
                         675                 680                 685
         Pro Lys Glu Ala Ser Tyr Gln Glu Gly Asp His Leu Gly Val Ile Pro
                 690                 695                 700
         Arg Asn Tyr Glu Gly Ile Val Asn Arg Val Thr Ala Arg Phe Gly Leu
         705                 710                 715                 720
         Asp Ala Ser Gln Gln Ile Arg Leu Glu Ala Glu Glu Lys Leu Ala
                         725                 730                 735
         His Leu Pro Leu Ala Lys Thr Val Ser Val Glu Leu Leu Gln Tyr
                         740                 745                 750
         Val Glu Leu Gln Asp Pro Val Thr Arg Thr Gln Leu Arg Ala Met Ala
                 755                 760                 765
         Ala Lys Thr Val Cys Pro Pro His Lys Val Glu Leu Glu Ala Leu Leu
         770                 775                 780
         Glu Lys Gln Ala Tyr Lys Glu Gln Val Leu Ala Lys Arg Leu Thr Met
         785                 790                 795                 800
         Leu Glu Leu Leu Glu Lys Tyr Pro Ala Cys Glu Met Lys Phe Ser Glu
                         805                 810                 815
         Phe Ile Ala Leu Leu Pro Ser Ile Arg Pro Arg Tyr Tyr Ser Ile Ser
                         820                 825                 830
         Ser Ser Pro Arg Val Asp Glu Lys Gln Ala Ser Ile Thr Val Ser Val
                         835                 840                 845
         Val Ser Gly Glu Ala Trp Ser Gly Tyr Gly Glu Tyr Lys Gly Ile Ala
                         850                 855                 860
         Ser Asn Tyr Leu Ala Glu Leu Gln Glu Gly Asp Thr Ile Thr Cys Phe
         865                 870                 875                 880
         Ile Ser Thr Pro Gln Ser Glu Phe Thr Leu Pro Lys Asp Pro Glu Thr
                         885                 890                 895
         Pro Leu Ile Met Val Gly Pro Gly Thr Gly Val Ala Pro Phe Arg Gly
                         900                 905                 910
         Phe Val Gln Ala Arg Lys Gln Leu Lys Glu Gln Gly Gln Ser Leu Gly
                         915                 920                 925
         Glu Ala His Leu Tyr Phe Gly Cys Arg Ser Pro His Glu Asp Tyr Leu
                 930                 935                 940
         Tyr Gln Glu Glu Leu Glu Asn Ala Gln Ser Glu Gly Ile Ile Thr Leu
         945                 950                 955                 960
         His Thr Ala Phe Ser Arg Met Pro Asn Gln Pro Lys Thr Tyr Val Gln
                         965                 970                 975
         His Val Met Glu Gln Asp Gly Lys Lys Leu Ile Glu Leu Leu Asp Gln
                 980                 985                 990
         Gly Ala His Phe Tyr Ile Cys Gly Asp Gly Ser Gln Met Ala Pro Ala
                 995                 1000                1005
         Val Glu Ala Thr Leu Met Lys Ser Tyr Ala Asp Val His Gln Val
                 1010                1015                1020
         Ser Glu Ala Asp Ala Arg Leu Trp Leu Gln Gln Leu Glu Glu Lys
                 1025                1030                1035
         Gly Arg Tyr Ala Lys Asp Val Trp Ala Gly
                 1040                1045
```

<210> SEQ ID NO 14
<211> LENGTH: 3150
<212> TYPE: DNA
<213> ORGANISM: Bacillus megaterium
<220> FEATURE:
<221> NAME/KEY: CDS
<222> LOCATION: (4)..(3150)

<400> SEQUENCE: 14

| | | | | | | | | | | | | | | | | |
|---|---|---|---|---|---|---|---|---|---|---|---|---|---|---|---|---|
| atg | aca | att | aaa | gaa | atg | cct | cag | cca | aaa | acg | ttt | gga | gag | ctt | aaa | 48 |
| | Thr | Ile | Lys | Glu | Met | Pro | Gln | Pro | Lys | Thr | Phe | Gly | Glu | Leu | Lys | |
| | 1 | | | | 5 | | | | | 10 | | | | | 15 | |
| aat | tta | ccg | tta | tta | aac | aca | gat | aaa | ccg | gtt | caa | gct | ttg | atg | aaa | 96 |
| Asn | Leu | Pro | Leu | Leu | Asn | Thr | Asp | Lys | Pro | Val | Gln | Ala | Leu | Met | Lys | |
| | | | | 20 | | | | | 25 | | | | | 30 | | |
| att | gcg | gat | gaa | tta | gga | gaa | atc | ttt | aaa | ttc | gag | gcg | cct | ggt | cgt | 144 |
| Ile | Ala | Asp | Glu | Leu | Gly | Glu | Ile | Phe | Lys | Phe | Glu | Ala | Pro | Gly | Arg | |
| | | 35 | | | | | 40 | | | | | 45 | | | | |
| gta | acg | cgc | tac | tta | tca | agt | cag | cgt | cta | att | aaa | gaa | gca | tgc | gat | 192 |
| Val | Thr | Arg | Tyr | Leu | Ser | Ser | Gln | Arg | Leu | Ile | Lys | Glu | Ala | Cys | Asp | |
| 50 | | | | | 55 | | | | | 60 | | | | | | |
| gaa | tca | cgc | ttt | gat | aaa | aac | tta | agt | caa | gcg | ctt | aaa | ttt | gta | cgt | 240 |
| Glu | Ser | Arg | Phe | Asp | Lys | Asn | Leu | Ser | Gln | Ala | Leu | Lys | Phe | Val | Arg | |
| 65 | | | | | 70 | | | | | 75 | | | | | | |
| gat | ttt | gca | gga | gac | ggg | tta | ttt | aca | agc | tgg | acg | cat | gaa | aaa | aat | 288 |
| Asp | Phe | Ala | Gly | Asp | Gly | Leu | Phe | Thr | Ser | Trp | Thr | His | Glu | Lys | Asn | |
| 80 | | | | | 85 | | | | | 90 | | | | | 95 | |
| tgg | aaa | aaa | gcg | cat | aat | atc | tta | ctt | cca | agc | ttc | agt | cag | cag | gca | 336 |
| Trp | Lys | Lys | Ala | His | Asn | Ile | Leu | Leu | Pro | Ser | Phe | Ser | Gln | Gln | Ala | |
| | | | | 100 | | | | | 105 | | | | | 110 | | |
| atg | aaa | ggc | tat | cat | gcg | atg | atg | gtc | gat | atc | gcc | gtg | cag | ctt | gtt | 384 |
| Met | Lys | Gly | Tyr | His | Ala | Met | Met | Val | Asp | Ile | Ala | Val | Gln | Leu | Val | |
| | | | 115 | | | | | 120 | | | | | 125 | | | |
| caa | aag | tgg | gag | cgt | cta | aat | gca | gat | gag | cat | att | gaa | gta | ccg | gaa | 432 |
| Gln | Lys | Trp | Glu | Arg | Leu | Asn | Ala | Asp | Glu | His | Ile | Glu | Val | Pro | Glu | |
| | | 130 | | | | | 135 | | | | | 140 | | | | |
| gac | atg | aca | cgt | tta | acg | ctt | gat | aca | att | ggt | ctt | tgc | ggc | ttt | aac | 480 |
| Asp | Met | Thr | Arg | Leu | Thr | Leu | Asp | Thr | Ile | Gly | Leu | Cys | Gly | Phe | Asn | |
| 145 | | | | | 150 | | | | | 155 | | | | | | |
| tat | cgc | ttt | aac | agc | ttt | tac | cga | gat | cag | cct | cat | cca | ttt | att | aca | 528 |
| Tyr | Arg | Phe | Asn | Ser | Phe | Tyr | Arg | Asp | Gln | Pro | His | Pro | Phe | Ile | Thr | |
| 160 | | | | | 165 | | | | | 170 | | | | | 175 | |
| agt | atg | gtc | cgt | gca | ctg | gat | gaa | gca | atg | aac | aag | ctg | cag | cga | gca | 576 |
| Ser | Met | Val | Arg | Ala | Leu | Asp | Glu | Ala | Met | Asn | Lys | Leu | Gln | Arg | Ala | |
| | | | 180 | | | | | 185 | | | | | 190 | | | |
| aat | cca | gac | gac | cca | gct | tat | gat | gaa | aac | aag | cgc | cag | ttt | caa | gaa | 624 |
| Asn | Pro | Asp | Asp | Pro | Ala | Tyr | Asp | Glu | Asn | Lys | Arg | Gln | Phe | Gln | Glu | |
| | | | | 195 | | | | | 200 | | | | | 205 | | |
| gat | atc | aag | gtg | atg | aac | gac | cta | gta | gat | aaa | att | att | gca | gat | cgc | 672 |
| Asp | Ile | Lys | Val | Met | Asn | Asp | Leu | Val | Asp | Lys | Ile | Ile | Ala | Asp | Arg | |
| | | 210 | | | | | 215 | | | | | 220 | | | | |
| aaa | gca | agc | ggt | gaa | caa | agc | gat | gat | tta | tta | acg | cat | atg | cta | aac | 720 |
| Lys | Ala | Ser | Gly | Glu | Gln | Ser | Asp | Asp | Leu | Leu | Thr | His | Met | Leu | Asn | |
| 225 | | | | | 230 | | | | | 235 | | | | | | |
| gga | aaa | gat | cca | gaa | acg | ggt | gag | ccg | ctt | gat | gac | gag | aac | att | cgc | 768 |
| Gly | Lys | Asp | Pro | Glu | Thr | Gly | Glu | Pro | Leu | Asp | Asp | Glu | Asn | Ile | Arg | |
| 240 | | | | | 245 | | | | | 250 | | | | | 255 | |
| tat | caa | att | att | aca | ttc | tta | att | gcg | gga | cac | gaa | aca | aca | agt | ggt | 816 |
| Tyr | Gln | Ile | Ile | Thr | Phe | Leu | Ile | Ala | Gly | His | Glu | Thr | Thr | Ser | Gly | |
| | | | | 260 | | | | | 265 | | | | | 270 | | |

```
ctt tta tca ttt gcg ctg tat ttc tta gtg aaa aat cca cat gta tta      864
Leu Leu Ser Phe Ala Leu Tyr Phe Leu Val Lys Asn Pro His Val Leu
        275                 280                 285 caa aaa gca gca gaa gaa gca gca cga gtt cta gta gat cct gtt cca      912
Gln Lys Ala Ala Glu Glu Ala Ala Arg Val Leu Val Asp Pro Val Pro
        290                 295                 300 agc tac aaa caa gtc aaa cag ctt aaa tat gtc ggc atg gtc tta aac      960
Ser Tyr Lys Gln Val Lys Gln Leu Lys Tyr Val Gly Met Val Leu Asn
        305                 310                 315 gaa gcg ctg cgc tta tgg cca act gct cct gcg ttt tcc cta tat gca     1008
Glu Ala Leu Arg Leu Trp Pro Thr Ala Pro Ala Phe Ser Leu Tyr Ala
320                 325                 330                 335 aaa gaa gat acg gtg ctt gga gga gaa tat cct tta gaa aaa ggc gac     1056
Lys Glu Asp Thr Val Leu Gly Gly Glu Tyr Pro Leu Glu Lys Gly Asp
                340                 345                 350 gaa cta atg gtt ctg att cct cag ctt cac cgt gat aaa aca att tgg     1104
Glu Leu Met Val Leu Ile Pro Gln Leu His Arg Asp Lys Thr Ile Trp
            355                 360                 365 gga gac gat gtg gaa gag ttc cgt cca gag cgt ttt gaa aat cca agt     1152
Gly Asp Asp Val Glu Glu Phe Arg Pro Glu Arg Phe Glu Asn Pro Ser
        370                 375                 380 gcg att ccg cag cat gcg ttt aaa ccg ttt gga aac ggt cag cgt gcg     1200
Ala Ile Pro Gln His Ala Phe Lys Pro Phe Gly Asn Gly Gln Arg Ala
385                 390                 395 tgt atc ggt cag cag ttc gct ctt cat gaa gca acg ctg gta ctt ggt     1248
Cys Ile Gly Gln Gln Phe Ala Leu His Glu Ala Thr Leu Val Leu Gly
400                 405                 410                 415 atg atg cta aaa cac ttt gac ttt gaa gat cat aca aac tac gag ctg     1296
Met Met Leu Lys His Phe Asp Phe Glu Asp His Thr Asn Tyr Glu Leu
                420                 425                 430 gat att aaa gaa act tta acg tta aaa cct gaa ggc ttt gtg gta aaa     1344
Asp Ile Lys Glu Thr Leu Thr Leu Lys Pro Glu Gly Phe Val Val Lys
            435                 440                 445 gca aaa tcg aaa aaa att ccg ctt ggc ggt att cct tca cct agc act     1392
Ala Lys Ser Lys Lys Ile Pro Leu Gly Gly Ile Pro Ser Pro Ser Thr
        450                 455                 460 gaa cag tct gct aaa aaa gta cgc aaa aag gca gaa aac gct cat aat     1440
Glu Gln Ser Ala Lys Lys Val Arg Lys Lys Ala Glu Asn Ala His Asn
465                 470                 475 acg ccg ctg ctt gtg cta tac ggt tca aat atg gga aca gct gaa gga     1488
Thr Pro Leu Leu Val Leu Tyr Gly Ser Asn Met Gly Thr Ala Glu Gly
480                 485                 490                 495 acg gcg cgt gat tta gca gat att gca atg agc aaa gga ttt gca ccg     1536
Thr Ala Arg Asp Leu Ala Asp Ile Ala Met Ser Lys Gly Phe Ala Pro
                500                 505                 510 cag gtc gca acg ctt gat tca cac gcc gga aat ctt ccg cgc gaa gga     1584
Gln Val Ala Thr Leu Asp Ser His Ala Gly Asn Leu Pro Arg Glu Gly
            515                 520                 525 gct gta tta att gta acg gcg tct tat aac ggt cat ccg cct gat aac     1632
Ala Val Leu Ile Val Thr Ala Ser Tyr Asn Gly His Pro Pro Asp Asn
        530                 535                 540 gca aag caa ttt gtc gac tgg tta gac caa gcg tct gct gat gaa gta     1680
Ala Lys Gln Phe Val Asp Trp Leu Asp Gln Ala Ser Ala Asp Glu Val
545                 550                 555 aaa ggc gtt cgc tac tcc gta ttt gga tgc ggc gat aaa aac tgg gct     1728
Lys Gly Val Arg Tyr Ser Val Phe Gly Cys Gly Asp Lys Asn Trp Ala
560                 565                 570                 575 act acg tat caa aaa gtg cct gct ttt atc gat gaa acg ctt gcc gct     1776
Thr Thr Tyr Gln Lys Val Pro Ala Phe Ile Asp Glu Thr Leu Ala Ala
```

-continued

|  |  |  |  |  |  |  | 580 |  |  |  |  | 585 |  |  |  |  | 590 |  |  |  |
|---|---|---|---|---|---|---|---|---|---|---|---|---|---|---|---|---|---|---|---|---|
| aaa | ggg | gca | gaa | aac | atc | gct | gac | cgc | ggt | gaa | gca | gat | gca | agc | gac |  |  |  |  | 1824 |
| Lys | Gly | Ala | Glu | Asn | Ile | Ala | Asp | Arg | Gly | Glu | Ala | Asp | Ala | Ser | Asp |  |  |  |  |  |
|  |  |  | 595 |  |  |  |  | 600 |  |  |  |  | 605 |  |  |  |  |  |  |  |
| gac | ttt | gaa | ggc | aca | tat | gaa | gaa | tgg | cgt | gaa | cat | atg | tgg | agt | gac |  |  |  |  | 1872 |
| Asp | Phe | Glu | Gly | Thr | Tyr | Glu | Glu | Trp | Arg | Glu | His | Met | Trp | Ser | Asp |  |  |  |  |  |
|  |  | 610 |  |  |  |  | 615 |  |  |  |  | 620 |  |  |  |  |  |  |  |  |
| gta | gca | gcc | tac | ttt | aac | ctc | gac | att | gaa | aac | agt | gaa | gat | aat | aaa |  |  |  |  | 1920 |
| Val | Ala | Ala | Tyr | Phe | Asn | Leu | Asp | Ile | Glu | Asn | Ser | Glu | Asp | Asn | Lys |  |  |  |  |  |
|  | 625 |  |  |  |  | 630 |  |  |  |  | 635 |  |  |  |  |  |  |  |  |  |
| tct | act | ctt | tca | ctt | caa | ttt | gtc | gac | agc | gcc | gcg | gat | atg | ccg | ctt |  |  |  |  | 1968 |
| Ser | Thr | Leu | Ser | Leu | Gln | Phe | Val | Asp | Ser | Ala | Ala | Asp | Met | Pro | Leu |  |  |  |  |  |
| 640 |  |  |  |  | 645 |  |  |  |  | 650 |  |  |  |  | 655 |  |  |  |  |
| gcg | aaa | atg | cac | ggt | gcg | ttt | tca | acg | aac | gtc | gta | gca | agc | aaa | gaa |  |  |  |  | 2016 |
| Ala | Lys | Met | His | Gly | Ala | Phe | Ser | Thr | Asn | Val | Val | Ala | Ser | Lys | Glu |  |  |  |  |  |
|  |  |  |  | 660 |  |  |  |  | 665 |  |  |  |  | 670 |  |  |  |  |  |
| ctt | caa | cag | cca | ggc | agt | gca | cga | agc | acg | cga | cat | ctt | gaa | att | gaa |  |  |  |  | 2064 |
| Leu | Gln | Gln | Pro | Gly | Ser | Ala | Arg | Ser | Thr | Arg | His | Leu | Glu | Ile | Glu |  |  |  |  |  |
|  |  |  | 675 |  |  |  |  | 680 |  |  |  |  | 685 |  |  |  |  |  |  |
| ctt | cca | aaa | gaa | gct | tct | tat | caa | gaa | gga | gat | cat | tta | ggt | gtt | att |  |  |  |  | 2112 |
| Leu | Pro | Lys | Glu | Ala | Ser | Tyr | Gln | Glu | Gly | Asp | His | Leu | Gly | Val | Ile |  |  |  |  |  |
|  |  | 690 |  |  |  |  | 695 |  |  |  |  | 700 |  |  |  |  |  |  |  |
| cct | cgc | aac | tat | gaa | gga | ata | gta | aac | cgt | gta | aca | gca | agg | ttc | ggc |  |  |  |  | 2160 |
| Pro | Arg | Asn | Tyr | Glu | Gly | Ile | Val | Asn | Arg | Val | Thr | Ala | Arg | Phe | Gly |  |  |  |  |  |
|  | 705 |  |  |  |  | 710 |  |  |  |  | 715 |  |  |  |  |  |  |  |  |
| cta | gat | gca | tca | cag | caa | atc | cgt | ctg | gaa | gca | gaa | gaa | gaa | aaa | tta |  |  |  |  | 2208 |
| Leu | Asp | Ala | Ser | Gln | Gln | Ile | Arg | Leu | Glu | Ala | Glu | Glu | Glu | Lys | Leu |  |  |  |  |  |
| 720 |  |  |  |  | 725 |  |  |  |  | 730 |  |  |  |  | 735 |  |  |  |  |
| gct | cat | ttg | cca | ctc | gct | aaa | aca | gta | tcc | gta | gaa | gag | ctt | ctg | caa |  |  |  |  | 2256 |
| Ala | His | Leu | Pro | Leu | Ala | Lys | Thr | Val | Ser | Val | Glu | Glu | Leu | Leu | Gln |  |  |  |  |  |
|  |  |  |  | 740 |  |  |  |  | 745 |  |  |  |  | 750 |  |  |  |  |  |
| tac | gtg | gag | ctt | caa | gat | cct | gtt | acg | cgc | acg | cag | ctt | cgc | gca | atg |  |  |  |  | 2304 |
| Tyr | Val | Glu | Leu | Gln | Asp | Pro | Val | Thr | Arg | Thr | Gln | Leu | Arg | Ala | Met |  |  |  |  |  |
|  |  |  | 755 |  |  |  |  | 760 |  |  |  |  | 765 |  |  |  |  |  |  |
| gct | gct | aaa | acg | gtc | tgc | ccg | ccg | cat | aaa | gta | gag | ctt | gaa | gcc | ttg |  |  |  |  | 2352 |
| Ala | Ala | Lys | Thr | Val | Cys | Pro | Pro | His | Lys | Val | Glu | Leu | Glu | Ala | Leu |  |  |  |  |  |
|  |  | 770 |  |  |  |  | 775 |  |  |  |  | 780 |  |  |  |  |  |  |  |
| ctt | gaa | aag | caa | gcc | tac | aaa | gaa | caa | gtg | ctg | gca | aaa | cgt | tta | aca |  |  |  |  | 2400 |
| Leu | Glu | Lys | Gln | Ala | Tyr | Lys | Glu | Gln | Val | Leu | Ala | Lys | Arg | Leu | Thr |  |  |  |  |  |
|  | 785 |  |  |  |  | 790 |  |  |  |  | 795 |  |  |  |  |  |  |  |  |
| atg | ctt | gaa | ctg | ctt | gaa | aaa | tac | ccg | gcg | tgt | gaa | atg | aaa | ttc | agc |  |  |  |  | 2448 |
| Met | Leu | Glu | Leu | Leu | Glu | Lys | Tyr | Pro | Ala | Cys | Glu | Met | Lys | Phe | Ser |  |  |  |  |  |
| 800 |  |  |  |  | 805 |  |  |  |  | 810 |  |  |  |  | 815 |  |  |  |  |
| gaa | ttt | atc | gcc | ctt | ctg | cca | agc | ata | cgc | ccg | cgc | tat | tac | tcg | att |  |  |  |  | 2496 |
| Glu | Phe | Ile | Ala | Leu | Leu | Pro | Ser | Ile | Arg | Pro | Arg | Tyr | Tyr | Ser | Ile |  |  |  |  |  |
|  |  |  |  | 820 |  |  |  |  | 825 |  |  |  |  | 830 |  |  |  |  |  |
| tct | tca | tca | cct | cgt | gtc | gat | gaa | aaa | caa | gca | agc | atc | acg | gtc | agc |  |  |  |  | 2544 |
| Ser | Ser | Ser | Pro | Arg | Val | Asp | Glu | Lys | Gln | Ala | Ser | Ile | Thr | Val | Ser |  |  |  |  |  |
|  |  |  | 835 |  |  |  |  | 840 |  |  |  |  | 845 |  |  |  |  |  |  |
| gtt | gtc | tca | gga | gaa | gcg | tgg | agc | gga | tat | gga | gaa | tat | aaa | gga | att |  |  |  |  | 2592 |
| Val | Val | Ser | Gly | Glu | Ala | Trp | Ser | Gly | Tyr | Gly | Glu | Tyr | Lys | Gly | Ile |  |  |  |  |  |
|  |  | 850 |  |  |  |  | 855 |  |  |  |  | 860 |  |  |  |  |  |  |  |
| gcg | tcg | aac | tat | ctt | gcc | gag | ctg | caa | gaa | gga | gat | acg | att | acg | tgc |  |  |  |  | 2640 |
| Ala | Ser | Asn | Tyr | Leu | Ala | Glu | Leu | Gln | Glu | Gly | Asp | Thr | Ile | Thr | Cys |  |  |  |  |  |
|  | 865 |  |  |  |  | 870 |  |  |  |  | 875 |  |  |  |  |  |  |  |  |
| ttt | att | tcc | aca | ccg | cag | tca | gaa | ttt | acg | ctg | cca | aaa | gac | cct | gaa |  |  |  |  | 2688 |
| Phe | Ile | Ser | Thr | Pro | Gln | Ser | Glu | Phe | Thr | Leu | Pro | Lys | Asp | Pro | Glu |  |  |  |  |  |
| 880 |  |  |  |  | 885 |  |  |  |  | 890 |  |  |  |  | 895 |  |  |  |  |
| acg | ccg | ctt | atc | atg | gtc | gga | ccg | gga | aca | ggc | gtc | gcg | ccg | ttt | aga |  |  |  |  | 2736 |

```
Thr Pro Leu Ile Met Val Gly Pro Gly Thr Gly Val Ala Pro Phe Arg
                900                 905                 910 ggc ttt gtg cag gcg cgc aaa cag cta aaa gaa caa gga cag tca ctt     2784
Gly Phe Val Gln Ala Arg Lys Gln Leu Lys Glu Gln Gly Gln Ser Leu
            915                 920                 925 gga gaa gca cat tta tac ttc ggc tgc cgt tca cct cat gaa gac tat     2832
Gly Glu Ala His Leu Tyr Phe Gly Cys Arg Ser Pro His Glu Asp Tyr
        930                 935                 940 ctg tat caa gaa gag ctt gaa aac gcc caa agc gaa ggc atc att acg     2880
Leu Tyr Gln Glu Glu Leu Glu Asn Ala Gln Ser Glu Gly Ile Ile Thr
    945                 950                 955 ctt cat acc gct ttt tct cgc atg cca aat cag ccg aaa aca tac gtt     2928
Leu His Thr Ala Phe Ser Arg Met Pro Asn Gln Pro Lys Thr Tyr Val
960                 965                 970                 975 cag cac gta atg gaa caa gac ggc aag aaa ttg att gaa ctt ctt gat     2976
Gln His Val Met Glu Gln Asp Gly Lys Lys Leu Ile Glu Leu Leu Asp
                980                 985                 990 caa gga gcg cac ttc tat att tgc gga gac gga agc caa atg gca cct    3024
Gln Gly Ala His Phe Tyr Ile Cys Gly Asp Gly Ser Gln Met Ala Pro
            995                 1000                1005 gcc gtt gaa gca acg ctt atg aaa agc tat gct gac gtt cac caa       3069
Ala Val Glu Ala Thr Leu Met Lys Ser Tyr Ala Asp Val His Gln
        1010                1015                1020 gtg agt gaa gca gac gct cgc tta tgg ctg cag cag cta gaa gaa       3114
Val Ser Glu Ala Asp Ala Arg Leu Trp Leu Gln Gln Leu Glu Glu
    1025                1030                1035 aaa ggc cga tac gca aaa gac gtg tgg gct ggg taa                   3150
Lys Gly Arg Tyr Ala Lys Asp Val Trp Ala Gly
1040                1045

<210> SEQ ID NO 15
<211> LENGTH: 1048
<212> TYPE: PRT
<213> ORGANISM: Bacillus megaterium

<400> SEQUENCE: 15

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175
```

```
Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590
```

```
Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val
```

```
                 1010                1015                1020
Ser Glu Ala Asp Ala Arg Leu Trp Leu Gln Gln Leu Glu Glu Lys
         1025                1030                1035

Gly Arg Tyr Ala Lys Asp Val Trp Ala Gly
         1040                1045

<210> SEQ ID NO 16
<211> LENGTH: 3186
<212> TYPE: DNA
<213> ORGANISM: Bacillus subtilis
<220> FEATURE:
<221> NAME/KEY: CDS
<222> LOCATION: (4)..(3186)

<400> SEQUENCE: 16 atg aag gaa aca agc ccg att cct cag ccg aag acg ttt ggg ccg ctc        48
    Lys Glu Thr Ser Pro Ile Pro Gln Pro Lys Thr Phe Gly Pro Leu
    1               5                   10                  15 ggc aat ttg cct tta att gat aaa gac aaa ccg acg ctt tcg ctg atc       96
Gly Asn Leu Pro Leu Ile Asp Lys Asp Lys Pro Thr Leu Ser Leu Ile
            20                  25                  30 aaa ctg gcg gaa gaa cag ggc ccg att ttt caa atc cat aca ccc gcg      144
Lys Leu Ala Glu Glu Gln Gly Pro Ile Phe Gln Ile His Thr Pro Ala
        35                  40                  45 ggc acg acc att gta gtg tcc ggc cat gaa ttg gtg aaa gag gtt tgt      192
Gly Thr Thr Ile Val Val Ser Gly His Glu Leu Val Lys Glu Val Cys
    50                  55                  60 gat gaa gaa cgg ttt gat aaa agc att gaa ggc gcc ttg gaa aag gtt      240
Asp Glu Glu Arg Phe Asp Lys Ser Ile Glu Gly Ala Leu Glu Lys Val
65                  70                  75 cgc gca ttt tcc ggt gac gga ttg ttt acg agc tgg acg cat gag cct      288
Arg Ala Phe Ser Gly Asp Gly Leu Phe Thr Ser Trp Thr His Glu Pro
80                  85                  90                  95 aac tgg aga aaa gcg cac aac att ctg atg ccg acg ttc agc cag cgg      336
Asn Trp Arg Lys Ala His Asn Ile Leu Met Pro Thr Phe Ser Gln Arg
            100                 105                 110 gcc atg aag gac tat cat gag aaa atg gtc gat atc gct gtt cag ctc      384
Ala Met Lys Asp Tyr His Glu Lys Met Val Asp Ile Ala Val Gln Leu
        115                 120                 125 att caa aaa tgg gca agg ctc aac ccg aat gaa gca gtc gat gtc ccg      432
Ile Gln Lys Trp Ala Arg Leu Asn Pro Asn Glu Ala Val Asp Val Pro
    130                 135                 140 gga gat atg acc cgg ctg acg ctc gac acc att ggg cta tgc ggg ttt      480
Gly Asp Met Thr Arg Leu Thr Leu Asp Thr Ile Gly Leu Cys Gly Phe
145                 150                 155 aac tac cgc ttt aac agt tac tac aga gaa acg ccc cac ccg ttt atc      528
Asn Tyr Arg Phe Asn Ser Tyr Tyr Arg Glu Thr Pro His Pro Phe Ile
160                 165                 170                 175 aac agc atg gtg cgg gcg ctt gat gaa gcg atg cat caa atg cag cgg      576
Asn Ser Met Val Arg Ala Leu Asp Glu Ala Met His Gln Met Gln Arg
            180                 185                 190 ctt gat gtt caa gat aag ctt atg gtc aga aca aag cgg caa ttc cgc      624
Leu Asp Val Gln Asp Lys Leu Met Val Arg Thr Lys Arg Gln Phe Arg
        195                 200                 205 tat gat att caa acg atg ttt tcg tta gtc gac agc att att gca gag      672
Tyr Asp Ile Gln Thr Met Phe Ser Leu Val Asp Ser Ile Ile Ala Glu
    210                 215                 220 cgc agg gcg aat gga gac cag gat gaa aaa gat ttg ctc gcc cgc atg      720
Arg Arg Ala Asn Gly Asp Gln Asp Glu Lys Asp Leu Leu Ala Arg Met
225                 230                 235
```

```
ctg aat gtg gaa gat ccg gaa act ggt gaa aag ctc gac gac gaa aat    768
Leu Asn Val Glu Asp Pro Glu Thr Gly Glu Lys Leu Asp Asp Glu Asn
240             245                 250                 255 atc cgc ttt cag atc atc acg ttt ttg att gcc ggc cat gaa aca acg    816
Ile Arg Phe Gln Ile Ile Thr Phe Leu Ile Ala Gly His Glu Thr Thr
                260                 265                 270 agc ggc ctg ctt tcc ttt gcg act tac ttt tta ttg aag cat cct gac    864
Ser Gly Leu Leu Ser Phe Ala Thr Tyr Phe Leu Leu Lys His Pro Asp
            275                 280                 285 aaa ctg aaa aag gcg tat gaa gag gtc gat cgg gtg ctg acg gat gca    912
Lys Leu Lys Lys Ala Tyr Glu Glu Val Asp Arg Val Leu Thr Asp Ala
        290                 295                 300 gcg ccg acc tat aaa caa gtg ctg gag ctt aca tac ata cgg atg att    960
Ala Pro Thr Tyr Lys Gln Val Leu Glu Leu Thr Tyr Ile Arg Met Ile
    305                 310                 315 tta aat gaa tca ctg cgc tta tgg ccg aca gct ccg gct ttc agc ctt   1008
Leu Asn Glu Ser Leu Arg Leu Trp Pro Thr Ala Pro Ala Phe Ser Leu
320                 325                 330                 335 tat cca aaa gaa gac aca gtc att ggc gga aaa ttt ccg atc acg acg   1056
Tyr Pro Lys Glu Asp Thr Val Ile Gly Gly Lys Phe Pro Ile Thr Thr
                340                 345                 350 aat gac aga att tct gtg ctg att ccg cag ctt cat cgt gat cga gac   1104
Asn Asp Arg Ile Ser Val Leu Ile Pro Gln Leu His Arg Asp Arg Asp
            355                 360                 365 gct tgg gga aag gac gca gaa gaa ttc cgg ccg gaa cgg ttt gag cat   1152
Ala Trp Gly Lys Asp Ala Glu Glu Phe Arg Pro Glu Arg Phe Glu His
        370                 375                 380 cag gac caa gtg cct cat cat gcg tac aaa cca ttc gga aat gga caa   1200
Gln Asp Gln Val Pro His His Ala Tyr Lys Pro Phe Gly Asn Gly Gln
385                 390                 395 cgg gcc tgt atc ggc atg cag ttt gcc ctt cat gaa gcc aca ctt gtg   1248
Arg Ala Cys Ile Gly Met Gln Phe Ala Leu His Glu Ala Thr Leu Val
400                 405                 410                 415 tta ggc atg att cta aaa tat ttc aca ttg att gat cat gag aat tat   1296
Leu Gly Met Ile Leu Lys Tyr Phe Thr Leu Ile Asp His Glu Asn Tyr
                420                 425                 430 gag ctt gat atc aaa caa acc tta aca ctt aag ccg ggc gat ttt cac   1344
Glu Leu Asp Ile Lys Gln Thr Leu Thr Leu Lys Pro Gly Asp Phe His
            435                 440                 445 atc agt gtt caa agc cgt cat cag gaa gcc att cat gca gac gtc cag   1392
Ile Ser Val Gln Ser Arg His Gln Glu Ala Ile His Ala Asp Val Gln
        450                 455                 460 gca gct gaa aaa gcc gcg cct gat gag caa aag gag aaa acg gaa gca   1440
Ala Ala Glu Lys Ala Ala Pro Asp Glu Gln Lys Glu Lys Thr Glu Ala
465                 470                 475 aag ggt gca tcg gtc atc ggt ctt aac aac cgc ccg ctt ctc gtg ctg   1488
Lys Gly Ala Ser Val Ile Gly Leu Asn Asn Arg Pro Leu Leu Val Leu
480                 485                 490                 495 tac ggc tca gat acc ggc acc gca gaa ggc gtc gcc cgg gag ctt gct   1536
Tyr Gly Ser Asp Thr Gly Thr Ala Glu Gly Val Ala Arg Glu Leu Ala
                500                 505                 510 gat act gcc agt ctt cac ggc gta agg aca aag aca gca cct ctg aac   1584
Asp Thr Ala Ser Leu His Gly Val Arg Thr Lys Thr Ala Pro Leu Asn
            515                 520                 525 gac cgg att gga aag ctg ccg aaa gag gga gcg gtt gtc att gtg acc   1632
Asp Arg Ile Gly Lys Leu Pro Lys Glu Gly Ala Val Val Ile Val Thr
        530                 535                 540 tcg tct tat aat gga aag ccg cca agc aat gcc gga caa ttc gtg cag   1680
Ser Ser Tyr Asn Gly Lys Pro Pro Ser Asn Ala Gly Gln Phe Val Gln
545                 550                 555
```

```
tgg ctt caa gaa atc aaa ccg ggt gag ctt gag ggc gtc cat tac gcg      1728
Trp Leu Gln Glu Ile Lys Pro Gly Glu Leu Glu Gly Val His Tyr Ala
560             565                 570                 575 gta ttt ggc tgc ggc gac cac aac tgg gcg agc acg tat caa tac gtg      1776
Val Phe Gly Cys Gly Asp His Asn Trp Ala Ser Thr Tyr Gln Tyr Val
                580                 585                 590 ccg aga ttc att gat gag cag ctt gcg gag aaa ggc gcg act cgg ttt      1824
Pro Arg Phe Ile Asp Glu Gln Leu Ala Glu Lys Gly Ala Thr Arg Phe
            595                 600                 605 tct gcg cgc ggg gaa ggg gat gtg agc ggt gat ttt gaa ggg cag ctt      1872
Ser Ala Arg Gly Glu Gly Asp Val Ser Gly Asp Phe Glu Gly Gln Leu
        610                 615                 620 gac gag tgg aaa aaa agc atg tgg gcg gat gcc atc aaa gca ttc gga      1920
Asp Glu Trp Lys Lys Ser Met Trp Ala Asp Ala Ile Lys Ala Phe Gly
625                 630                 635 ctt gag ctt aat gaa aac gct gat aag gaa cga agc acg ctg agc ctt      1968
Leu Glu Leu Asn Glu Asn Ala Asp Lys Glu Arg Ser Thr Leu Ser Leu
640                 645                 650                 655 cag ttt gtc aga ggg ctg ggc gag tct ccg ctc gct aga tcg tac gaa      2016
Gln Phe Val Arg Gly Leu Gly Glu Ser Pro Leu Ala Arg Ser Tyr Glu
                660                 665                 670 gcc tct cac gca tcc att gcc gaa aat cgt gaa ctc cag tcc gca gac      2064
Ala Ser His Ala Ser Ile Ala Glu Asn Arg Glu Leu Gln Ser Ala Asp
            675                 680                 685 agc gat cga agc act cgc cat atc gaa att gca ttg ccg ccg gat gtt      2112
Ser Asp Arg Ser Thr Arg His Ile Glu Ile Ala Leu Pro Pro Asp Val
        690                 695                 700 gaa tat caa gag ggc gac cat ctt ggc gta ttg cca aaa aac agc caa      2160
Glu Tyr Gln Glu Gly Asp His Leu Gly Val Leu Pro Lys Asn Ser Gln
705                 710                 715 acc aat gtc agc cgg att ctt cac aga ttc ggt ctg aag gga acc gac      2208
Thr Asn Val Ser Arg Ile Leu His Arg Phe Gly Leu Lys Gly Thr Asp
720                 725                 730                 735 caa gtg aca ttg tcg gca agc ggc cgc agt gcg ggg cat ctg cca ttg      2256
Gln Val Thr Leu Ser Ala Ser Gly Arg Ser Ala Gly His Leu Pro Leu
                740                 745                 750 ggc cgt cct gtc agc ctg cat gat ctt ctc agc tac agc gtc gag gtg      2304
Gly Arg Pro Val Ser Leu His Asp Leu Leu Ser Tyr Ser Val Glu Val
            755                 760                 765 cag gaa gca gcc aca aga gcg caa ata cgt gaa ctg gcg tca ttt aca      2352
Gln Glu Ala Ala Thr Arg Ala Gln Ile Arg Glu Leu Ala Ser Phe Thr
        770                 775                 780 gtg tgt ccg ccg cat agg cgc gaa tta gaa gaa ctg tca gca gag ggt      2400
Val Cys Pro Pro His Arg Arg Glu Leu Glu Glu Leu Ser Ala Glu Gly
785                 790                 795 gtt tat cag gag caa ata ttg aaa aaa cga att tcc atg ctg gat ctg      2448
Val Tyr Gln Glu Gln Ile Leu Lys Lys Arg Ile Ser Met Leu Asp Leu
800                 805                 810                 815 ctt gaa aag tat gaa gcg tgt gac atg ccg ttt gaa cga ttt tta gag      2496
Leu Glu Lys Tyr Glu Ala Cys Asp Met Pro Phe Glu Arg Phe Leu Glu
                820                 825                 830 ctt tta cgg ccg tta aaa ccg aga tac tat tcg att tca agc tct cca      2544
Leu Leu Arg Pro Leu Lys Pro Arg Tyr Tyr Ser Ile Ser Ser Ser Pro
            835                 840                 845 aga gtg aat ccg cgg caa gca tcg atc aca gtc ggt gtc gtg cgc ggc      2592
Arg Val Asn Pro Arg Gln Ala Ser Ile Thr Val Gly Val Val Arg Gly
        850                 855                 860 ccg gcg tgg agc ggc cgt ggc gaa tac agg ggt gtg gca tca aat gat      2640
Pro Ala Trp Ser Gly Arg Gly Glu Tyr Arg Gly Val Ala Ser Asn Asp
```

```
                865                 870                 875
tta gct gag cgt caa gcc ggt gat gat gtc gtg atg ttt atc cgc aca    2688
Leu Ala Glu Arg Gln Ala Gly Asp Asp Val Val Met Phe Ile Arg Thr
880                 885                 890                 895 ccg gaa tcc cgg ttt cag ctt ccg aaa gac cct gaa acg cca att att    2736
Pro Glu Ser Arg Phe Gln Leu Pro Lys Asp Pro Glu Thr Pro Ile Ile
                900                 905                 910 atg gtc ggg cca ggc acg gga gtc gcg cca ttt cgc ggt ttc ctt caa    2784
Met Val Gly Pro Gly Thr Gly Val Ala Pro Phe Arg Gly Phe Leu Gln
            915                 920                 925 gcc cgc gat gtt tta aag cgg gag ggc aaa acg ctc ggt gag gct cat    2832
Ala Arg Asp Val Leu Lys Arg Glu Gly Lys Thr Leu Gly Glu Ala His
        930                 935                 940 ctc tat ttt gga tgc agg aac gat cgg gat ttt att tac cga gat gag    2880
Leu Tyr Phe Gly Cys Arg Asn Asp Arg Asp Phe Ile Tyr Arg Asp Glu
    945                 950                 955 ctt gag cgg ttt gaa aaa gac gga atc gtc act gtc cac aca gcc ttt    2928
Leu Glu Arg Phe Glu Lys Asp Gly Ile Val Thr Val His Thr Ala Phe
960                 965                 970                 975 tcc cga aaa gag ggc atg ccg aaa aca tat gtc cag cat ctc atg gct    2976
Ser Arg Lys Glu Gly Met Pro Lys Thr Tyr Val Gln His Leu Met Ala
                980                 985                 990 gac caa gca gat aca tta ata tca atc ctt gac cgc ggt ggc agg ctt    3024
Asp Gln Ala Asp Thr Leu Ile Ser Ile Leu Asp Arg Gly Gly Arg Leu
            995                 1000                1005 tat gta tgc ggt gat ggc agc aaa atg gcc ccg gat gtg gag gcg        3069
Tyr Val Cys Gly Asp Gly Ser Lys Met Ala Pro Asp Val Glu Ala
        1010                1015                1020 gca ctt caa aaa gcg tat cag gct gtc cat gga acc ggg gaa caa        3114
Ala Leu Gln Lys Ala Tyr Gln Ala Val His Gly Thr Gly Glu Gln
    1025                1030                1035 gaa gcg caa aac tgg ctg aga cat ctg cag gat acc ggt atg tac        3159
Glu Ala Gln Asn Trp Leu Arg His Leu Gln Asp Thr Gly Met Tyr
1040                1045                1050 gct aag gat gtc tgg gca ggg ata tag                                3186
Ala Lys Asp Val Trp Ala Gly Ile
            1055                1060

<210> SEQ ID NO 17
<211> LENGTH: 1060
<212> TYPE: PRT
<213> ORGANISM: Bacillus subtilis

<400> SEQUENCE: 17

Lys Glu Thr Ser Pro Ile Pro Gln Pro Lys Thr Phe Gly Pro Leu Gly
1               5                   10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
        35                  40                  45

Thr Thr Ile Val Val Ser Gly His Glu Leu Val Lys Glu Val Cys Asp
    50                  55                  60

Glu Glu Arg Phe Asp Lys Ser Ile Glu Gly Ala Leu Glu Lys Val Arg
65                  70                  75                  80

Ala Phe Ser Gly Asp Gly Leu Phe Thr Ser Trp Thr His Glu Pro Asn
            85                  90                  95

Trp Arg Lys Ala His Asn Ile Leu Met Pro Thr Phe Ser Gln Arg Ala
        100                 105                 110
```

```
Met Lys Asp Tyr His Glu Lys Met Val Asp Ile Ala Val Gln Leu Ile
            115                 120                 125
Gln Lys Trp Ala Arg Leu Asn Pro Asn Glu Ala Val Asp Val Pro Gly
    130                 135                 140
Asp Met Thr Arg Leu Thr Leu Asp Thr Ile Gly Leu Cys Gly Phe Asn
145                 150                 155                 160
Tyr Arg Phe Asn Ser Tyr Tyr Arg Glu Thr Pro His Pro Phe Ile Asn
                165                 170                 175
Ser Met Val Arg Ala Leu Asp Glu Ala Met His Gln Met Gln Arg Leu
            180                 185                 190
Asp Val Gln Asp Lys Leu Met Val Arg Thr Lys Arg Gln Phe Arg Tyr
    195                 200                 205
Asp Ile Gln Thr Met Phe Ser Leu Val Asp Ser Ile Ile Ala Glu Arg
210                 215                 220
Arg Ala Asn Gly Asp Gln Asp Glu Lys Asp Leu Leu Ala Arg Met Leu
225                 230                 235                 240
Asn Val Glu Asp Pro Glu Thr Gly Glu Lys Leu Asp Asp Glu Asn Ile
                245                 250                 255
Arg Phe Gln Ile Ile Thr Phe Leu Ile Ala Gly His Glu Thr Thr Ser
            260                 265                 270
Gly Leu Leu Ser Phe Ala Thr Tyr Phe Leu Leu Lys His Pro Asp Lys
    275                 280                 285
Leu Lys Lys Ala Tyr Glu Glu Val Asp Arg Val Leu Thr Asp Ala Ala
    290                 295                 300
Pro Thr Tyr Lys Gln Val Leu Glu Leu Thr Tyr Ile Arg Met Ile Leu
305                 310                 315                 320
Asn Glu Ser Leu Arg Leu Trp Pro Thr Ala Pro Ala Phe Ser Leu Tyr
                325                 330                 335
Pro Lys Glu Asp Thr Val Ile Gly Gly Lys Phe Pro Ile Thr Thr Asn
            340                 345                 350
Asp Arg Ile Ser Val Leu Ile Pro Gln Leu His Arg Asp Arg Asp Ala
    355                 360                 365
Trp Gly Lys Asp Ala Glu Glu Phe Arg Pro Glu Arg Phe Glu His Gln
    370                 375                 380
Asp Gln Val Pro His His Ala Tyr Lys Pro Phe Gly Asn Gly Gln Arg
385                 390                 395                 400
Ala Cys Ile Gly Met Gln Phe Ala Leu His Glu Ala Thr Leu Val Leu
                405                 410                 415
Gly Met Ile Leu Lys Tyr Phe Thr Leu Ile Asp His Glu Asn Tyr Glu
            420                 425                 430
Leu Asp Ile Lys Gln Thr Leu Thr Leu Lys Pro Gly Asp Phe His Ile
    435                 440                 445
Ser Val Gln Ser Arg His Gln Glu Ala Ile His Ala Asp Val Gln Ala
    450                 455                 460
Ala Glu Lys Ala Ala Pro Asp Glu Gln Lys Glu Lys Thr Glu Ala Lys
465                 470                 475                 480
Gly Ala Ser Val Ile Gly Leu Asn Asn Arg Pro Leu Leu Val Leu Tyr
                485                 490                 495
Gly Ser Asp Thr Gly Thr Ala Glu Gly Val Ala Arg Glu Leu Ala Asp
            500                 505                 510
Thr Ala Ser Leu His Gly Val Arg Thr Lys Thr Ala Pro Leu Asn Asp
    515                 520                 525
Arg Ile Gly Lys Leu Pro Lys Glu Gly Ala Val Val Ile Val Thr Ser
```

```
            530                 535                 540
Ser Tyr Asn Gly Lys Pro Ser Asn Ala Gly Gln Phe Val Gln Trp
545                 550                 555                 560

Leu Gln Glu Ile Lys Pro Gly Leu Glu Gly Val His Tyr Ala Val
                565                 570                 575

Phe Gly Cys Gly Asp His Asn Trp Ala Ser Thr Tyr Gln Tyr Val Pro
            580                 585                 590

Arg Phe Ile Asp Glu Gln Leu Ala Glu Lys Gly Ala Thr Arg Phe Ser
            595                 600                 605

Ala Arg Gly Glu Gly Asp Val Ser Gly Asp Phe Glu Gly Gln Leu Asp
            610                 615                 620

Glu Trp Lys Lys Ser Met Trp Ala Asp Ala Ile Lys Ala Phe Gly Leu
625                 630                 635                 640

Glu Leu Asn Glu Asn Ala Asp Lys Glu Arg Ser Thr Leu Ser Leu Gln
                645                 650                 655

Phe Val Arg Gly Leu Gly Glu Ser Pro Leu Ala Arg Ser Tyr Glu Ala
            660                 665                 670

Ser His Ala Ser Ile Ala Glu Asn Arg Glu Leu Gln Ser Ala Asp Ser
            675                 680                 685

Asp Arg Ser Thr Arg His Ile Glu Ile Ala Leu Pro Pro Asp Val Glu
            690                 695                 700

Tyr Gln Glu Gly Asp His Leu Gly Val Leu Pro Lys Asn Ser Gln Thr
705                 710                 715                 720

Asn Val Ser Arg Ile Leu His Arg Phe Gly Leu Lys Gly Thr Asp Gln
                725                 730                 735

Val Thr Leu Ser Ala Ser Gly Arg Ser Ala Gly His Leu Pro Leu Gly
            740                 745                 750

Arg Pro Val Ser Leu His Asp Leu Leu Ser Tyr Ser Val Glu Val Gln
            755                 760                 765

Glu Ala Ala Thr Arg Ala Gln Ile Arg Glu Leu Ala Ser Phe Thr Val
            770                 775                 780

Cys Pro Pro His Arg Glu Leu Glu Glu Leu Ser Ala Glu Gly Val
785                 790                 795                 800

Tyr Gln Glu Gln Ile Leu Lys Lys Arg Ile Ser Met Leu Asp Leu Leu
                805                 810                 815

Glu Lys Tyr Glu Ala Cys Asp Met Pro Phe Glu Arg Phe Leu Glu Leu
            820                 825                 830

Leu Arg Pro Leu Lys Pro Arg Tyr Tyr Ser Ile Ser Ser Ser Pro Arg
            835                 840                 845

Val Asn Pro Arg Gln Ala Ser Ile Thr Val Gly Val Val Arg Gly Pro
850                 855                 860

Ala Trp Ser Gly Arg Gly Glu Tyr Arg Gly Val Ala Ser Asn Asp Leu
865                 870                 875                 880

Ala Glu Arg Gln Ala Gly Asp Val Val Met Phe Ile Arg Thr Pro
            885                 890                 895

Glu Ser Arg Phe Gln Leu Pro Lys Asp Pro Glu Thr Pro Ile Ile Met
            900                 905                 910

Val Gly Pro Gly Thr Gly Val Ala Pro Phe Arg Gly Phe Leu Gln Ala
            915                 920                 925

Arg Asp Val Leu Lys Arg Glu Gly Lys Thr Leu Gly Glu Ala His Leu
            930                 935                 940

Tyr Phe Gly Cys Arg Asn Asp Arg Asp Phe Ile Tyr Arg Asp Glu Leu
945                 950                 955                 960
```

```
Glu Arg Phe Glu Lys Asp Gly Ile Val Thr Val His Thr Ala Phe Ser
            965                 970                 975

Arg Lys Glu Gly Met Pro Lys Thr Tyr Val Gln His Leu Met Ala Asp
        980                 985                 990

Gln Ala Asp Thr Leu Ile Ser Ile Leu Asp Arg Gly Gly Arg Leu Tyr
    995                 1000                1005

Val Cys Gly Asp Gly Ser Lys Met Ala Pro Asp Val Glu Ala Ala
    1010                1015                1020

Leu Gln Lys Ala Tyr Gln Ala Val His Gly Thr Gly Glu Gln Glu
    1025                1030                1035

Ala Gln Asn Trp Leu Arg His Leu Gln Asp Thr Gly Met Tyr Ala
    1040                1045                1050

Lys Asp Val Trp Ala Gly Ile
    1055                1060

<210> SEQ ID NO 18
<211> LENGTH: 3165
<212> TYPE: DNA
<213> ORGANISM: Bacillus subtilis

<400> SEQUENCE: 18
```

| | | | | | |
|---|---|---|---|---|---|
| ttacattcct | gtccaaacgt | ctttcacata | acgtctttga | tcttgcagct | tttgcagcca | 60 |
| tacagctgat | tcttcctgac | ttgctgcttt | ttcagcttca | tatgccaatc | gcaaagttct | 120 |
| ctctacatca | ggagccattt | gcgatccatc | accgcatacg | taaatatgag | cccctttttc | 180 |
| aatgagtgtc | atcaatttct | gcgtatcttg | cttgagcaag | tgctggacat | atccttttgg | 240 |
| ttcgttttcg | acgcgcgagt | agcatcggcg | gattgtgacc | aaaccgtcct | gttccgcttg | 300 |
| atccagctct | tctctgtaaa | ggtcgtcatg | gtccgggcgg | cggcagccga | agtataaaag | 360 |
| tgcttcacca | agggtgcttc | cttccttctt | caaaaccgat | cttgcctgaa | taaagcctct | 420 |
| gaatggcgca | attcctgtgc | ccggcccgac | cataatcata | ggcgtttcag | gatcattcgg | 480 |
| catctgaaat | ccggactgcg | gcgtacgaat | gaagcaagct | gctgcatcac | ctgtattcaa | 540 |
| ttctgctaaa | taattagagg | cgacaccccg | gtattcacct | cggccgctcc | atgctgaggc | 600 |
| tttcacaact | cctaccgtca | tgctcacgat | atttgcatga | actttcggtg | agcttgaaat | 660 |
| ggaatagtat | ctcggttta | gtgatggcaa | aagtgctaaa | aaccgttcaa | acggcatttc | 720 |
| gcaagcagga | taatcctcta | aaaaatcaag | catggtaaga | cgttttgcaa | gtacctgctc | 780 |
| tttgtaaatg | ccatcatctg | aaacgagctg | ttccagctct | ttttgatgcg | gcggacaaac | 840 |
| tgtataagag | gccagctccc | gaagctgaag | ccttgatgcc | ggttcctgca | gctctacata | 900 |
| ggacgacaat | aaatccacta | ctttgattgg | ccgatccatc | ggcagatgag | ccatatgagc | 960 |
| gcttccgctt | acttttatca | catgattgga | ctgcaaaccg | aatcggctga | gaacccgctg | 1020 |
| aacaagctcc | ctgctgttct | ttggcaggat | tccgatatga | tcgccttctt | tatatgtttt | 1080 |
| accagccgga | atttccaatt | caatatggcg | ggttgaacgc | gtgctggcag | ctgtctggag | 1140 |
| ttctcgattc | tctaacacaa | tcccttcaaa | cgcgccatat | gctttagcaa | ccggcgtttc | 1200 |
| cgtcgcttca | ctgagaaaag | taatcgataa | tgaaggcctg | tcttctttct | gggctatttc | 1260 |
| gttaatatca | aatgcgtcca | tcgtttcctt | ccagaagcgg | ttttcccaag | actcgcggtg | 1320 |
| gctttcaaaa | tcatcggcgg | cgtcaccttc | cccaatcgct | gttaaacgcg | atgccccctt | 1380 |
| tgctttcatc | atgtcatcaa | tcaggcgggg | aatccgctga | tacgtgctgg | cccagctccg | 1440 |
| gtttccgcag | ccgaataccg | cataggaaac | acctttcaat | tggccttcct | caagctcttt | 1500 |

```
cagccactct acaaatccgg cagcattatc aggcggcgcc ccattataag aagccgttac    1560
aatgacgact gccccttctt cagggagctt gccgatataa tcatcaagcg gagccgtttc    1620
agctgtaaag cccatctggc ggccttgagc agccagttca ccggctattc cctcagctgt    1680
cccaagattt gaaccaaaaa gaacaagtaa aggtgtgccg tgtttaggtt tggtttctttt   1740 tggctttgtt tctgctttga tgtctgcctg ttcttttctc tgtacattga ttgccgctgt    1800
ttttcgcggt ttcacagtaa ttttaaaatc atccggcttg atcgttaatg cttctttgat    1860
ttttagttcg tagccagtat ggtttatcaa ttcaaaatgc tttaatacaa gaccgagaac    1920
cattgtcgct tcttgaagag caaactgcat gccaatacaa gcgcgctgtc cgtttccaaa    1980
cggcttatac gcatggtgag ggatacttga aggatcctca aaccgttccg gacggaaatc    2040
ttccgcatcc ggtccccaag cgttttgatc ccggtgcagt tttggaatta aaacagtgac    2100
tggctgccct tgctgatcg gatattcccc gcctagaaca gtatcctcct tcgcatatag    2160
agaaaaagcc ggagctgttg gatacagtct gagggtttca tttaaaacca tccgaatgta    2220
tttgagctgc tggatttgtt tatattcagg cgtgtcatcc gttaacacgc gatccgcttc    2280
ctcctgagct ttttttcagtt tttccggatg tgtaagcaga caataaatcg caaaggatag    2340
caacccgctt gttgtctcat gtccagcaat taaaaatgtg atgatttggt atcgaatgtt    2400
ttcgtcatcc agcgtttcac ccgttactgg atctttggca taaagcatga gagacaagag    2460
atccttaatg ttttcatccg gattcgcctt tcgctccgct atcattctat caaccaggga    2520
gttcatgact tctatatcct tttgaactg cagcttcgtt ttcaccatca ttttatcttg    2580
caggcccagt ctttttcgatt gattcatcgc ctctttttaag gcacggagca tactggtgat    2640
aaacggatgc tgtgaatcac ggtaaaaagct gttgaatcga tagttaaacc cgcataaccc    2700
aatcgtatca agcgtcagac gtgtcatatc gtccgctaca tcaatttctt cattagggtt    2760
taaccggctc cactttgtgaa tcagctgggt tgcgatatcc agcatcatag aatgatagcc    2820
tttcatcgct ttttgactaa aactcggcag caaaatgcgg tgggcttttt gccagttcgg    2880
ttcgtgcgtc cagcttgtaa ataagccatc tcccccgaac tcacgcacct tttgcaagcc    2940
tttgccaagg ttcttgtcaa agcgtttttc atcacacact tcagccacaa gattgtggcc    3000
ggacacaaaa acactggata ctcccggaaa atcaaaacgg aaaatcggtc ccaattcatc    3060
agctatccgc cataaggatt gagaaagctg ttcttttttcc agatgcggaa gatttttttaa    3120 aggtccgtat gttttgggct gaggtattgc gcttgcctgt ttcat                    3165
```

<210> SEQ ID NO 19
<211> LENGTH: 1053
<212> TYPE: PRT
<213> ORGANISM: Bacillus subtilis

<400> SEQUENCE: 19

Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg
            20                  25                  30

Ile Ala Asp Glu Leu Gly Pro Ile Phe Arg Phe Asp Phe Pro Gly Val
        35                  40                  45

Ser Ser Val Phe Val Ser Gly His Asn Leu Val Ala Glu Val Cys Asp
    50                  55                  60

Glu Lys Arg Phe Asp Lys Asn Leu Gly Lys Gly Leu Gln Lys Val Arg
65                  70                  75                  80

-continued

```
Glu Phe Gly Gly Asp Gly Leu Phe Thr Ser Trp Thr His Glu Pro Asn
                85                  90                  95
Trp Gln Lys Ala His Arg Ile Leu Leu Pro Ser Phe Ser Gln Lys Ala
            100                 105                 110
Met Lys Gly Tyr His Ser Met Met Leu Asp Ile Ala Thr Gln Leu Ile
        115                 120                 125
Gln Lys Trp Ser Arg Leu Asn Pro Asn Glu Glu Ile Asp Val Ala Asp
    130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Ser Gln His Pro Phe Ile Thr
                165                 170                 175
Ser Met Leu Arg Ala Leu Lys Glu Ala Met Asn Gln Ser Lys Arg Leu
            180                 185                 190
Gly Leu Gln Asp Lys Met Met Val Lys Thr Lys Leu Gln Phe Gln Lys
        195                 200                 205
Asp Ile Glu Val Met Asn Ser Leu Val Asp Arg Met Ile Ala Glu Arg
    210                 215                 220
Lys Ala Asn Pro Asp Glu Asn Ile Lys Asp Leu Leu Ser Leu Met Leu
225                 230                 235                 240
Tyr Ala Lys Asp Pro Val Thr Gly Glu Thr Leu Asp Asp Glu Asn Ile
                245                 250                 255
Arg Tyr Gln Ile Ile Thr Phe Leu Ile Ala Gly His Glu Thr Thr Ser
            260                 265                 270
Gly Leu Leu Ser Phe Ala Ile Tyr Cys Leu Leu Thr His Pro Glu Lys
        275                 280                 285
Leu Lys Lys Ala Gln Glu Glu Ala Asp Arg Val Leu Thr Asp Asp Thr
    290                 295                 300
Pro Glu Tyr Lys Gln Ile Gln Gln Leu Lys Tyr Ile Arg Met Val Leu
305                 310                 315                 320
Asn Glu Thr Leu Arg Leu Tyr Pro Thr Ala Pro Ala Phe Ser Leu Tyr
                325                 330                 335
Ala Lys Glu Asp Thr Val Leu Gly Gly Glu Tyr Pro Ile Ser Lys Gly
            340                 345                 350
Gln Pro Val Thr Val Leu Ile Pro Lys Leu His Arg Asp Gln Asn Ala
        355                 360                 365
Trp Gly Pro Asp Ala Glu Asp Phe Arg Pro Glu Arg Phe Glu Asp Pro
    370                 375                 380
Ser Ser Ile Pro His His Ala Tyr Lys Pro Phe Gly Asn Gly Gln Arg
385                 390                 395                 400
Ala Cys Ile Gly Met Gln Phe Ala Leu Gln Glu Ala Thr Met Val Leu
                405                 410                 415
Gly Leu Val Leu Lys His Phe Glu Leu Ile Asn His Thr Gly Tyr Glu
            420                 425                 430
Leu Lys Ile Lys Glu Ala Leu Thr Ile Lys Pro Asp Asp Phe Lys Ile
        435                 440                 445
Thr Val Lys Pro Arg Lys Thr Ala Ala Ile Asn Val Gln Arg Lys Glu
    450                 455                 460
Gln Ala Asp Ile Lys Ala Glu Thr Lys Pro Lys Glu Thr Lys Pro Lys
465                 470                 475                 480
His Gly Thr Pro Leu Leu Val Leu Phe Gly Ser Asn Leu Gly Thr Ala
                485                 490                 495
```

-continued

Glu Gly Ile Ala Gly Glu Leu Ala Ala Gln Gly Arg Gln Met Gly Phe
            500                 505                 510

Thr Ala Glu Thr Ala Pro Leu Asp Asp Tyr Ile Gly Lys Leu Pro Glu
            515                 520                 525

Glu Gly Ala Val Val Ile Val Thr Ala Ser Tyr Asn Gly Ala Pro Pro
            530                 535                 540

Asp Asn Ala Ala Gly Phe Val Glu Trp Leu Lys Glu Leu Glu Glu Gly
545                 550                 555                 560

Gln Leu Lys Gly Val Ser Tyr Ala Val Phe Gly Cys Gly Asn Arg Ser
                565                 570                 575

Trp Ala Ser Thr Tyr Gln Arg Ile Pro Arg Leu Ile Asp Asp Met Met
            580                 585                 590

Lys Ala Lys Gly Ala Ser Arg Leu Thr Ala Ile Gly Glu Gly Asp Ala
            595                 600                 605

Ala Asp Asp Phe Glu Ser His Arg Glu Ser Trp Glu Asn Arg Phe Trp
            610                 615                 620

Lys Glu Thr Met Asp Ala Phe Asp Ile Asn Glu Ile Ala Gln Lys Glu
625                 630                 635                 640

Asp Arg Pro Ser Leu Ser Ile Thr Phe Leu Ser Glu Ala Thr Glu Thr
                645                 650                 655

Pro Val Ala Lys Ala Tyr Gly Ala Phe Glu Gly Ile Val Leu Glu Asn
            660                 665                 670

Arg Glu Leu Gln Thr Ala Ala Ser Thr Arg Ser Thr Arg His Ile Glu
            675                 680                 685

Leu Glu Ile Pro Ala Gly Lys Thr Tyr Lys Glu Gly Asp His Ile Gly
            690                 695                 700

Ile Leu Pro Lys Asn Ser Arg Glu Leu Val Gln Arg Val Leu Ser Arg
705                 710                 715                 720

Phe Gly Leu Gln Ser Asn His Val Ile Lys Val Ser Gly Ser Ala His
                725                 730                 735

Met Ala His Leu Pro Met Asp Arg Pro Ile Lys Val Val Asp Leu Leu
            740                 745                 750

Ser Ser Tyr Val Glu Leu Gln Glu Pro Ala Ser Arg Leu Gln Leu Arg
            755                 760                 765

Glu Leu Ala Ser Tyr Thr Val Cys Pro Pro His Gln Lys Glu Leu Glu
            770                 775                 780

Gln Leu Val Ser Asp Asp Gly Ile Tyr Lys Glu Gln Val Leu Ala Lys
785                 790                 795                 800

Arg Leu Thr Met Leu Asp Phe Leu Glu Asp Tyr Pro Ala Cys Glu Met
                805                 810                 815

Pro Phe Glu Arg Phe Leu Ala Leu Leu Pro Ser Leu Lys Pro Arg Tyr
            820                 825                 830

Tyr Ser Ile Ser Ser Ser Pro Lys Val His Ala Asn Ile Val Ser Met
            835                 840                 845

Thr Val Gly Val Val Lys Ala Ser Ala Trp Ser Gly Arg Gly Glu Tyr
            850                 855                 860

Arg Gly Val Ala Ser Asn Tyr Leu Ala Glu Leu Asn Thr Gly Asp Ala
865                 870                 875                 880

Ala Ala Cys Phe Ile Arg Thr Pro Gln Ser Gly Phe Gln Met Pro Asn
                885                 890                 895

Asp Pro Glu Thr Pro Met Ile Met Val Gly Pro Gly Thr Gly Ile Ala
            900                 905                 910

Pro Phe Arg Gly Phe Ile Gln Ala Arg Ser Val Leu Lys Lys Glu Gly

```
                915                 920                 925
Ser Thr Leu Gly Glu Ala Leu Leu Tyr Phe Gly Cys Arg Arg Pro Asp
    930                 935                 940

His Asp Asp Leu Tyr Arg Glu Glu Leu Asp Gln Ala Glu Gln Asp Gly
945                 950                 955                 960

Leu Val Thr Ile Arg Arg Cys Tyr Ser Arg Val Glu Asn Glu Pro Lys
                965                 970                 975

Gly Tyr Val Gln His Leu Leu Lys Gln Asp Thr Gln Lys Leu Met Thr
            980                 985                 990

Leu Ile Glu Lys Gly Ala His Ile Tyr Val Cys Gly Asp Gly Ser Gln
        995                 1000                1005

Met Ala Pro Asp Val Glu Arg Thr Leu Arg Leu Ala Tyr Glu Ala
    1010                1015                1020

Glu Lys Ala Ala Ser Gln Glu Ser Ala Val Trp Leu Gln Lys
    1025                1030                1035

Leu Gln Asp Gln Arg Arg Tyr Val Lys Asp Val Trp Thr Gly Met
    1040                1045                1050
```

<210> SEQ ID NO 20
<211> LENGTH: 64
<212> TYPE: PRT
<213> ORGANISM: Artificial Sequence
<220> FEATURE:
<223> OTHER INFORMATION: Fragment of P450 heme domain

<400> SEQUENCE: 20

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60
```

<210> SEQ ID NO 21
<211> LENGTH: 65
<212> TYPE: PRT
<213> ORGANISM: Artificial Sequence
<220> FEATURE:
<223> OTHER INFORMATION: Fragment of P450 heme domain

<400> SEQUENCE: 21

```
Lys Glu Thr Ser Pro Ile Pro Gln Pro Lys Thr Phe Gly Pro Leu Gly
1               5                   10                  15

Asn Leu Pro Leu Ile Asp Lys Asp Lys Pro Thr Leu Ser Leu Ile Lys
            20                  25                  30

Leu Ala Glu Glu Gln Gly Pro Ile Phe Gln Ile His Thr Pro Ala Gly
        35                  40                  45

Thr Thr Ile Val Val Ser Gly His Glu Leu Val Lys Glu Val Cys Asp
    50                  55                  60

Glu
65
```

<210> SEQ ID NO 22
<211> LENGTH: 65
<212> TYPE: PRT
<213> ORGANISM: Artificial Sequence
<220> FEATURE:

<223> OTHER INFORMATION: Fragment of P450 heme domain

<400> SEQUENCE: 22

Lys Gln Ala Ser Ala Ile Pro Gln Pro Lys Thr Tyr Gly Pro Leu Lys
1               5                   10                  15

Asn Leu Pro His Leu Glu Lys Glu Gln Leu Ser Gln Ser Leu Trp Arg
            20                  25                  30

Ile Ala Asp Glu Leu Gly Pro Ile Phe Arg Phe Asp Phe Pro Gly Val
        35                  40                  45

Ser Ser Val Phe Val Ser Gly His Asn Leu Val Ala Glu Val Cys Asp
    50                  55                  60

Glu
65

<210> SEQ ID NO 23
<211> LENGTH: 58
<212> TYPE: PRT
<213> ORGANISM: Artificial Sequence
<220> FEATURE:
<223> OTHER INFORMATION: Fragment of P450 heme domain

<400> SEQUENCE: 23

Ser Arg Phe Asp Lys Asn Leu Ser Gln Ala Leu Lys Phe Val Arg Asp
1               5                   10                  15

Phe Ala Gly Asp Gly Leu Ala Thr Ser Trp Thr His Gly Lys Asn Trp
            20                  25                  30

Lys Lys Ala His Asn Ile Leu Leu Pro Ser Phe Ser Gln Gln Ala Met
        35                  40                  45

Lys Gly Tyr His Ala Met Met Val Asp Ile
    50                  55

<210> SEQ ID NO 24
<211> LENGTH: 58
<212> TYPE: PRT
<213> ORGANISM: Artificial Sequence
<220> FEATURE:
<223> OTHER INFORMATION: Fragment of P450 heme domain

<400> SEQUENCE: 24

Glu Arg Phe Asp Lys Ser Ile Glu Gly Ala Leu Glu Lys Val Arg Ala
1               5                   10                  15

Phe Ser Gly Asp Gly Leu Ala Thr Ser Trp Thr His Glu Pro Asn Trp
            20                  25                  30

Arg Lys Ala His Asn Ile Leu Met Pro Thr Phe Ser Gln Arg Ala Met
        35                  40                  45

Lys Asp Tyr His Glu Lys Met Val Asp Ile
    50                  55

<210> SEQ ID NO 25
<211> LENGTH: 58
<212> TYPE: PRT
<213> ORGANISM: Artificial Sequence
<220> FEATURE:
<223> OTHER INFORMATION: Fragment of P450 heme domain

<400> SEQUENCE: 25

Lys Arg Phe Asp Lys Asn Leu Gly Lys Gly Leu Gln Lys Val Arg Glu
1               5                   10                  15

Phe Gly Gly Asp Gly Leu Ala Thr Ser Trp Thr His Glu Pro Asn Trp
            20                  25                  30

Gln Lys Ala His Arg Ile Leu Leu Pro Ser Phe Ser Gln Lys Ala Met
             35                  40                  45

Lys Gly Tyr His Ser Met Met Leu Asp Ile
     50                  55

<210> SEQ ID NO 26
<211> LENGTH: 44
<212> TYPE: PRT
<213> ORGANISM: Artificial Sequence
<220> FEATURE:
<223> OTHER INFORMATION: Fragment of P450 heme domain

<400> SEQUENCE: 26

Ala Val Gln Leu Val Gln Lys Trp Glu Arg Leu Asn Ala Asp Glu His
1               5                   10                  15

Ile Glu Val Pro Glu Asp Met Thr Arg Leu Thr Leu Asp Thr Ile Gly
             20                  25                  30

Leu Cys Gly Phe Asn Tyr Arg Phe Asn Ser Phe Tyr
             35                  40

<210> SEQ ID NO 27
<211> LENGTH: 44
<212> TYPE: PRT
<213> ORGANISM: Artificial Sequence
<220> FEATURE:
<223> OTHER INFORMATION: Fragment of P450 heme domain

<400> SEQUENCE: 27

Ala Val Gln Leu Ile Gln Lys Trp Ala Arg Leu Asn Pro Asn Glu Ala
1               5                   10                  15

Val Asp Val Pro Gly Asp Met Thr Arg Leu Thr Leu Asp Thr Ile Gly
             20                  25                  30

Leu Cys Gly Phe Asn Tyr Arg Phe Asn Ser Tyr Tyr
             35                  40

<210> SEQ ID NO 28
<211> LENGTH: 44
<212> TYPE: PRT
<213> ORGANISM: Artificial Sequence
<220> FEATURE:
<223> OTHER INFORMATION: Fragment of P450 heme domain

<400> SEQUENCE: 28

Ala Thr Gln Leu Ile Gln Lys Trp Ser Arg Leu Asn Pro Asn Glu Glu
1               5                   10                  15

Ile Asp Val Ala Asp Asp Met Thr Arg Leu Thr Leu Asp Thr Ile Gly
             20                  25                  30

Leu Cys Gly Phe Asn Tyr Arg Phe Asn Ser Phe Tyr
             35                  40

<210> SEQ ID NO 29
<211> LENGTH: 50
<212> TYPE: PRT
<213> ORGANISM: Artificial Sequence
<220> FEATURE:
<223> OTHER INFORMATION: Fragment of P450 heme domain

<400> SEQUENCE: 29

Arg Asp Gln Pro His Pro Phe Ile Thr Ser Met Val Arg Ala Leu Asp
1               5                   10                  15

Glu Ala Met Asn Lys Leu Gln Arg Ala Asn Pro Asp Asp Pro Ala Tyr
             20                  25                  30

Asp Glu Asn Lys Arg Gln Phe Gln Glu Asp Ile Lys Val Met Asn Asp
            35                  40                  45

Leu Val
    50

<210> SEQ ID NO 30
<211> LENGTH: 50
<212> TYPE: PRT
<213> ORGANISM: Artificial Sequence
<220> FEATURE:
<223> OTHER INFORMATION: Fragment of P450 heme domain

<400> SEQUENCE: 30

Arg Glu Thr Pro His Pro Phe Ile Asn Ser Met Val Arg Ala Leu Asp
1               5                   10                  15

Glu Ala Met His Gln Met Gln Arg Leu Asp Val Gln Asp Lys Leu Met
            20                  25                  30

Val Arg Thr Lys Arg Gln Phe Arg Tyr Asp Ile Gln Thr Met Phe Ser
            35                  40                  45

Leu Val
    50

<210> SEQ ID NO 31
<211> LENGTH: 50
<212> TYPE: PRT
<213> ORGANISM: Artificial Sequence
<220> FEATURE:
<223> OTHER INFORMATION: Fragment of P450 heme domain

<400> SEQUENCE: 31

Arg Asp Ser Gln His Pro Phe Ile Thr Ser Met Leu Arg Ala Leu Lys
1               5                   10                  15

Glu Ala Met Asn Gln Ser Lys Arg Leu Gly Leu Gln Asp Lys Met Met
            20                  25                  30

Val Lys Thr Lys Leu Gln Phe Gln Lys Asp Ile Glu Val Met Asn Ser
            35                  40                  45

Leu Val
    50

<210> SEQ ID NO 32
<211> LENGTH: 52
<212> TYPE: PRT
<213> ORGANISM: Artificial Sequence
<220> FEATURE:
<223> OTHER INFORMATION: Fragment of P450 heme domain

<400> SEQUENCE: 32

Asp Lys Ile Ile Ala Asp Arg Lys Ala Ser Gly Glu Gln Ser Asp Asp
1               5                   10                  15

Leu Leu Thr His Met Leu Asn Gly Lys Asp Pro Glu Thr Gly Glu Pro
            20                  25                  30

Leu Asp Asp Glu Asn Ile Arg Tyr Gln Ile Ile Thr Phe Leu Ile Ala
            35                  40                  45

Gly His Glu Thr
    50

<210> SEQ ID NO 33
<211> LENGTH: 53
<212> TYPE: PRT
<213> ORGANISM: Artificial Sequence
<220> FEATURE:
<223> OTHER INFORMATION: Fragment of P450 heme domain

<400> SEQUENCE: 33

Asp Ser Ile Ile Ala Glu Arg Arg Ala Asn Gly Asp Gln Asp Glu Lys
1               5                   10                  15

Asp Leu Leu Ala Arg Met Leu Asn Val Glu Asp Pro Glu Thr Gly Glu
            20                  25                  30

Lys Leu Asp Asp Glu Asn Ile Arg Phe Gln Ile Ile Thr Phe Leu Ile
        35                  40                  45

Ala Gly His Glu Thr
    50

<210> SEQ ID NO 34
<211> LENGTH: 53
<212> TYPE: PRT
<213> ORGANISM: Artificial Sequence
<220> FEATURE:
<223> OTHER INFORMATION: Fragment of P450 heme domain

<400> SEQUENCE: 34

Asp Arg Met Ile Ala Glu Arg Lys Ala Asn Pro Asp Glu Asn Ile Lys
1               5                   10                  15

Asp Leu Leu Ser Leu Met Leu Tyr Ala Lys Asp Pro Val Thr Gly Glu
            20                  25                  30

Thr Leu Asp Asp Glu Asn Ile Arg Tyr Gln Ile Ile Thr Phe Leu Ile
        35                  40                  45

Ala Gly His Glu Thr
    50

<210> SEQ ID NO 35
<211> LENGTH: 61
<212> TYPE: PRT
<213> ORGANISM: Artificial Sequence
<220> FEATURE:
<223> OTHER INFORMATION: Fragment of P450 heme domain

<400> SEQUENCE: 35

Thr Ser Gly Leu Leu Ser Phe Ala Leu Tyr Phe Leu Val Lys Asn Pro
1               5                   10                  15

His Val Leu Gln Lys Ala Ala Glu Glu Ala Ala Arg Val Leu Val Asp
            20                  25                  30

Pro Val Pro Ser Tyr Lys Gln Val Lys Gln Leu Lys Tyr Val Gly Met
        35                  40                  45

Val Leu Asn Glu Ala Leu Arg Leu Trp Pro Thr Ala Ala
    50                  55                  60

<210> SEQ ID NO 36
<211> LENGTH: 60
<212> TYPE: PRT
<213> ORGANISM: Artificial Sequence
<220> FEATURE:
<223> OTHER INFORMATION: Fragment of P450 heme domain

<400> SEQUENCE: 36

Thr Ser Gly Leu Leu Ser Phe Ala Thr Tyr Phe Leu Leu Lys His Pro
1               5                   10                  15

Asp Lys Leu Lys Lys Ala Tyr Glu Glu Val Asp Arg Val Leu Thr Asp
            20                  25                  30

Ala Ala Pro Thr Tyr Lys Gln Val Leu Glu Leu Thr Tyr Ile Arg Met
        35                  40                  45

Ile Leu Asn Glu Ser Leu Arg Leu Trp Pro Thr Ala

<210> SEQ ID NO 37
<211> LENGTH: 60
<212> TYPE: PRT
<213> ORGANISM: Artificial Sequence
<220> FEATURE:
<223> OTHER INFORMATION: Fragment of P450 heme domain

<400> SEQUENCE: 37

```
Thr Ser Gly Leu Leu Ser Phe Ala Ile Tyr Cys Leu Leu Thr His Pro
1               5                   10                  15

Glu Lys Leu Lys Lys Ala Gln Glu Ala Asp Arg Val Leu Thr Asp
            20                  25                  30

Asp Thr Pro Glu Tyr Lys Gln Ile Gln Gln Leu Lys Tyr Ile Arg Met
        35                  40                  45

Val Leu Asn Glu Thr Leu Arg Leu Tyr Pro Thr Ala
    50                  55                  60
```

<210> SEQ ID NO 38
<211> LENGTH: 76
<212> TYPE: PRT
<213> ORGANISM: Artificial Sequence
<220> FEATURE:
<223> OTHER INFORMATION: Fragment of P450 heme domain

<400> SEQUENCE: 38

```
Pro Ala Phe Ser Leu Tyr Ala Lys Glu Asp Thr Val Leu Gly Gly Glu
1               5                   10                  15

Tyr Pro Leu Glu Lys Gly Asp Glu Leu Met Val Leu Ile Pro Gln Leu
            20                  25                  30

His Arg Asp Lys Thr Ile Trp Gly Asp Asp Val Glu Glu Phe Arg Pro
        35                  40                  45

Glu Arg Phe Glu Asn Pro Ser Ala Ile Pro Gln His Ala Phe Lys Pro
    50                  55                  60

Phe Gly Asn Gly Gln Arg Ala Cys Ile Gly Gln Gln
65                  70                  75
```

<210> SEQ ID NO 39
<211> LENGTH: 76
<212> TYPE: PRT
<213> ORGANISM: Artificial Sequence
<220> FEATURE:
<223> OTHER INFORMATION: Fragment of P450 heme domain

<400> SEQUENCE: 39

```
Pro Ala Phe Ser Leu Tyr Pro Lys Glu Asp Thr Val Ile Gly Gly Lys
1               5                   10                  15

Phe Pro Ile Thr Thr Asn Asp Arg Ile Ser Val Leu Ile Pro Gln Leu
            20                  25                  30

His Arg Asp Arg Asp Ala Trp Gly Lys Asp Ala Glu Glu Phe Arg Pro
        35                  40                  45

Glu Arg Phe Glu His Gln Asp Gln Val Pro His His Ala Tyr Lys Pro
    50                  55                  60

Phe Gly Asn Gly Gln Arg Ala Cys Ile Gly Met Gln
65                  70                  75
```

<210> SEQ ID NO 40
<211> LENGTH: 76
<212> TYPE: PRT
<213> ORGANISM: Artificial Sequence

```
<220> FEATURE:
<223> OTHER INFORMATION: Fragment of P450 heme domain

<400> SEQUENCE: 40

Pro Ala Phe Ser Leu Tyr Ala Lys Glu Asp Thr Val Leu Gly Gly Glu
1               5                   10                  15

Tyr Pro Ile Ser Lys Gly Gln Pro Val Thr Val Leu Ile Pro Lys Leu
            20                  25                  30

His Arg Asp Gln Asn Ala Trp Gly Pro Asp Ala Glu Asp Phe Arg Pro
        35                  40                  45

Glu Arg Phe Glu Asp Pro Ser Ser Ile Pro His His Ala Tyr Lys Pro
    50                  55                  60

Phe Gly Asn Gly Gln Arg Ala Cys Ile Gly Met Gln
65                  70                  75

<210> SEQ ID NO 41
<211> LENGTH: 59
<212> TYPE: PRT
<213> ORGANISM: Artificial Sequence
<220> FEATURE:
<223> OTHER INFORMATION: Fragment of P450 heme domain

<400> SEQUENCE: 41

Phe Ala Leu His Glu Ala Thr Leu Val Leu Gly Met Met Leu Lys His
1               5                   10                  15

Phe Asp Phe Glu Asp His Thr Asn Tyr Glu Leu Asp Ile Lys Glu Thr
            20                  25                  30

Leu Thr Leu Lys Pro Glu Gly Phe Val Val Lys Ala Lys Ser Lys Lys
        35                  40                  45

Ile Pro Leu Gly Gly Ile Pro Ser Pro Ser Thr
    50                  55

<210> SEQ ID NO 42
<211> LENGTH: 60
<212> TYPE: PRT
<213> ORGANISM: Artificial Sequence
<220> FEATURE:
<223> OTHER INFORMATION: Fragment of P450 heme domain

<400> SEQUENCE: 42

Phe Ala Leu His Glu Ala Thr Leu Val Leu Gly Met Ile Leu Lys Tyr
1               5                   10                  15

Phe Thr Leu Ile Asp His Glu Asn Tyr Glu Leu Asp Ile Lys Gln Thr
            20                  25                  30

Leu Thr Leu Lys Pro Gly Asp Phe His Ile Ser Val Gln Ser Arg His
        35                  40                  45

Gln Glu Ala Ile His Ala Asp Val Gln Ala Ala Glu
    50                  55                  60

<210> SEQ ID NO 43
<211> LENGTH: 60
<212> TYPE: PRT
<213> ORGANISM: Artificial Sequence
<220> FEATURE:
<223> OTHER INFORMATION: Fragment of P450 heme domain

<400> SEQUENCE: 43

Phe Ala Leu Gln Glu Ala Thr Met Val Leu Gly Leu Val Leu Lys His
1               5                   10                  15

Phe Glu Leu Ile Asn His Thr Gly Tyr Glu Leu Lys Ile Lys Glu Ala
            20                  25                  30
```

```
Leu Thr Ile Lys Pro Asp Asp Phe Lys Ile Thr Val Lys Pro Arg Lys
        35                  40                  45

Thr Ala Ala Ile Asn Val Gln Arg Lys Glu Gln Ala
50                  55                  60
```